(12) United States Patent
Larsen et al.

(10) Patent No.: US 6,936,586 B1
(45) Date of Patent: *Aug. 30, 2005

(54) SYNTHETIC IL-10 ANALOGUES

(75) Inventors: Christian Grønhøj Larsen, Aarhus (DK); Borbala Gesser, Hasselager (DK)

(73) Assignee: Steeno Research Group A/S, Odense (DK)

( * ) Notice: Subject to any disclaimer, the term of this patent is extended or adjusted under 35 U.S.C. 154(b) by 0 days.

This patent is subject to a terminal disclaimer.

(21) Appl. No.: 09/101,825
(22) PCT Filed: Jan. 16, 1997
(86) PCT No.: PCT/DK98/00021
§ 371 (c)(1),
(2), (4) Date: Jul. 17, 1998
(87) PCT Pub. No.: WO97/26279
PCT Pub. Date: Jul. 24, 1997

(30) Foreign Application Priority Data

Jan. 18, 1996 (WO) .............................. PCT/DK96/00029

(51) Int. Cl.[7] ........................ A61K 38/19; A61K 38/20
(52) U.S. Cl. .............................. 514/15; 514/8; 514/12; 514/13; 514/14; 424/85.2; 530/300; 530/317; 530/328
(58) Field of Search .............................. 514/15, 8, 12, 514/13, 14; 424/85.2; 530/300, 317, 328; 435/6; 536/23.7, 23.1, 23.2, 24.32

(56) References Cited

U.S. PATENT DOCUMENTS

| 4,235,871 A | 11/1980 | Papahadjopoulos et al. |
| 4,501,728 A | 2/1985 | Geho et al. |
| 4,837,028 A | 6/1989 | Allen |
| 5,446,128 A | 8/1995 | Kahn |
| 5,654,276 A | * 8/1997 | Barrett et al. .................. 514/13 |

FOREIGN PATENT DOCUMENTS

| CA | 2085291 | 12/1992 |
| WO | 9317698 | 9/1993 |
| WO | 9503411 | 2/1995 |

OTHER PUBLICATIONS

Vieira et al, Proceedings of National Academy of Sciences, USA, vol. 88, pp. 1172–1176, Feb. 1991.*
Koonce, M.P., et al., "Dynein from *Dictyostelium*: Primary Structure Comparisons Between a Cytoplasmic Motor Enzyme and Flagellar Dynein," *The Journal of Cell Biology* 119(6): 1597–1604 (1992).
Harlow, E., et al., "Antibodies That React with Predetermined Sites on Proteins," *Science* 219:660–666 (1983).
Sutcliffe, J.G., et al., "Antibodies That React with Predetermined Sites on Proteins," *SCIENCE* 219:660–666 (1983).
Rudinger, J., "Characteristics of the Amino Acids as Components of a Peptide Hormone Sequence," *Peptide Hormones* University Park Press pp. 1–7 (1976).
Kimball, J.W., "Introduction to Immunology," Macmillan Publishing Co., Inc., pp. 438–439 (1983).
Bendtzen K. Lymphokines in inflammation. Inflammation Basic Mechanisms Tissue Injuring Principles and Clinical Models (P Venge & A Lindbom eds) 1985; Almqvist & Wiksell International. Stockholm: 187–217.
Bendtzen K. Interleukin–1, Interleukin–6, and tumor necrosis factor in infection, inflammation and immunity, Immunol Lett 1988;19:183–192.
Larsen C.G. Leukocyte activating and chemotactic cytokines in cell–mediated immune reactions of the human skin. Acta Dermatovenerol. 1991; Suppl. 160:1–48.
Fiorentino D.F., M. W. Bond, and T.R. Mosmann. 1989. Two types of mouse helper T cell. IV. Th2 clones secrete a factor that inhibits cytokine production by Th 1 clones. J. Exp. Med., 170:2081.
Viera P., R. de Wall–Malefyt, M.–N. Dang, K. E. Johnson, R. Kastelein, D. F. Fiorentiono, J. E. de Vries, M.–G. Roncarolo, T. R. Mosmann, and K. W. Moore. 1991. Isolation and expression of human cytokine synthesis inhibitory factor (CSIF/IL–10) cDNA clones: homology to Epstein–Barr virus open reading frame BCRFI. Proc. Natl. Acad. Sci. (USA), 88:1172.
Moore, K.W., O'Garra A., de Waal Malefyt R., Vieira, Mosmann T.R. 1993. Interleukin–10, Annu Rev. Immunol, 11:165–90.
Kim, J.M., Brannan, C.I. Copeland N.G., Jenkins, N.A., Khan, T.A., Moore, K.W. 1992. Structure of the mouse interleukin–10 gene and chromosomal localization of the mouse and human genes. J. Immunol 148:3618–23.
Carter, D.B., Deibel, M.R–Jr, Dunn, C.J. et al. 1990. Purification, cloning, expression and biological characterization of an interleukin–1 receptor antagonist protein. Nature 344:633–638.
Hannum, C.H., Wilcox, C.J., Arend, W.P. et al. 1990. Interleukin–1 receptor antagonist activity of a human interleukin–1 inhibitor. Nature 343:336–40.
Firestein, G.S., Boyle, D.L., Yu, C., et al. 1994. Synovial interleukin–1 receptor antagonist and interleukin–1 balance in rheumatoid arthritis. Arthritis Rheum 37:644–652.
Fisher, C.J.–Jr.,Slotman, G.J., Opal, S.M., Pribble, J.P. et al. 1994. Initial evaluation of recombinant interleukin–1 receptor antagonist in the treatment of sepsis syndrome: a randomized, open–label, placebo–controlled multicenter trial. The IL–1RA Sepsis Syndrome Study Group. CritCare–Med. 22:12–21.

(Continued)

*Primary Examiner*—Gary Kunz
*Assistant Examiner*—Fozia Hamud
(74) *Attorney, Agent, or Firm*—Iver P. Cooper

(57) ABSTRACT

The nonapeptide NH2-Ala-Tyr-Met-Thr-Met-Lys-Ile-Arg-Asn-COOH (SEQ ID NO: 1) and related molecules are useful as IL-10 agonists.

33 Claims, 14 Drawing Sheets

OTHER PUBLICATIONS de Waal–Malefyt, R., Haanen J., Spits, H., et al. 1991. IL–10 and viral IL–10 strongly reduce antigen–specific human T cell proliferation by diminishing the antigen–presenting capacity of monocytes via down–reulation of class II MHC expression. J. Exp. Med. 174:915–24.

Gazzinelli, R.T., Oswald, I.P., James, S.L., Sher, A., 1992. IL–10 inhibits parasite killing and nitric oxide production by IFN–\–activated macrophages. J. Immunol. 148:1792–96.

Jinquan, T., Larsen, C.G., Gesser, B., Matsushima, K., Thestrup–Pedersen, K. 1993.Human IL–10 is a chemoattractant for CD8+ T lymphocytes and an inhibitor of IL–8–induced CD4+ lymphocyte Migration. Journal of Immunology, 151:4545–4551.

Rousset F., E. Garcia, T. Defrance, C. Peronne, D.–H. Hsu, R. Kastelein, K. W. Moore, and J. Banchereau. 1992. IL–10 is a potent growth and differentiation factor for activated human B lymphocytes. Proc. Natl. Acad. Sci. USA, 175:671.

Howard, M., O'Garra, A., Ishida, H., de Waal Malefyt, R., de Vries, J. 1992. Biological properties of Interleukin–10. J. Clin. Immunol 12:239–47.

Kuhn, R., Lohler, J., Rennick, D., Rajewsky, K., Muller, W. 1993. Interleukin–10–deficient mice develop chronic enterocolitis. Cell 75: 263–74.

Sher, A., Fiorentino, D.F., Caspar, P., Pearce, E., Mosmann, T. 1991. Production of IL–10 by CD4+ lymphocytes correlates with down–regulation of Th1 cytokine synthesis in helminth infection. J. Immunol. 147:2713–16.

Clerici, M., Shearer, G.M. 1993 Immunology Today. 14:107–111.

Bry, K., Lappalainen, U. 1994. Interleukin–4 and transforming growth factor–beta 1 modulate the production of interleukin–1 receptor antagonist and prostaglandin E2 by decidual cells. Am–J–obstet–Gynecol 170 (4): 1194–1198.

Roberge, C. J., De–Medicis, R., Dayer, J. M., Rola–Pleszcyczynski, M., Naccahe, P. H., Poubelle, P. E. 1994. Crystal–induced neutrophil activation: V. Differential production of biologically active IL–1 receptor antagonist. J. Immunol 152/11: 5485–5494.

McCall, R. D., Haskill, S., Zimmermann, E. M., Lund, P. K., Thompson, R. C., Sartor, R. B. 1994. Tissue interluekin 1 and interleukin–1 receptor antagonist expression in entercolitis in resistant and susceptible rats. Gastroenterology (4): 960–72.

Kimble, R. B., Vannice, J. L., Bloedow, D. C., Thompson, R. C., Hopfer, W., Kung, V. T., Brownfield, C., Pacifici, R. 1994. Interleukin–1 receptor antagonist decreases bone loss and bone resorption in ovariectomized rats. J. Clin Invest. 93/5: 1959–1967.

Kline, J. N., Geist, L. J., Monick, M. M., Stinski, M. F., Hunninghake, G. W., 1994. J. Immunol. 152 (5): 2351–7.

Tompkins, R. G. 1994. Human recombinant interleukin–1 receptor antagonist in the treatment of sepsis syndrome (editorial; comment). Crit–Care–Med. 22 (1): 3, 22 (1): 12–21.

Everaedt, B., Brouckaert, P., Fiers, W. 1994. Recombination IL–1 receptor antagonist protects against TNF–induced lethality in mice. J. Immunol. 152/10: 5041–5049.

Fischer, C. J. Jr., Slotman, G. J., Opal, S. M., Pribble, J. P., Bone, R. C., Emmanuel, G., Ng, D., Bloedow, D. C., Catalano, M. A. 1994. Initial evaluation of human recombination interleukin–1 receptor antagonist in the treatment of sepsis syndrome: a randomized, open–label, placebo–controlled multicenter trial. The IL–IRA Sepsis Syndrome Study Group (see comments). Crit–Care–Med. 22(1): 12–21, 22(1): 3.

Gomez–Reino–Carnoto, J. J. 1994. New terapies in rheumatoid arthritis. Med–Clin 543–545. English Translation in Paper as Filed on Feb. 25, 1999.

Nishihara, T., Ohsaki, Y., Ueda, N., Saito, N., Mundy, G. R. 1994. Mouse interleukin–1 receptor antagonist induced by actinomycetem–comitans lipopolysaccharide blocks the effects of interleukin–1 om bone resorption and osteoclast–like cell formation. Infect–Immun. 62(2): 390–7.

Simon, C., Frances, A., Piquette, G. N., el–Danasouri, I., Zurawski, G., Dang, W., Polan, M. L. 1994. Embryonic implantation in mice is blocked by interleukin–1 receptor antagonist (see comments). Endocrinology. 134(2): 521–8, 134(2): 519–20.

Baergen, R., Benirschke, K., Ulich, T. R., 1994. Cytokine expression in the placenta. The role of interleukin 1 and interleukin 1 receptor antagonist expression in chorioamnionitis and parturition. Arch–Pathol–Lab–Med. 118(1): 52–5.

Tang, W.W., Feng, L., Vannice, J. L., Wilson, C. B. 1994. Interleukin–1 receptor antagonist ameliorates experimental antiglomerular basement membrane antibody–associated flomeulonephritis. J. Clin–Invest. 93(1): 279–9.

Cassatella, M. A., Meda, L., Gasperini, S., Calzetti, F., Bonara, S. 1994.Interleukin 10 (IL–10) upregulates IL–1 receptor antagonist production from lipopolysaccharide–stimulated human polymorphonuclear leukocytes by delaying mRNA degradation. J. Exp–Med. 179/5: 1695–1699.

Mancini, R., Bendetti, A., Jezequel, A. M. 1994. An interleukin–1 receptor antagonist decreases fibrosis induced by dimethylnitrosamine in rat liver. Virchows–Arch. 424/1: 25–31.

Lukacs, N. W., Kunkel, S. L., Burdick, M. D., Lincoln, P. M., Strieter, R. M. 1993. Interleukin–1 receptor antagonist blocks chemokine production in the mixed lymphocyte reaction. Blood. 82(12): 3668–74.

Bandara, G., Mueller, G. M., Galea–Lauri, J., Tindal, M. H., Georgescu, H. I., Suchanek, M. K., Hung, G. L., Gloriso, J. C., Robbins, P. D., Evans, C. H. 1993. Intraarticular expression of biologically active interleukin 1–receptor–antagonist protein by ex vivo transfer. Proc–Natl–Acad–Sci–U–S–A. 90(22): 10764–8.

Dinarello, C. A, 1994. Anti–interleukin–1 strategies in the treatment of the septic shock syndrome. Can–J–infect–Dis. 5(suppl. A): 9A–16A.

Oelmann, E., Topp, M. S., Reufi, B., Papadimitriiou, C., Koeningsmann, M., Oberberg, D., Thiel, E., Berdel, W. E. 1994. Int–J–Oncol. 4/3: 555–558.

Estrov, Z. 1993. Interruption of autocrine and paracine growth–stimolatory memchaisms: a new therapeutic stratefy for chronic myelogenous leukemia. Semin–Hematol. 30(3 suppl 3): 35–6.

Wooley, P.H., Whalen, J.D., Chapman, D.L., Berger, A.E., Richard, K.A., Aspar, D.G., Staite, N.D. 1993. The effect of an interleukin–1 receptor antagonist protein on type II collagen–induced arthritis and antigen–induced arthritis in mice. Arthritis Rheum. 36 (9): 1305–1314.

Peterson, C.M., Hales, H.A., Hatasaka, H.H., Mitchell, M.D., Rittenhouse, L., Jones, K.P. 1993. Interleukin–1 beat (IL–1 beta) modulates prostaglandin production and the natural IL–1 receptor antagonist inhibits ovulation in the optimally stimulated rat ovarian perfusion model. Endocrinology 133 (5): 2301–2306.

Estrov, Z., Kurzrock, R., Talpaz, M. 1993. Role of interleukin–1 inhibitory molecules in therapy of acute and chronic myelogenous leukemia. Leuk. Lymphoma 10 (6): 407–418.

Chensue, S. W., Bienkowski, M., Eessalu, T.E., Warmington, K.S., Hershey, S.D., Lukacs, N.W., Kunkel, S.L. 1993. nous IL–1 receptor antagonist protein (IRAP) regulates schistosome egg granuloma formation and the regional lymphoid response. J. Immunol. 151 (7): 3654–3662.

Bowyer, J.F., Davies, D.L., Schmued, L., Broening, H.W., Newport, G.D., Slikker, W Jr., Holson, R.R. 1994. Further studies of the role f hyperthermia in methamphetamine neurotoxicity. J. Pharmacol. Exp. Ther. 268/3: 1571–1580.

Cole, O.F., Sullivan, M.H.F., Elder, M.G. 1993. The 'interleukin–1 receptor antagonist' is a partial agonist of prostaglandin synthesis by human decidual cells. Prostaglandins 46/6: 493–498.

Jenkins, J.K., Arend, W.P. 1993. Interleukin 1 receptor antagonist production in human monocytes is induced by IL–1alpha, IL–3, and IL–4 and GM–CSF. Cytokine 5/5: 407–415.

Coceani, F., Lees, J., Redford, J., Bishai, I. 1992. Interleukin–1 receptor antagonist: effectiveness against interleukin–1 fever. Can. J. Pharmacol. 70 (12): 1590–1596.

Schiro, R., Longoni, D., Rossi, V., Maglia, O., Doni, A., Arsura, M., Carrara, G., Masera, G., Vannier, E., Dinarello, C.A., Rambaldi, A., Biondi, A. 1994. Suppression of juvenile chronic myelogenous leukemia colony growth by interleukin–1 receptor antagonist. Blood 83/2: 460–465.

Watson, M.L., Smith, D., Bourne, A.D., Thompson, R.C., Westwick, J. 1993. Cytokines contribute to airway dysfunction hyperreactivity, pulmonary eosinophil accumulation and tumor necrosis factor generation by pre–treatment with an interleukin–1 receptor antagonist. Am. J. Respir. Cell Mol. Biol. 8 (4): 365–369.

Abhyankar, S., Gilliland, D.G., Ferrara, J.L.M. 1993. Interleukin–1 is a critical effector molecule during cytokine dysregulation in graft–versus–host disease to minor histocompatibility antigens. Transplantation 56/6: 1518–1523.

Lan, H.Y., Nikolic Paterson, D.J., Zarama, M., Vannice, J.L., Atkins, R.C. 1993. Suppression of experimental crescentic glomerulonephitis by the interleukin–1 receptor antagonist. Kidney Int. 43 (2): 479–485.

Herve, P. 1993. Prevention and treatment of acute GvHD—New modalities. Nouv. Rev. Fr. Hematol. 35/3: 295–297.

Conti, P., Panara, M.R., Barbacane, R.C., Placido, F.C., Bongrazio, M., Reale, M., Dempsey, R.A., Fiore, S. 1992. Blocking the interleukin–1 receptor inhibits leukotriene B4 and prostaglandin E2 generation in human monocyte cultures. Cell Immunol. 145 (1):199–209.

Kristensen, M., Deleuran, B., Eedy, D.J., Feldmann, M., Breathnach, S.M., Brennan, F.M. 1992. Distribution of interleukin–1 receptor antagonist protein (IRAP), interleukin–1 receptor, and interleukin–1 alpha in normal and psoriatic skin, Decreased expression of IRAP in psoriatic lesional epidermis, Br. J. Dermatol. 127 (4): 305–311.

Romero, R., Sepulveda, W., Mazor, M., Brandt, F., Cotton, D.B., Dinarello, C.A:, Mitchell, M.D. 1992. The natural interleukin–1 receptor antagonist in term and pre–term parturition. Am. J. Obstet. Gynecol. 167 (4 Pt 1): 863–872.

Dinarello, C.A. 1992. Reduction of inflammation by decreasing production of interleukin–1 or by specific receptor antogonism. Int. J. Tissue. React. 14 (2): 65–75.

Conti, P., Panara, M.R., Barbacane, R.C., Bongrazio, M:, Dempsey, R.A., Reale, M. 1993. Human recombinant IL.1 receptor antagonist (IL–1Ra) inhibits leukotriene B4 generation from human monocyte suspensions stimulated by lipopolysaccharide (LPS). Clin. Exp. Immunol. 91/3: 526–531.

DeForge, L.E., Tracey, D.E., Kenney, J.S., Remick, D.G. 1992. Interluekin–1 receptor antagonist protein inhibits interluekin–8 expression in lipopolysaccharide–stimulated human whole blood. Am. J. Pathol. 140 (5): 1045–1054.

Porat, R., Poutsiaka, D.D., Miller, L.C., Granowitz, E.V., Dinarello, C.A. 1992. Interleukin–1 (IL–1) receptor blockade reduces endotoxin and Borrealia burgdorferi–stimulated IL–8 synthesis in human monoclear cells. Faseb. J. 6 (7): 2482–2486.

Boermeester, M.A., van Leeuwen, P.A.M., Schneider, A.J., Houdijk, A.P.J., Ferwerda, C.C., Wesdorp, R.I.C. 1993. Interleukin–1 receptor antagonist: A new therapeutic agent in the treatment of septic syndrome. Ned. Tijdschr. Geneesks: 137/7: 337–342.

Smith, R.J., Chin, J.E., Sam, L.M., Justen, J.M. 1991. Biologic effects of an interleukin–1 receptor antagonist protein on interleukin–1–stimulated cartilage erosion and chondrocyte responsiveness. Arthsitis Rheum. 34 (1): 78–83.

Conti, P. Barbacane, R.C., Panara, M.R., Reale, M., Placido, F.C., Fridas, S., Bongrazio, M., Dempsey, R.A. 1992. Human recombinant interleukin–1 receptor antagonist (hrIL–1ra) enhances the stimulatory effect of interleukin–2 on natural killer cell activity against MOLT–4 target cells. Int. J. Immunopharm. 14/6: 987–993.

Selig, W., Tocker, J. 1992. Effect of interleukin–1 receptor antagonist on antigen–induced pulmonary respsonses in guinea pigs. Eur. J. Pharmacol. 213/3: 331–336.

McCarthy, P.L. Jr., Abhyankar, S., Neben, S., Newman, G., Sieff, C., Thompson, R.C., Burakoff, S.J., Ferrara, J.L.M. 1991. Inhibition of interleukin–1 by an interleukin–1 receptor antagonist prevents graft–versus–host diseases.Blood 78/8: 1915–1918.

Estrov, Z, Kurzrock, R., Wetzler, M., Kantajian, H., Blake, M., Harris, D., Gutterman, J.U., Talpaz, M. 1991. Suppression of chronic myelongenous leukemia colony growth by interleukin–1 (IL–1) receptor antagonist and soluble IL–1 receptors: A novel application for inhibitors of IL–1 activity. Blood 78/6: 1476–1484.

Thomas, T.K., Will, P.C., Srivastava, A., Wilson, C.L., Harbison, M., Little, J., Chesonis, R.S., Pignatello, M., Schmolze, D., Symington, J., Kilin, P.L., Thompson, R.C. 1991. Evaluation of an interleukin–1 receptor antagonist in the rat acetic–induced colitis model. Agents Actions 34/1–2: 187–190.

Carter, D.B., Deibel, M.R. Jr., Dunn, C.J., Tomich, C.S.C., Laborde, A.L., Slightom, J.L., Berger, A.E., Bienkowski, M.J., Sun, F.F., McEwan, R.N., Harris, P.K.W., Yem, A. W., Waszak, G.A., Chosay, J.G., Siue, L.C., Hardee, M.M., Zurcher Neely, H.A., Reardon, I.M., Heinrikson, R.L. et al. 1990. Purification, cloning expression and biological characterization of an interleukin–1 receptor antagonist protein. Nature 344/6267: 633–638.

Larsen C.G, Anderson A.O, Apella, E., Oppenheim, J.J., Matsushima K., 1989. Science 243:1464.

Larsen C.G., Jinquan T., Deleurant B., Thestrup–Pedersen K. 1993, IL–10 is a potent regulator of the chemotactic response of mononuclear cells, but no of granulocytes. J. Invest. Dermatol. vol. 100, No 6.

Sankoff and Kruskal in chapter 1 of "Time Warps, String Edits, and Macro–molecules: The Theory and Practice of Sequence Comparison" (Addison–Wesley, Reading, Mass 1983).

Berzofsky, Science 229, (1985) 932–940.

Bowie et al., Science 247, (1990) 1306–1310.

Wasserman et al., J. Immunol. 87, 1961, 290–295.

Levine et al., Methods in Enzymology 11, 1967, 928–936.

Lewis et al., Biochemistry 22, 1983, 948–954.

Rene de Waal Maletyt, John Abrahams, Bruce Bennet, Carl G. Figdor and Jan E. de Vries (1991), Interleukin 10 (IL–10) Inhibits Cytokine Synthesis by Human Monocytes: An Autoregulatory Role of IL–10 Produced by Monocytes. J. Exp. Med. 174, 1209–1220.

Szoka et al., Ann. Rev. Biophys. Bioneng. 9, 1980, 467.

Walter H. Gotlieb, John S. Abrams, Joanna M. Watson, Thierry J. Velu, Jonathan S. Berek, Otniel Martinez–Meza (1992), Presence of interleukin 10 (IL–10) in the ascites of patients with ovarian and other intra–abdominal cancers. Cytokine 4, No. 5, 385–390.

Blancho G., P. Gianello, Sh. Germana, M. Baetscher, D.H. Sachs and Chr. LeGuern (1995), Molecular identification of porcine interleukin 10: Regulation of expression in kidney allograf model. Proc. Natl. Acad. Sci. USA 92, 2800–2804.

Howard, M., T. Muchameul, S. Andrade, S. Menon (1993), Interleukin 10 protects mice from lethal endotoxemia. J. Exp. Med. 177, 1205–1208.

Chernoff, A.E., E.V. Granowitz, L. Shapiro, E. Vannier, G. Lonnenmann, J.B. Angel, J.S. Kennedy, A.R. Rabson, S. Wolff, C.A. Dinarello (1995), A randomized, controlled trial of IL–10 in humans. Inhibition of inflammatory cytokine production and immune response. J. Immunol. 154, 5492–5499.

Banerjee, A.K., S.W. Galloway and A.N. Kingsnorth (1994), Experimental models of acute pancreatitis. Br. J. Sug. 81, 1096–1103.

Hong, S.S., D.S. Chin, T.S. Cho, S.E. Kim (1962), Experimental pancreatitis induced by alcohol and bile in rabbits. Annals of Surgery 156(6), 929–939.

Pelton, J.T., et al., Proc. Natl. Acad. Sci. USA 82, 233–239.

Dyson, H., et al. (1988), Annual Review of Biophysics and Biophysical Chemistry 17, 305–324).

Nakanishi, H., et al. (1993), Peptidomimetics of the immunoglobulin supergene family—a review. Gene 137, 51–56.

Walter et al. (1995), Biochemistry 34, 12118–25.

Marshall, G.R. (1993), Tetrahedron 49, 3547–3558.

Merrifield, R.B. (1963), J. Amer. Chem. Soc. 85, 2149–2154).

Kent, S.B.H. (1988), Annu. Rev. Biochem. 57, 957–989.

Carpino, L.A. and Han, G.Y. (1972), J. Org. Chem. 37, 3404–3409.

Ikeda, N. et al. (1995), Infection and Immunity, 4812–4817.

Fink, G.W. and Norman, J.G. (1996), "Intrapancreatic Interleukin–1β Gene Expression by Specific Leukocyte Populations during Acute Pancreatitis", J. Surgical Research 63, 369–373.

Gaur, D. et al. (1996), "Phylogenetic position of the order Lagomorpha (rabbits, hares and allies)", Nature, 379, 333–335.

Poli, G. et al. (1994), Proc. Natl. Acad. Sci. USA 91, 108–112.

Jensen, I.M. et al. (1993), Analyt. Cell. Pathol. 5, 213–223.

Berman, R.M., Suzuki, T. et al. (1996), "Systemic administration of cellular IL–10 induces an effective, specific, longlived immune response against established tumors in mice", J. Immunol. 157, 231–238.

Zheng, L.M., Ojcius, D.M. et al. (1996), "IL–10 inhibits tumor metastasis through and NK cell–dependent mechanism", J. Exp. Med. 184, 579–584.

Kundu, N., Beaty, T.L. et al. (1996), "Antimetastic and anti–tumor activities of IL–10 in a murine model of breast cancer", J. Natl. Cancer Inst. 88, 479–480.

Kollmann, T.R., Pettoello–Mantovani, M. et al. (1996), "Inhibition of acute in vivo HIV infection by human IL–10 treatment of SCID mice implanted with human fetal thymus and liver", Proc. Natl. Acad. Sci. USA 93, 3126–3131.

Maini, R.N. (1996), "A perspective on anti–cytokine and anti T cell directed therapies in rheumatoid arthritis", Clin. Exp. Rheumatol. 13, suppl. 12, S35–40.

WO 93/02693.

WO 94/04180.

EP 0405980 (Schering corporation) Jan. 1991.

WO 96/01318 (Nycomed Dak) Jan. 1996.

EP 0405980 (Schering corporation) Jan. 1991 (No. 108).

WO 96/01318 (Nycomed Dak) Jan. 1996 (No. 109).

Gesser et al: Interleuki–8 induces its own formation in CD4+ T lymphocytes: a process regulated by Interleukin–10, Biochemical and Biophysical Research Communications, vol. 210, No. 3, May 25, 1995.

N.K.Koostra et al.: "Interference of interleukin–10 with human immunodeficiency virus type 1 replication in primary monocyte–derived macrophages", J. Virology, vol. 68, No. 11, Nov. 1994.

Van Laethem et al.: "Interleukin–10 prevents necrosis in murine experimental acute pancreatitis", pp. 1917–1922, File Medline, abstract 95286011, 1995 XP002029903.

* cited by examiner

```
mIL10    MPGSALLCCLLLLTGMRISRGQYSREDNNCTHFPVGQSHMLLELRTAF
         | |||||| |||| |||  |    ||  ||   ||  ||
hIL10    MHSSALLCCLVLLTGVRASPGQGTQSENSCTHFPGNLPNMLRDLRDAF
                  |||| ||   |     |           | ||||||||
BCRFI    MERRLVVTLQCLVLL--YLAPECGGTD----QCDNFPQ-----MLRDLRDAF
                                                         30 mIL10    SQVKTFFQTKDQLDNILLTDSLMQDFKGYLGCQALSEMIQFYLVEVMPQAEKHGPEIKEHLNSLG
         | |||||| ||| ||| ||   |||||||||||||||||||  |    |  |    | ||||
hIL10    SRVKTFFQMKDQLDNLLLKESLLEDFKGYLGCQALSEMIQFYLEEVMPQAENQDPDIKAHVNSLG
         ||||||||        |||||||||||||||||||||||||| ||||||||   |    ||||
BCRFI    SRVKTFFQTKDEVDNLLLKESLLEDFKGYLGCQALSEMIQFYLEEVMPQAENQDPEAKDHVNSLG
         31                                                            95 mIL10    ENLKTLRMRLRRCHRFLPCENKSKAVEQVKSDFNKLQDQGVYKAMNEFDIFINCIEAYMMIKMKS
         | ||||| || ||||||||||||||||||    ||| | ||||| |||||||| |||||||
hIL10    ENLKTLRLRLRRCHRFLPCENKSKAVEQVKNAFNKLQEKGIYKAMSEFDIFINYIEAYMTMKIRN
         ||||||||||||||||||||||||||||||||||||||||||||||||||||||||||||
BCRFI    ENLKTLRLRLRRCHRFLPCENKSKAVEQIKNAFNKLQEKGIYKAMSEFDIFINYIEAYMTIKAR
         96                                                            160
```

Fig. 1

Comparison of the predicted amino acid sequences of mIL-10, hIL-10, and BCRFI. Amino acid sequence identities are indicated by vertical lines.

COOH TERMINAL PEPTIDE SEQUENCES OF IL-10 INCLUDING
9 AMINO ACIDS OF PORCINE, HUMAN and VIRUS PROTEINS.

| | | | | | | | | | | |
|---|---|---|---|---|---|---|---|---|---|---|
| PORCINE IL-10 | | | | * | | * | | * | | |
| PIT | -A | -Y | -M | -T | -M | -K | -M | -R | -K | -N |
| HUMAN - IL-10 | | | | * | | * | | * | | |
| IT 9302 | -A | -Y | -M | -T | -M | -K | -I | -R | -N | |
| BCRFI IL-10 | | | | * | | * | | * | | |
| VIT | -A | -Y | -M | -T | -I | -K | -A | -R- | | |

Aminoacids marked with * represent key position for receptor binding and are evolutionary well conserved. Compare the IL-10 aminoacid sequence from mouse below.

| | | | | | | | | | |
|---|---|---|---|---|---|---|---|---|---|
| MOUSE IL-10 | | | | | | * | | | |
| MIT | -A | -Y | -M | -M | -I | -K | -M | -K | -S |

This sequence is lacking the homology to the important amino acids.

IT9302 inhibits spontanous IL-8 production by purified cultured monocytes. (▲) Indicates the level of IL-8 when using rh IL-10 (100 ng/ml)

ECL-Western Blotting of CD4+ T cell cytosolic proteins using a goat anti-human IL-4 antibody.

Stimulation for 3 days with:

1. Control  2. mon.anti-IL-8 antibody WS.4  10 µg/ml,
3. rIL-8 100 ng/ml,  4. rIL-10 100 ng/ml,
5. IT9302 10 ng/ml,  6. rIFN gamma 10 ng/ml.

SYNTHETIC IL-10 ANALOGUES

This application is a 371 of PCT/DK97/00021, filed Jan. 16, 1997 (publ. WO97/2679 on Jul. 24, 1997).

FIELD OF THE INVENTION

The present invention relates to the pharmaceutical use of substances which are interleukin 10 (IL-10) agonists. In particular, the invention relates to the use of a substance of the invention for the manufacture of a pharmaceutical composition for the reduction of TNFα production and/or the prophylaxis or treatment of pancreatitis, arthritis urica (gout), allergy of the skin, allergic reactions in the skin, tissue damage as a result of hypoxia/ischemia (infarction, reperfusion), inflammatory reactions due to virus infections, and/or for the manufacture of a conceptive agent.

BACKGROUND OF THE INVENTION

Pharmaceutical compositions comprising hIL-10 or vIL-10, and the use of hIL-10 or vIL-10 for the manufacture of a pharmaceutical composition for the treatment of various conditions have been disclosed in e.g. WO 93/02693 and WO 94/04180, and certain IL-10 agonists have been disclosed in WO 96/01318.

SUMMARY OF THE INVENTION

The present invention relates to the use of a substance or polypeptide according to the formula

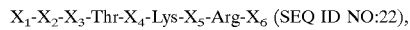

$X_1$-$X_2$-$X_3$-Thr-$X_4$-Lys-$X_5$-Arg-$X_6$ (SEQ ID NO:22), wherein
$X_1$ is Ala or Gly,
$X_2$ is Tyr or Phe,
$X_3$, $X_4$ and $X_5$ are independently selected from the group consisting of Met, Ile, Leu and Val, and
$X_6$ is selected from the group consisting of Asn, Asc, Gln and Glu, optionally at least one of $X_1$, $X_2$, $X_3$, $X_4$, $X_5$ and $X_6$ is independently substituted with non-natural or unusual amino acids and/or the peptide is cyclized and/or the peptide is stabilized and/or the amino terminal amino acid residue is acylated and/or the carboxy terminal amino acid residue is amidated, and peptidomimetics modelled on the basis of the above formula for the preparation of a pharmaceutical composition for the reduction of TNFα production and/or for the prophylaxis or treatment of pancreatitis.

Further, the invention relates to a substance or polypeptide having the formula

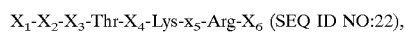

$X_1$-$X_2$-$X_3$-Thr-$X_4$-Lys-$X_5$-Arg-$X_6$ (SEQ ID NO:22), wherein
$X_1$ is Ala or Gly,
$X_2$ is Tyr or Phe,
$X_3$, $X_4$ and $X_5$ are independently selected from the group consisting of Met, Ile, Leu and Val; and
$X_6$ is selected from the group consisting of Asn, Asp, Gln and Glu, wherein at least one of $X_1$, $X_2$, $X_3$, $X_4$, $X_5$ and $X_6$ is independently substituted with non-natural or unusual amino acids and/or the peptide is cyclized and/or the peptide is stabilized and/or the amino terminal amino acid residue is acylated and/or the carbo terminal amino acid residue is amidated, and peptidomimetics modelled on the basis of the above formula, said substance or polypeptide having at least one of the following properties:

a) induces inhibition of spontaneous IL-8 production by human monocyte,
b) induces inhibition of IL-1β induced IL-8 production by human peripheral blood mononuclear cells (PEMC),
c) induces production of interleukin-1 receptor antagonistic protein (IRAP) by human monocytes,
d) induces chemotactic migration of CD8+ human T lymphocytes in-vitro,
e) desensitizes human CD8+T cells resulting in an unresponsiveness towards rhIL-10,
f) suppresses the chemotactic response of CD4+ human T lymphocytes towards IL-8,
g) suppresses the chemotactic response of human monocytes towards MCAF/MCP-1.
h) inhibits class II MHC molecule expression on human monocytes stimulated with IFN-γ,
i) induces the production of IL-4 by cultured normal human CD4+ T cells,
j) reduces the TNFα production in human mixed leukocyte reaction,
k) downregulates TNFα and IL-8 production in a rabbit model of bile acid induced acute pancreatitis and reduces neutrophil infiltration in the lungs of the treated rabbits.

It is contemplated (as described in detail in the following description of immunological mechanisms) that the action mechanism is via interference with the action of mediators of the immune system, in particular cytokines such as monokines, lymphokines, chemokines and monokine-receptor antagonists, i.e. that the substance of the invention interferes with/suppresses the production and/or action of certain cytokines and thus inhibits pathological processes leading to tissue damage, and that the substance of the invention induces the production of natural monokine-receptor antagonists thus interfering with/suppressing the action of certain cytokines such as TNFα or IL-1 and thereby inhibiting pathological processes which lead to tissue damage.

An important embodiment of the present invention thus relates to a pharmaceutical composition comprising, as the active ingredient, a substance of the invention.

In a further aspect, the present invention relates to the use of a substance of the invention for the manufacture of a pharmaceutical composition for substantially inhibiting a biological effect related to a cytokine, i.e. the use of a substance of the invention as an IL-1 receptor antagonist protein/peptide, lymphokine, monokine, interleukin, interferon, chemokine or colony-stimulating factor. Another aspect relates to the use of a substance of the invention for the manufacture of a pharmaceutical composition for the prophylaxis or treatment of a condition related to the disturbance of a cytokine system, i.e. the IL-1 receptor antagonist protein/peptide, lymphokine, monokine, interleukin, interferon, chemokine or colony-stimulating factor system. In another aspect, the invention also relates to a method of treating a condition in a human related to a disturbance in a cytokine system which method comprises administering to the subject an effective amount of a substance of the invention.

The cellular immune system takes part in the development of such disorders as infectious, inflammatory and neoplastic diseases. Immunocompetent cells and their products may play important roles in the initiation, progression and possible chronic nature of development of inflammatory conditions. These disorders are often without known etiology and includes common diseases such as diabetes mellitus, rheumatoid arthritis, inflammatory diseases of the gastrointestinal tract and of the skin. Apart from these examples, cell-mediated immunity or pro-inflammatory mediators, however, contribute to many other inflammatory and proliferative diseases (see Table 1).

TABLE 1

Some diseases where macrophages/T-lymphocyte-mediated immune reactions are considered pathogenetically important Skin diseases:

Psoriasis
Atopic dermatitis
Contact dermatitis
Cutaneous T cell lymphoma (CTCL)
Sezary syndrome
Pemphigus vulgaris
Bullous pemphigoid
Erythema nodosum
Scleroderma
Auto-immune (including rheumatic) diseases:

Uveitis
Bechet's disease
Sarcoidosis Boeck
Sjögren's syndrome
Rheumatoid arthritis
Juvenile arthritis
Reiter's syndrome
Gout
Osteoarthrosis
Systemic lupus erythematosis
Polymyositis
Myocarditis
Primary biliary cirrhosis
Crohn's disease
Ulcerative colitis
Multiple sclerosis and other demyelinating diseases
Aplastic anaemia
Idiopathic thrombocytopenic purpura
Multiple myeloma and B cell lymphoma
Simmons' panhypopituitarism
Graves' disease and Graves' opthalmopathy
Subacute thyreoditis and Hashimoto's disease
Addison's disease
Insulin-dependent diabetes mellitus (type 1)
Other diseases Various clinical syndromes with vasculitis (e.g. polyarteritis nodosa, Wegener's granulomatosis, Giant cell arteritis
Fever, malaise
Anorexia (e.g. in acute and chronic inflammatory and infectious diseases)
Disseminated intravascular coagulation (DIC)
Arteriosclerosis (atherosclerosis)
Shock (e.g. in gram-negative sepsis)
Cachexia (e.g. in cancer, chronic infectious and chronic inflammatory diseases)
Transplant rejection and graft vs. host disease
Prevention of spontaneous abortion XL-10 Activity on Cytokine Production:

hIL-10 inhibits the production of a number of cytokines including interferon-γ(IFN-γ) Tumor Necrosis Factor-α (TNF-α), Granulocyte Macrophage Colony Stimulating Factor (GM-CSF), Granulocyte-CSF (G-CSF), IL-1α, IL-1α, IL-2, IL-6, IL-8 and Monocyte Chemotactic polypeptide-1 (MCP-1/MCAF) by monocytes/macrophages and/or T lymphocytes (4, 5). IL-10 also inhibits the ability of monocytes to migrate as a response to the chemokine MCP-1/MCAF (75). Further, hIL-10 induces the production of an endogenous, natural interleukin-1 receptor antagonist (IRAP) (6), which inhibits IL-1α and IL-1α by competing with receptor binding. Since IL-8 is strongly inducible by IL-1α and by IL-1β, IL-10 exerts part of its inhibitory effect on IL-8 production by stimulating the production of the IL-1-receptor antagonist IRAP. This last mechanism is of considerable importance for the present invention as described and exemplified in the following. IRAP has anti-inflammatory activities (9), and its therapeutic effect in rheumatoid arthritis has been suggested (10). Also, IRAP proved to be effective in the treatment of sepsis syndrome and a dose-dependent, 28-day survival benefit was associated with IRAP treatment (p=0.015) in a study by Fisher et al. (11). IRAP may exert parts of its anti-inflammatory effects by inhibiting chemokine-production such as the production of IL-8.

IL-10 and Antigen Expression:

IL-10 inhibits the expression of class II MHC expression on human monocytes (8). Constitutive and IL-4 or IFN-7 induced expression of HLA-DR/DP and DQ was inhibited by hIL-10 (12). In addition, monocytes pre-incubated with IL-10 are refractory to subsequent induction of class II MHC expression by IL-4 or IFN-γ. IL-10 inhibits class II expression by human monocytes following activation by LPS (12, 76). BALB/c mice given 1 to 10 mg of IL-10 concomitantly with a lethal dose of LPS were protected from death (6).

IL-10 inhibits nitrogen intermediates and superoxide anions. IL-10 also inhibits reactive nitrogen intermediate (NO) as well as reactive oxygen intermediates ($H_2O_2$) by macrophages following activation by IFN-γ (13).

IL-10 and T Cell Activity:

IL-10 has also modulatory effects on T cell functions/activity. Thus, hIL-10 is a potent chemotactic factor to CD8+ T lymphocytes, while hIL-10 does not show chemotaxis towards CD4+ T cells (14). Additionally, IL-10 suppresses the capacity of CD4+ T cells to respond to the chemotactic signals of the β-chemokine RANTES as well as the α-chemokine IL-8. hIL-10 also directly inhibits the proliferation of human peripheral blood T cells and CD4+ T cell clones (14).

Therapeutic Considerations:

These in vivo results/data and other data summarized e.g. in WO 96/01318 strongly suggest a homeostatic role of IL-10 in controlling cell-mediated and monokine-amplified immune inflammation and indicate the wide-ranged therapeutical applications of IL-10 or a drug with IL-10-like activity in the treatment of diseases which are characterized by a decreased/insufficient production and/or activity of IL-10. Tables 1 and 2 list some diseases where an immune-modulator like IL-10 or an immune-modulator with IL-10-like activity is considered to have therapeutic importance:

TABLE 2

Some diseases where an immune-modulator with IL-10-like activity, due to its induction of IRAP production and/or inhibition of cytokine-production and/or activity may have therapeutic importance (ref. 20–74 + 109)

Pre-term labour caused by infection or other conditions
Rheumatoid arthritis
Lyme's arthritis
Gout
Sepsis syndrome
Hyperthermia
Ulcerative colitis or enterocolitis
Osteoporosis
Cytomegalovirus
Periodontal diseases
Glomerulonephritis
Chronic, non-infectious inflammation of the lung (e.g. sarcoidosis and smoker's lung)
Granuloma formation
Fibrosis of the liver
Fibrosis of the lung TABLE 2-continued Some diseases where an immune-modulator with IL-10-like activity, due to its induction of IRAP production and/or inhibition of cytokine-production and/or activity may have therapeutic importance (ref. 20–74 + 109)

Transplant rejection
Graft vs. host disease
Chronic myeloid leukaemia
Acute myeloid leukaemia
Other neoplastic diseases
Asthma bronchiale
Diabetes mellitus, type I (insulin dependent)
Arteriosclerosis/atherosclerosis
Psoriasis
Chronic B lymphocyte leukaemia
Common variable immunodeficiency
Side-effects using other biological response modifiers
Disseminated intravascular coagulation
Systemic sclerosis
Encephalomyelitis
Lung inflammation
Hyper IgE syndrome
Enterocolitis
Cancer metastasis and growth
Adoptive immune therapy
Acquired respiratory distress syndrome
Sepsis
Reperfusion syndrome
Postsurgical inflammation
Organ transplantation
Alopecia
AIDS
Cutaneous HPV-infection

DETAILED DESCRIPTION OF THE INVENTION

Development of an IL-10-Homologous Nonapeptide with IL-10-like Activity:

Partial sequences of hIL-10 having a length of 9 amino acids was chosen according to the principle that the sequences should possess high homology between vIL-10 and hIL-10, but as low homology to mIL-10 as possible. It was found that a synthetic nonapeptide, IT9302, possessed some immuno-suppressive activities which mimic those of hIL-10 as described in further detail in the following examples. IT9302 corresponds to a nonapeptide sequence from the C-terminal end of hIL-10 with the following amino acid sequence:

$NH_2$-Ala-Tyr-Met-Thr-Met-Lys-Ile-Arg-Asn-COOH (SEQ ID NO:1)

The nonapeptide IT9302 is very potent to induce different functions and is very stable, and it is presumed that it cannot be incorrectly coupled to receptors. A nonapeptide has been chosen because generally a 9 amino acid polypeptide sequence is unique for a protein. However, it is to be noted that the 6 amino acids at the very end of hIL-10 seem to be the most important ones. Within the scope of the present invention is thus a substance or polypeptide comprising a sub-sequence of the amino acid sequence Ala-Tyr-Met-Thr-Met-Lys-Ile-Arg-Asn (SEQ ID NO. 1).

It is considered likely that some amino acid substitutions will not have adverse effects on the hIL-10 agonist activity as defined herein as long as the threonine, the lysine and the arginine are present and with one amino acid placed inbetween.

The present invention in particular relates to the use of a substance or polypeptide according to the formula:

$X_1$-$X_2$-$X_3$-Thr —$X_4$-Lys-Xs-Arg-$X_6$ (SEQ ID NO:22), wherein $X_1$ is Ala or Gly, $X_2$ is Tyr or Phe, $X_3$, $X_4$ and Xs are independently selected from the group consisting of Met, Ile, Leu and Val; ard $X_6$ is selected from the group consisting of Asn, Asp, Gln and Glu, optionally at least one of $X_1$, $X_2$, $X_3$, $X_4$, $X_5$ *and* $x_6$ is independently substituted with non-natural or unusual amino acids and/or the peptide is cyclized and/or the peptide is stabilized and/or the amino terminal amino acid residue is acylated and/or the carboxy terminal amino acid residue is amidated, and peptidomimetics modelled on the basis of the above formula for the preparation of a pharmaceutical Composition for the reduction of the IL-1-induced TNFα production presumably by the blocking of the IL-1 receptor with IRAP and/or for the prophylaxis or treatment of pancreatitis.

Examples of specific polypeptides which are presumed to be useful for the reduction of TNFα production and/or the prophylaxis or treatment of pancreatitis are as follows:

1. $NH_2$-Ala-Tyr-Met-Thr-Ile-Lys-Met-Arg-Asn-COOH (SEQ ID NO:2)
2. $NH_2$-Ala-Phe-Met-Thr-Leu-Lys-Leu-Arg-Asn-COOH (SEQ ID NO:3)
3. $NH_2$-Ala-Tyr-Met-Thr-Met-Lys-Val-Arg-Glu-COOH (SEQ ID NO:4)
4. $NH_2$-Gly-Tyr-Met-Thr-Met-Lys-Ile-Arg-Asp-COOH (SEQ ID NO:5)
5. $NH_2$-Ala-Phe-Met-Thr-Met-Lys-Ile-Arg-Asp-COOH (SEQ ID NO:6)
6. $NH_2$-Ala-Tyr-Ile-Thr-Met-Lys-Ile-Arg-Asp-COOH (SEQ ID NO:7)
7. $NH_2$-Ala-Tyr-Leu-Thr-Met-Lys-Ile-Arg-Asp-COOH (SEQ ID NO:8)
8. $NH_2$-Ala-Tyr-Val-Thr-Met-Lys-Ile-Arg-Asp-COOH (SEQ ID NO:9)
9. $NH_2$-Ala-Tyr-Met-Thr-Ile-Lys-Ile-Arg-Asp-COOH (SEQ ID NO:10)
10. $NH_2$-Ala-Tyr-Met-Thr-Leu-Lys-Ile-Arg-Asp-COOH (SEQ ID NO:11)
11. $NH_2$-Ala-Tyr-Met-Thr-Val-Lys-Ile-Arg-Asp-COOH (SEQ. ID NO:12)
12. $NH_2$-Ala-Tyr-Met-Thr-Met-Lys-Ile-Arg-Asp-COOH (SEQ ID NO:13)
13. $NH_2$-Ala-Tyr-Met-Thr-Met-Lys-Met-Arg-Asp-COOH (SEQ ID NO:14)
14. $NH_2$-Ala-Tyr-Met-Thr-Met-Lys-Val-Arg-Asp-COOH (SEQ ID NO:15)
15. $NH_2$-Ala-Tyr-Met-Thr-Met-Lys-Ile-Arg-Gln-COOH (SEQ ID NO:16)
16. $NH_2$-Ala-Tyr-Met-Thr-Met-Lys-Ile-Arg-Glu-COOH (SEQ ID NO:17)

The present invention in particular relates to a polypeptide having the formula

Thr-$X_4$-Lys-$x_4$-Arg-$x_6$ (SEQ ID NO:19), a polypeptide having the formula $X_3$-Thr-$X_4$-Lys-$X_5$-Arg-$X_6$ (SEQ ID NO:20), a polypeptide having the formula $X_2$-$X_3$-Thr-$X_4$-Lys-$X_5$-Arg-$X_6$ (SEQ ID NO:21), and a polypeptide having the formula $X_1$-$x_2$-$x_3$-Thr-$X_4$-Lys-$X_5$-Arg-$X_6$ (SEQ ID NO:22)

wherein

X₁ is Ala or Gly,
X₂ is Tyr or Phe,
X₃, X₄ and X₅ are independently selected from the group consisting of Met, Ile, leu and Val; and
X₆ is selected from the group consisting of Asn, Asp, Gln and Glu, wherein one or more amino acids are substituted with non-natural or unusual amino acids and/or the peptide is cyclized and/or the amino terminal amino acid residue is acylated and/or the carboxy terminal amino acid residue is amidated, and peptidomimetics modelled on the basis of the above formula, said analogues having at least one of the following properties:

a) induces inhibition of spontaneous IL-8 production by human monocytes, b) induces inhibition of IL-1β induced IL-8 production by human peripheral blood mononuclear cells (PBMC)

c) induces production of interleukin-1 receptor antagonistic protein (IRAP) by human monocytes, d) induces chemotactic migration of CD8+ human T lymphocytes in vitro, e) desensitizes human CD8+ T cells resulting in an unresponsiveness towards rhIL-10, f) suppresses the chemotactic response of CD4+ T human lymphocytes towards IL-8, g) suppresses the chemotactic response of human monocytes towards MCAF/MCP-1, h) inhibits class II MHC molecule expression on human monocytes stimulated by IFN-γ, i) induces the production of IL-4 by cultured normal human CD4+T cells, j) reduces the TNFα production in human mixed leukocyte reaction, k) downregulates TNFα and IL-8 production in a rabbit model of bile acid induced acute pancreatitis and reduces neutrophil infiltration in the lungs of the treated rabbits. By use of the term "at least one biological activity of IT9302" in the present specification and claims, reference is meant to be to at least one of the above mentioned properties.

Any of the contemplated peptides of the invention can have an amino terminal amino acid residue which is acylated such as acetylated or benzoylated. Also, any of the contemplated peptides can have a carboxy terminal amino acid residue which is amidated.

The present invention further contemplates analogues of peptides formed by other conservative amino acid substitutions than the specific substitutions proposed above, substitutions of unusual or non-natural amino acids, stabilization of peptides, cyclization of peptides, and peptidomimetics modelled on the identified IL-10 agonist peptides.

The principle behind conservative amino acid substitution is that certain amino acid pairs have compatible side chains such that, when one is substituted for the other, there will be only minimal changes in the tertiary structure and the binding affinity of the peptide. Rules for conservative substitution are explained in (78).

"Conservative" as used herein means (i) that the alterations are as conformationally neutral as possible, that is, designed to produce minimal changes in the tertiary structure of the mutant polypeptides as compared to the native protein, and (ii) that the alterations are as antigenically neutral as possible, that is designed to produce minimal changes in the antigenic determinants of the mutant polypeptides as compared to the native protein. Conformational neutrality is desirable for preserving biological activity, and antigenic neutrality is desirable for avoiding the triggering of immunogenic responses in patients or animals treated with the substances of the invention. Although it is difficult to select with absolute certainty which alternatives will be conformationally and antigenically neutral, rules exist which can guide those skilled in the art to make alterations that have high probabilities of being conformationally and antigenically neutral, see e.g. (77) and (78). Some of the more important rules include (1) replacement of hydrophobic residues is less likely to produce changes in antigenicity because they are likely to be located in the protein's interior, e.g. Berzofsky (cited above) and Bowie et al. (cited above); (2) replacement of physicochemically similar, i.e. synonymous, residues is less likely to produce conformational changes because the replacing amino acid can play the same structural role as the replaced amino acid; and (3) alteration of evolutionarily conserved sequences is likely to produce deleterious conformational effects because evolutionary conservation suggests sequences may be functionally important. In addition to such basic rules for selecting mutein sequences, assays are available to confirm the biological activity and conformation of the engineered molecules. Changes in conformation can be tested by at least two well known assays: the microcomplement fixation method, e.g. (79) and (80) used widely in evolutionary studies of the tertiary structures of proteins; and affinities to sets of conformation-specific monoclonal antibodies, e.g. (81). Biological assays for the substances of the invention are described more fully in the examples:

Inhibition of spontaneous IL-8 production by human monocytes is tested as outlined in Example 1 using the synthesized substance or peptide instead of IT9302. If the IL-8 production is suppressed to be no more than 50% when 1 ng/ml of the substance or peptide is used, then the substance or peptide is within the scope of the present invention. Inhibition of IL-1β induced IL-8 production by human peripheral blood mononuclear cells (PBMC) is tested as outlined in Example 2 using the synthesized substance or peptide instead of IT9302. If the percent inhibition of IL-8 production is at least 50% when 1 ng/ml of the substance or peptide is used, then the substance or peptide is within the scope of the present invention.

Production of interleukin-1 receptor antagonistic protein (IRAP) by human monocytes is tested as outlined in Example 3 using the synthesized substance or peptide instead of IT9302. If the induction of IRAP is at least 30 ng/ml when 10 ng/ml of the substance or peptide is used, then the substance or peptide is within the scope of the present invention.

Induction of chemotactic migration of CD8+ human T lymphocytes in vitro is tested as outlined in Example 4 using the synthesized substance or peptide instead of IT9302. If the potency of the substance or peptide when a concentration of 10 ng/ml is used is present, i.e. 2 or more, then the substance or peptide is within the scope of the present invention.

Desensitization of human CD8+ T cells resulting in an unresponsiveness towards rhIL-10 is tested as outlined in Example using the synthesized substance or peptide instead of IT9302. If preincubation of cells with the substance or peptide results in a substantially totally suppressed responsiveness of the CD8+ cells towards hrIL-10, i.e. giving a value of about 1, such as 0.8 to 1.2, at a concentration of the substance or peptide of 10 ng/ml, then the substance or peptide is within the scope of the present invention.

Suppression of the chemotactic response of CD4+ human T lymphocytes towards IL-8 is tested as outlined in Example 6 using the synthesized substance or peptide instead of IT9302. If addition of the substance or peptide to a suspension of human CD4+ T lymphocytes results in a substantially total inhibition of the response of the CD4+ cells towards IL-8, i.e. giving a value of about 1, such as 0.8 to 1.2, at a concentration of the substance or peptide of 10 ng/ml, then the substance or peptide is within the scope of the present invention.

Suppression of the chemotactic response of human monocytes towards MCAF/MCP-1 is tested as outlined in Example 7 using the synthesized substance or peptide instead of IT9302. If addition of the substance or peptide to a suspension of human monocytes results in a substantially total inhibition of the chemotactic response of the monocytes towards MCAF/MCP-1, i.e. giving a value of about 1, such as 0.8 to 1.2, at a concentration of the substance or peptide of 10 ng/ml, then the substance or peptide is within the scope of the present invention.

Inhibition of class II MHC molecule expression on human monocytes stimulated with IFN-γ is tested as outlined in Example 8 using the synthesized substance or peptide instead of IT9302. IFN-γ upregulated MHC II antigen expression in the cell population from 36.8% to 58.4%, and this stimulation was blocked or downregulated to 25.2% by 10 ng/ml rhIL-10 and to 31.2% by 1 ng/ml IT9302 (FIG. 12). If a substance or peptide blocks or downregulates class II MHC expression on monocytes to the unstimulated level, when added in an amount of 1–10 ng/ml, then the substance or peptide is within the scope of the present invention.

If addition of the substance or peptide is capable of blocking the effect of the IPNγ stimulation at a concentration of the substance or peptide of 10 ng/ml, then the substance or peptide is within the scope of the present invention.

Induction of the production of IL-4 by cultured normal human CD4+ T cells is tested as outlined in Example 9 using the synthesized substance or peptide instead of IT9302. If addition of the substance or peptide induces the production of IL-4 in CD4+ T lymphocytes at a concentration of the substance or peptide of 10 ng/ml, then the substance or peptide is within the scope of the present invention.

Reduction of the TNFα production in human mixed leukocyte reaction is tested as outlined in Example 10 using the synthesized substance or peptide instead of IT9302. If addition of the substance or peptide significantly reduces the production of TNFα in human mixed leukocyte reaction within 24 hours at a concentration of the substance or peptide of 10 ng/ml, then the substance or peptide is within the scope of the present invention.

Downregulation of TNFα and IL-8 production in a rabbit model of bile acid induced acute pancreatitis and reduction of neutrophil infiltration in the lungs of the treated rabbits is tested as outlined in Example 14 using the synthesized substance or peptide instead of IT9302. If addition of the substance or peptide significantly reduces the mortality of the test animals, when the substance or peptide is added at a concentration of 100 μg/kg, then the substance or peptide is within the scope of the present invention.

An important embodiment of the present invention thus relates to a polypeptide in which at least one amino acid residue has been substituted with a different amino acid residue and/or in which at least one amino acid residue has been deleted or added so as to result in a polypeptide comprising an amino acid sequence being different from the amino acid sequence or a subsequence of said amino acid sequence as defined in the following, but essentially having hIL-10 agonist activity as defined above.

Analogues of synthetic peptides can also be made by substituting individual residues with non-natural or unusual amino acids. Sequences of bioactive peptides are originally derived from proteins which are made up of the naturally occurring twenty L-amino acid residues. However, the process of chemical synthesis used to construct synthetic peptides allows for the substitution of alternate residues including D-.amino acids, β-amino acids, N-substituted amino acids, infrequently occurring natural amino acids, or non-natural synthetic amino acid analogues (93). Non-limiting examples of amino acids useful in the present invention are:

| | |
|---|---|
| Aad | 2-Aminoadipic acid |
| bAad | 3-Aminoadipic acid |
| bAla | beta-Alanine, beta-Aminopropionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| bAib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| aHyl | allo-Hydroxylysine |
| 3Hyp | 3-Hydroxyproline |
| 4Hyp | 4-Hydroxyproline |
| Ide | Isodesmosine |
| aIle | allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

Further and non-limiting examples of infrequently occurring, non-natural amino acids or building blocks are listed as follows: Novabiochem 1994/95 Catalog (Calbiochem-Novabiochem AG, Weidenmattweg 4, CH-4448 Läufelfingen/Switzerland), pp. 65–125; Bachem Feinkemikalien AG 1995 Catalog (Bachem Feinkemikalien AG, Hauptstrasse 144, CH-4416 Bubendoft/Switzerland), pp. 753–831; Neosystem Laboratoire Catalogue 1997/98 (Neosystem Laboratoire, 7 rue de Boulogne, 67100 Strasbourg, France), pp. 131–176.

REFERENCE TABLE A aliphatic

| | | |
|---|---|---|
| 04-10-0002 | H-D-Ala-OH | Novabiochem |
| 04-10-0004 | H-βAla-OH | Novabiochem |
| 04-11-0050 | C-All-L-Ala | Novabiochem |
| 04-12-9001 | H-MeAla-OH | Novabiochem |
| 04-13-9005 | H-D-MeAla-OH | Novabiochem |
| 04-12-8000 | Ac-Ala-OH | Novabiochem |
| 04-13-8000 | Ac-D-Ala-OH | Novabiochem |
| 04-12-8001 | Ac-βAla-OH | Novabiochem |
| 04-12-5039 | Benzoyl-Ala-OH | Novabiochem |
| 04-13-5003 | Benzoyl-D-Ala-OH | Novabiochem |
| 04-12-0510 | Z-Ala-OH | Novabiochem |
| 04-13-0500 | Z-D-Ala-OH | Novabiochem |
| 04-12-0532 | Z-βAla-OH | Novabiochem |
| 04-13-9000 | Z-D-MeAla-OH | Novabiochem |
| 04-12-9003 | Z-MeAla-OH | Novabiochem |
| 05-22-2506 | For-Ala-OH | Novabiochem |

REFERENCE TABLE A -continued

| | | |
|---|---|---|
| 04-12-5225 | p-Nitrobenzoyl-βAla-OH | Novabiochem |
| 04-11-0021 | H-Abu-OH | Novabiochem |
| 04-11-0046 | H-γ-Abu-OH | Novabiochem |
| 04-12-0533 | Z-Abu-OH | Novabiochem |
| 04-12-0629 | Z-γ-Abu-OH | Novabiochem |
| 04-11-0044 | H-εAhx-OH | Novabiochem |
| 04-12-0534 | Z-εAhx-OH | Novabiochem |
| 04-11-0047 | H-Aib-OH | Novabiochem |
| 04-11-0016 | L-β-t-Butylglycine | Novabiochem |
| 04-11-0017 | D-β-t-Butylglycine | Novabiochem |
| 04-11-0060 | H-L-Cit-OH | Novabiochem |
| 04-11-0035 | H-D-Cha-OH | Novabiochem |
| 04-11-0049 | C-All-L-Gly | Novabiochem |
| 04-12-8006 | Ac-Gly-OH | Novabiochem |
| 04-12-0509 | Z-Gly-OH | Novabiochem |
| 04-15-0002 | Cap-Gly-OH | Novabiochem |
| 04-15-0003 | Lau-Gly-OH | Novabiochem |
| 04-15-0001 | Myr-Gly-OH | Novabiochem |
| 04-15-0004 | Pal-Gly-OH | Novabiochem |
| 04-12-5233 | N-Phenyl-Gly-OH | Novabiochem |
| 04-15-0005 | Ste-Gly-OH | Novabiochem |
| 04-12-5237 | Trt-Gly-OH | Novabiochem |
| 04-10-0018 | H-His-OH | Novabiochem |
| 04-10-0059 | H-D-His-OH | Novabiochem |
| 04-10-0020 | H-Hyp-OH | Novabiochem |
| 04-12-9004 | H-MeIle-OH | Novabiochem |
| 04-12-8010 | Ac-Ile-OH | Novabiochem |
| 04-12-0522 | Z-Ile-OH (oil) | Novabiochem |
| 05-22-2507 | For-Ile-OH | Novabiochem |
| 04-12-9000 | Z-MeIle-OH | Novabiochem |
| 04-10-0056 | H-D-Leu-OH | Novabiochem |
| 04-12-9006 | H-MeLeu-OH | Novabiochem |
| 04-11-0067 | H-Leu(γMe)-OH | Novabiochem |
| 04-12-8012 | Ac-Leu-OH | Novabiochem |
| 04-13-8002 | Ac-D-Leu-OH | Novabiochem |
| 04-12-0501 | Z-Leu-OH (oil) | Novabiochem |
| 04-13-0512 | Z-D-Leu-OH (oil) | Novabiochem |
| 04-12-9008 | Z-MeLeu-OH | Novabiochem |
| 04-10-0028 | H-D-Met-OH | Novabiochem |
| 04-11-0061 | H-Met(O)-OH | Novabiochem |
| 04-11-0019 | H-Nle-OH | Novabiochem |
| 04-11-0041 | H-D-Nle-OH | Novabiochem |
| 04-11-0020 | H-Nva-OH | Novabiochem |
| 04-11-0042 | H-D-Nva-OH | Novabiochem |
| 04-11-0031 | H—Pen—OH | Novabiochem |
| 04-11-0032 | H-D-Pen—OH | Novabiochem |
| 04-10-0036 | H-Pro-OH | Novabiochem |
| 04-10-0037 | H-D-Pro-OH | Novabiochem |
| 04-11-0008 | Thioproline | Novabiochem |
| 04-11-0062 | H-Sar-OH | Novabiochem |
| 04-12-0581 | Z-Sar-OH | Novabiochem |
| 04-11-0015 | Statine | Novabiochem |
| 04-11-0059 | ACHPA | Novabiochem |
| 04-11-0058 | AHPPA | Novabiochem |
| 04-12-5262 | H-Thr-(Bzl)-OH | Novabiochem |
| 04-12-5003 | H-Thr-(tBu)-OH | Novabiochem |
| 04-12-0589 | Z-Thr(Bzl)-OH | Novabiochem |
| 04-12-0502 | Z-Thr(tBu)-OH.DCHA | Novabiochem |
| 04-10-0049 | H-D-Val-OH | Novabiochem |
| 04-11-0051 | H-D-Val(βOH)-OH | Novabiochem |
| 04-12-9017 | H-MeVal-OH | Novabiochem |
| 04-13-9009 | H-D-MeVal-OH.HCl | Novabiochem |
| 04-12-8029 | Ac-Val-OH | Novabiochem |
| 04-13-8011 | Ac-D-Val-OH | Novabiochem |
| 04-12-0507 | Z-Val-OH | Novabiochem |
| 04-13-0523 | Z-D-Val-OH | Novabiochem |
| 04-12-9019 | Z-MeVal-OH | Novabiochem |
| 04-11-0003 | L-Carnitine | Novabiochem |
| F-2740 | L-alfa-aminosuberic acid | Bachem |
| F-1425 | H-β-Chlora-Ala-OH | Bachem |
| F-1460 | H-β-Cyana-Ala-OH | Bachem |
| F-2500 | H-β-Cyclohexyl-Ala-OH.HCl | Bachem |
| F-2505 | H-β-Cyclohexyl-D-Ala-OH.HCl | Bachem |
| F-1470 | H-β-(1-Cyclopentenyl)-DL-Ala-OH | Bachem |
| F-1465 | H-β-Cyclopentyl-DL-Ala-OH | Bachem |
| F-1475 | L-Cycloserine | Bachem |
| F-1480 | D-Cycloserine | Bachem |
| F-2985 | H-4,5-Dehydro-Leu-OH | Bachem |
| F-1490 | H-3,4-Dehydro-Pro-OH | Bachem |
| F-1160 | H-allo-Ile-OH | Bachem |
| F-1165 | H-D-allo-Ile-OH | Bachem |
| F-1175 | H-allo-Thr-OH | Bachem |
| F-1180 | H-D-allo-Thr-OH | Bachem |
| F-2540 | H-allo-Thr(tBu)-OH | Bachem |
| F-1205 | 7-Aminoheptanoic acid | Bachem |
| F-1281 | L-Axetidine-3-carboxylic acid | Bachem |
| F-2285 | Azetidine-3-carboxylic acid | Bachem |
| F-2395 | H-α-Difluoro-Me-DL-Orn-OH | Bachem |
| F-2530 | H-β-Fluora-DL-Ala-OH | Bachem |
| B-1910 | Fmoc-γ-Abu-OH | Bachem |
| F-2780 | H-Homoarg-OH | Bachem |
| F-1625 | H-Homopro-OH | Bachem |
| F-1630 | H-D-Homopro-OH | Bachem |
| F-1765 | N—Me-Aib-OH | Bachem |
| F-1800 | H-α-Me-DL-Leu-OH | Bachem |
| F-2895 | H-Met($O_2$)-OH | Bachem |
| F-2550 | Myristoyl-Gly-OH | Bachem |
| F-1315 | H-Neopentylgly-OH | Bachem |
| F-1320 | H-D-Neopentylgly-OH | Bachem |
| F-2040 | H-Propargyl-Gly-OH | Bachem |
| F-2900 | H-D-Propargyl-Gly-OH | Bachem |
| C-1535 | Z-dehydro-Ala-OH | Bachem |
| FA02901 | Fmoc-D-2-aminobutyric acid | Neosystem |
| AA03001 | H-4-aminobutyric acid | Neosystem |
| AA03201 | H-8-aminocaprylic acid | Neosystem |
| FA03301 | Fmoc-1-amino-1-cyclohexane carboxylic acid | Neosystem |
| FA12101 | Fmoc-(3S,4S,5S)-4-amino-3-hydroxy-5-methyl-heptanoic acid | Neosystem |
| BA03804 | Boc-(3S,4S)-4-amino-3-hydroxy-5-(4-benzyloxyphenyl)-pentanoic acid | Neosystem |
| FA03103 | Fmoc-(3S,4S)-4-amino-3-hydroxy-6-methylthio-hexanoic acid | Neosystem |
| AA03601 | H-2-aminoisobutyric acid | Neosystem |
| AA05201 | H-D-2-aminovaleric acid | Neosystem |
| AA05202 | H-L-2-aminovaleric acid | Neosystem |
| FA03801 | Fmoc-5-aminovaleric acid | Neosystem |
| FA04102 | Fmoc-L-α-t-butylglycine | Neosystem |
| FA09401 | Fmoc-(4-carboxymethyl)-piperidine | Neosystem |
| FA11701 | (R,S)-Fmoc-2-carboxymorpholine | Neosystem |
| FA02301 | Fmoc-β-cyclohexyl-D-alanine | Neosystem |
| FA02302 | Fmoc-β-cyclohexyl-L-alanine | Neosystem |
| FA11901 | Fmoc-D-homoleucine | Neosystem |
| FA11902 | Fmoc-L-homoleucine | Neosystem |
| AA04802 | H-L-hydroxyproline | Neosystem |
| FA04804 | Fmoc-O-t-butyl-L-hydroxyproline | Neosystem |
| FA09001 | Fmoc-isonipecotic acid | Neosystem |
| FA01220 | Fmoc-L-Lys(Biotin)-OH | Neosystem |
| AA05101 | H-D-norleucine | Neosystem |
| AA05102 | H-L-norleucine | Neosystem |
| AA05201 | H-D-norvaline | Neosystem |
| AA05202 | H-L-norvaline | Neosystem |
| AA08602 | H-L-ornithine.HCl | Neosystem |
| AA00811 | H-sarcosine | Neosystem |
| FA08901 | Fmoc-statine | Neosystem |
| FA06502 | Fmoc-L-thiazolidine-4-carboxylic acid | Neosystem |
| FA09701 | Fmoc-tranexamic acid | Neosystem |
| FB02301 | (3S)-Fmoc-3-amino-1-carboxymethyl-caprolactame | Neosystem |
| FB02801 | (2S,6S,9S)-Fmoc-6-amino-2-carboxymethyl-3,8-diazabicyclo-[4,3,0]-nonane-1,4-dione | Neosystem |
| FB02601 | Fmoc-BTD | Neosystem |
| FB02101 | Fmoc-"Freidinger's lactame" | Neosystem |
| BB01502 | Boc-Pro-ψ[$CH_2$N(2-Cl—Z)]-Gly-OH | Neosystem | aromatic

| | | |
|---|---|---|
| 04-11-0066 | H-Nal-OH | Novabiochem |
| 04-11-0001 | H-D-Nal-OH | Novabiochem |
| 04-10-0032 | H-D-Phe-OH | Novabiochem |
| 04-11-0054 | H-Phe(pCl)-OH | Novabiochem |
| 04-11-0048 | H-D-Phe(pCl)-OH | Novabiochem |
| 04-11-0024 | H-Phe(2F)-OH | Novabiochem |
| 04-11-0025 | H-Phe(3F)-OH | Novabiochem |

REFERENCE TABLE A

| | | |
|---|---|---|
| 04-11-0026 | H-Phe(pF)-OH | Novabiochem |
| 04-12-7500 | H-α-Me-Phe-OH | Novabiochem |
| 04-12-9009 | H-MePhe-OH | Novabiochem |
| 04-13-9007 | H-D-MePhe-OH.HCl | Novabiochem |
| 04-11-0045 | H-Phe(NO$_2$)-OH.H$_2$O | Novabiochem |
| 04-12-8018 | Ac-Phe-OH | Novabiochem |
| 04-13-8005 | Ac-D-Phe-OH | Novabiochem |
| 04-12-5139 | Benzoyl-Phe-OH | Novabiochem |
| 04-13-5031 | Benzoyl-D-Phe-OH | Novabiochem |
| 04-12-0500 | Z-Phe-OH | Novabiochem |
| 04-13-0516 | Z-D-Phe-OH | Novabiochem |
| 04-12-9021 | Z-MePhe-OH | Novabiochem |
| 04-10-0034 | H-Phg-OH | Novabiochem |
| 04-10-0035 | H-D-Phg-OH | Novabiochem |
| 04-11-0029 | D-(−)-Dihydrophenylglycine | Novabiochem |
| 04-12-0575 | Z-Phg-OH | Novabiochem |
| 04-11-0062 | H-Tic-OH | Novabiochem |
| 04-11-0063 | H-Tic(OH)-OH.2H$_2$O | Novabiochem |
| 04-11-0036 | H-Thi-OH | Novabiochem |
| 04-10-0043 | H-Trp-OH | Novabiochem |
| 04-10-0044 | H-D-Trp-OH | Novabiochem |
| 04-11-0038 | 5-Hydroxy-L-Trp-OH | Novabiochem |
| 04-12-5186 | H-Trp(Boc)-OH | Novabiochem |
| 04-13-5066 | H-D-Trp(Boc)-OH | Novabiochem |
| 04-10-0047 | H-D-Tyr-OH | Novabiochem |
| 04-11-0014 | H-Tyr(3',5'-di-I)-OH | Novabiochem |
| 04-12-5013 | H-Tyr(Bzl)-OH | Novabiochem |
| 04-12-5012 | H-Tyr(tBu)-OH | Novabiochem |
| 04-13-5056 | H-D-Tyr(tBu)-OH | Novabiochem |
| F-1305 | H-p-Bromo-Phs-OH | Bachem |
| F-2800 | H-p-Bz-Phe-OH | Bachem |
| F-2810 | H-p-Bz-D-Phe-OH | Bachem |
| F-1445 | H-p-Chloro-Phe-OH | Bachem |
| F-2520 | H-p-Chloro-D-Phe-OH | Bachem |
| F-1200 | H-4-Amino-3,5-diiodo-Phe-OH | Bachem |
| F-1225 | H-p-Amino-Phe-OH.HCl | Bachem |
| F-2855 | H-p-Amino-D-Phe-OH.HCl | Bachem |
| F-2490 | H-β-(3-Benzothienyl)-Ala-OH | Bachem |
| F-2485 | H-β-(3-Benzothienyl)-D-Ala-OH | Bachem |
| F-1520 | H-3,5-Dibromo-Tyr-OH | Bachem |
| F-2225 | H-3,5-Diiodo-Tyr-OH | Bachem |
| F-3005 | H-3,5-Diiodo-D-Tyr-OH | Bachem |
| F-1530 | H-p-Fluoro-Phe-OH | Bachem |
| F-2320 | H-p-Fluoro-D-Phe-OH | Bachem |
| F-2135 | H-m-Flouro-DL-Phe-OH | Bachem |
| B-2360 | Fmoc-p-azido-Phe-OH | Bachem |
| B-2220 | Fmoc-p-Bz-Phe-OH | Bachem |
| F-1610 | H-Homophe-OH | Bachem |
| F-1615 | H-D-Homophe-OH | Bachem |
| F-1670 | H-p-iodo-D-Phe-OH | Bachem |
| F-1675 | H-p-iodo-DL-Phe-OH | Bachem |
| E-3150 | H-α-Me-Phe-OH | Bachem |
| F-3115 | H-α-Me-D-Phe-OH | Bachem |
| F-1810 | H-α-Me-DL-Trp-OH | Bachem |
| F-2820 | H-β-(2-Pyridyl)-Ala-OH | Bachem |
| F-2790 | H-β-(2-Pyridyl)-D-Ala-OH | Bachem |
| FA02601 | Fmoc-2-aminobenzoic acid | Neosystem |
| FA02801 | Fmoc-4-aminobenzoic acid | Neosystem |
| FA12401 | Fmoc-3-amino-1-carboxymethyl-pyridin-2-one | Neosystem |
| BA03805 | Boc-(3S,4S)-4-amino-3-hydroxy-5-(3-indolyl)-pentanoic acid | Neosystem |
| BA03701 | Boc-(3S,4S)-4-amino-3-hydroxy-5-phenyl-pentanoic acid | Neosystem |
| FA08801 | Fmoc-2-aminoindane-2-carboxylic acid | Neosystem |
| FA02702 | Fmoc-(3-aminomethyl)-benzoic acid | Neosystem |
| FA09201 | Fmoc-(D,L)-2-aminotetraline-2-carboxylic acid | Neosystem |
| FA01406 | Fmoc-4-bromo-D-phenylalanine | Neosystem |
| FA01407 | Fmoc-4-bromo-L-phenylalanine | Neosystem |
| FA05602 | Fmoc-4-chloro-L-phenylalanine | Neosystem |
| FA05701 | Fmoc-3,4-dichloro-D-phenylalanine | Neosystem |
| FA05702 | Fmoc-3,4-dichloro-L-phenylalanine | Neosystem |
| FA11801 | (R,S)-Fmoc-1,3-dihydro-2H-isoindole carboxylic acid | Neosystem |
| FA05801 | Fmoc-4-fluoro-D-phenylalanine | Neosystem |
| FA05802 | Fmoc-4-fluoro-L-phenylalanine | Neosystem |
| FA05002 | Fmoc-L-indoline-2-carboxylic acid | Neosystem |
| FA01221 | Fmoc-L-Lys(Dabcyl)-OH | Neosystem |
| FA01410 | Fmoc-4-methyl-D-phenylalanine | Neosystem |
| FA01411 | Fmoc-4-methyl-L-phenylalanine | Neosystem |
| FA02506 | Fmoc-D-1-naphthylalanine | Neosystem |
| FA02505 | Fmoc-L-1-naphthylalanine | Neosystem |
| FA02503 | Fmoc-D-2-naphthylalanine | Neosystem |
| FA02504 | Fmoc-L-2-naphthylalanine | Neosystem |
| FA06001 | Fmoc-4-nitro-D-phenylalanine | Neosystem |
| FA06002 | Fmoc-4-nitro-L-phenylalanine | Neosystem |
| FA07102 | Fmoc-3-nitro-L-tyrosine | Neosystem |
| FA09801 | Racemic Fmoc-trans-3-phenylazetidine-2-carboxylic acid | Neosystem |
| FA08001 | Fmoc-D-3-pyridylalinine | Neosystem |
| FA08002 | Fmoc-L-3-pyridylalanine | Neosystem |
| FA09501 | Fmoc-D-tetrahydroisoquinoline-2-carboxylic acid | Neosystem |
| FA09502 | Fmoc-L-tetrahydroisoquinoline-2-carboxylic acid | Neosystem |
| AA06601 | 1,2,3,4-D-tetrahydroisoquinoline-3-carboxylic acid | Neosystem |
| AA06602 | 1,2,3,4-L-tetrahydroisoquinoline-3-carboxylic acid | Neosystem |
| FA12501 | Fmoc-L-1,2,3,4-tetrahydronorharman-3-carboxylic acid | Neosystem |
| FA02501 | Fmoc-β-(2-thienyl)-D-alanine | Neosystem |
| FA02502 | Fmoc-β-(2-thienyl)-L-alanine | Neosystem |
| FB02201 | (R,S)-Fmoc-3-amino-N-1-carboxymethyl-2-oxo-5-phenyl-1,4-benzodiazepine | Neosystem |
| FB02401 | (R,S)-Fmoc-3-amino-1-carboxymethyl-2,3,4,5-tetrahydro-1H-[1]-benzazepine-2-one | Neosystem |
| FB02501 | Fmoc-3-(2-aminoethyl)-1-carboxymethyl-quinazoline-2,4-dione | Neosystem |
| FB02701 | (2S,5S)-Fmoc-5-amino-1,2,4,5,6,7-hexahydro-azepino [3,2,1-hi] indole-4-one-2-carboxylic acid | Neosystem | basic

| | | |
|---|---|---|
| 04-11-9024 | H-Arg(OH)-OH.AcOH | Novabiochem |
| 04-11-9022 | H-Arg(Me)-OH.AcOH | Novabiochem |
| 04-11-9023 | H-D-Arg(Me)-OH.AcOH | Novabiochem |
| 04-10-0060 | H-D-Lys-OH | Novabiochem |
| 04-10-0030 | H-Orn-OH.HCl | Novabiochem |
| 04-10-0066 | H-D-Orn-OH.HCl | Novabiochem |
| F-3050 | L-α,γ-Diaminobutyric acid.2HCl | Bachem |
| F-3055 | D-α,γ-Diaminobutyric acid.2HCl | Bachem |
| F-1505 | 2,6-Diaminopimelic acid (LL, DD and meso) | Bachem |
| F-3040 | L-α,β-Diaminopropionic acid.HCl | Bachem |
| F-3045 | D-α,β-Diaminopropionic acid.HCl | Bachem |
| FA12001 | Fmoc-4-(2-aminoethyl)-1-carboxymethyl-piperazine dihydrochloride | Neosystem |
| FA09301 | N,N-bis(N'-Fmoc-3-aminopropyl)-glycine potassium hemisulfate | Neosystem |
| FA11601 | Fmoc-4-carboxymethyl-piperazine | Neosystem |
| FA00804 | N-α-Fmoc-N-α'-Boc-diaminoacetic acid | Neosystem |
| BA03904 | N-α-Boc-N-γ-Fmoc-L-diaminobutyric acid | Neosystem |
| FA03904 | N-α-Fmoc-N-γ-Boc-L-diaminobutyric acid | Neosystem |
| BA04005 | N-α-Boc-N-β-Fmoc-D-diaminopropionic acid | Neosystem |
| BA04006 | N-α-Boc-N-β-Fmoc-L-diaminopropionic acid | Neosystem |
| FA04004 | N-α-Fmoc-N-β-Boc-L-diaminopropionic acid | Neosystem |
| BB01102 | Boc-Leu-ψ(CH$_2$NH)-Phe-OH | Neosystem |
| BB01401 | Boc-Phe-ψ(CH$_2$NH)-Phe-OH | Neosystem |
| BB01501 | Boc-Pro-ψ(CH$_2$NH)-Gly-OH | Neosystem | acidic/amide

| | | |
|---|---|---|
| 04-11-0070 | H-Asu-OH.HCl | Novabiochem |
| 04-10-0009 | H-D-Asn-OH.H$_2$O | Novabiochem |
| 04-10-0011 | H-D-Asp-OH | Novabiochem |
| 04-10-0016 | H-D-Glu-OH | Novabiochem |
| 04-10-0058 | H-D-Gln-OH | Novabiochem |

-continued

| REFERENCE TABLE A | | |
|---|---|---|
| 04-12-5261 | H-Lys(Ac)-OH | Novabiochem |
| 04-12-5117 | H-Lys(Boc)-OH | Novabiochem |
| 04-12-5022 | H-Lys(Z)-OH | Novabiochem |
| 04-13-5052 | H-D-Lys(Z)-OH | Novabiochem |
| 04-12-5245 | H-Lys(Tfa)-OH | Novabiochem |
| 04-12-5283 | H-Orn(Boc)-OH | Novabiochem |
| 04-13-5021 | H-D-Orn(Boc)-OH | Novabiochem |
| 04-12-5134 | H-Orn(Z)-OH | Novabiochem |
| F-2560 | L-α-Aminoadipic acid | Bachem |
| F-2575 | D-α-Aminoadipic acid | Bachem |
| F-3150 | L-α-Aminoadipic acid-δ-t-butylester | Bachem |
| F-2030 | H-Ser($PO_3H_2$)-OH | Bachem |
| F-2035 | H-D-Ser($PO_3H_2$)-OH | Bachem |
| FA04008 | N-α-Fmoc-N-β-Z-L-diaminopropionic acid | Neosystem |
| ZA04006 | N-α-Z-N-β-Fmoc-L-diaminopropionic acid | Neosystem |
| FB01501 | Fmoc-(S,S)-[Pro-Leu]-spirolactame | Neosystem |

The above described alternate residues can be used (a) to replace chemically reactive residues and improve the stability of the synthetic peptide towards e.g. enzymatic and proteolytic degradation, (b) to provide analytic labels useful in the detection of the synthetic peptide, and (c) to modulate the bioactivity of the synthetic peptide by increasing or decreasing the binding affinity of the peptide for the IL-10 receptor, e.g. by introduction of conformational constraints which reduce the rotational freedom for specific chemical bonds.

Within the scope of the present invention are further substances wherein one or more of the residues Thr, Lys or Arg in the above formula is substituted with non-natural or unusual amino acids as proposed above. All polypeptide sequences in the present specification and claims are, also when not explicitly stated, written from the N-terminal to the C-terminal end in the conventional format.

The method of choice for synthesis of the peptides and their analogues is solid-phase peptide synthesis (SPPS). This method was introduced by Merrifield (100) in 1963, and numerous peptides have been synthesized since then with this technique. An excellent review of the current chemical synthesis of peptides and proteins is given by S. B. H. Kent (101).

In practice, peptides are assembled by stepwise SPPS. The C-terminal amino acid in the form of an N-alfa-protected, if necessary side chain-protected reactive derivative, is covalently coupled either directly or by means of a suitable linker to a solid support, e.g. a polymeric resin, which is swollen in an organic solvent. The N-alfa-protective group is then removed and the succeeding protected amino acids according to the desired sequence are added in a stepwise manner.

After assembly of the complete peptide chain, the side chain-protective groups are removed, and the peptide is cleaved from the resin, which may be done simultaneously or in separate steps.

Among the several different coupling strategies which have emerged over the years, two are currently in general use, based on the different N-alfa-protective groups and matching side chain-protective groups. Merrifield used tert.butyloxy-carbonyl (Boc) as the N-alfa-protective group, while 9-fluorenylmethoxycarbonyl (Fmoc) was introduced by Carpino and Han (102). The practical application of these two strategies including the choice of solid supports, side chain-protecting groups, activation procedures, cleavage procedures, instrumentation, and analytical and monitoring techniques have been given in several monographs among which should be mentioned the following: Stewart and Young (103), Atherton and Sheppard (104), and Pennington and Dunn (105). Peptides and their analogues with unusual or non-natural amino acids in the present invention are conveniently synthesized according to these protocols.

Analogues of synthetic linear peptides can be made by chemically converting the structures to cyclic forms. Cyclization of linear peptides can modulate bioactivity by increasing or decreasing the affinity of binding of the peptide by the target protein (94). Linear peptides are very flexible and tend to adopt many different conformations in solution. Cyclization acts to constrain the number of available conformations and thus favour the more active or inactive structures of the peptide. The immunogenicity of synthetic peptides has been correlated with the experimentally observed conformational preferences in solution (95). Differences in immunogenicity may be indicative of differences in binding affinity of specific antibodies for cyclic peptides.

Cyclization of linear peptides is accomplished either by forming a peptide bond between the free N-terminal and C-terminal ends (homodetic cyclopeptides) or by forming a new covalent bond between amino acid backbone and/or side chain groups (heterodetic cyclopeptides) (93). The latter cyclizations use alternate chemical strategies to form covalent bonds, e.g. disulfides, lactones (both also present in natural peptides), ethers, or thioethers. Linear peptides of more than five residues can be cyclized relatively easily. The propensity of the peptide to form a beta-turn conformation in the central four residues facilitates the formation of both homo- and heterodetic cyclopeptides. The presence of proline or glycine residues at the N- or C-terminal ends also facilitates the formation of cyclopeptides, especially from linear peptides shorter than six residues in length.

Examples of protocols for the formation of disulfide bonds and for other cyclization reactions of peptides are given in Pennington and Dunn (105), chapters 7 and 11.

Peptidomimetics technology is the design of molecular mimics of peptides. The ability to successfully design such molecules depends on the understanding of the properties of the linear peptide sequence and the conformation in which it is presented to the IL-10 receptor. The synthesis of mimetics can provide compounds exhibiting greater biological activity, improved solubility, and stability (96).

As an example, the following peptidomimetic has been derived on the basis of the α-helical templates in C-terminal peptide mimetics of cytokines disclosed in U.S. Pat. No. 5,446,128 (97) in combination with the knowledge that the C-terminal of IL-10 exists as an α-helix (98).

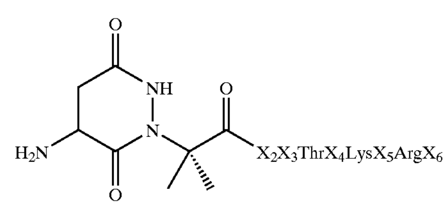

By this attachment of a small molecule at the N-terminal of the peptide, an α-helical structure of the synthetic peptide is stabilized, and the peptide is made more resistant to proteolytic degradation. Other peptidomimetics may be derived on the basis of the disclosure in U.S. Pat. No. 5,446,128. Such substances wherein substitution has taken place at other residues than $X_1$ and/or substitution has taken place with other molecules than the N-terminal molecule shown in the formula above are within the scope of the present invention.

In accordance with the present invention, the term "an analogue of the peptide" comprises any pharmaceutically active and acceptable compound derived on the basis of the above formulae and exhibiting at least one biological activity similar to IT9302, including derivatives of such analogues, especially pharmaceutically acceptable salts, esters and solvates thereof.

The following terms: "cytokine", "lymphokine", "interleukin", "monokine", "chemokine", "interferon", "colony-stimulating factor", and "polypeptide" are used as defined in WO 96/01318.

An interesting embodiment of the invention relates to a polypeptide of the invention where the number of amino acids amount in total from 6, 7, 8, 9 or 10 up to about 100 amino acids, e.g. 11, 12, 13, 14 or 15 amino acids, or even larger such as 20 amino acids or 30 amino acids.

In a preferred embodiment of the invention, the substance or polypeptide is used in substantially pure form. To obtain this, purification of the polypeptide may be required. Examples of the procedures employed for the purification of polypeptides are: (i) immunoprecipitation or affinity chromatography with antibodies, (ii) affinity chromatography with a suitable ligand, (iii) other chromatography procedures such as gel filtration, ion exchange or high performance liquid chromatography or derivatives of any of the above, (iv) electrophoretic procedures like polyacrylamide gel electrophoresis, denaturating polyacrylamide gel electrophoresis, agarose gel electrophoresis and isoelectric focusing, (v) any other specific solubilization and/or purification techniques.

Within the scope of the present invention is also a pharmaceutical composition comprising a substance or polypeptide of the invention and a pharmaceutically acceptable excipient. The composition may comprise e.g. purified synthesized protein or a purified recombinant polypeptide.

The IL-10 agonist used in this invention may be prepared as formulations in pharmaceutically acceptable media, for example, saline, phosphate buffered saline (PBS), Ringer's solution, dextrose/saline, Hank's solution, and glucose. The compositions may contain pharmaceutically acceptable auxiliary substances as required to approximate physiological conditions, such as buffering agents, tonicity adjusting agents, wetting-agents, detergents, and the like. Additives may also include additional active ingredients, e.g. bactericidal agents, or stabilizers. The amount administered to the patient will vary depending upon what is being administered, the purpose of the administration, such as prophylaxis or therapy, the state of the host, the manner of administration, and the like.

The pharmaceutical compositions are typically intended for transcutaneous or parenteral administration, e.g. intravenously, subcutaneously, or intramuscularly. Orally administrable forms are also desired and can be provided by modifying the composition to bypass the stomach environment. The composition can be used for prophylactic and/or therapeutic treatment.

Pharmaceutical compositions of the invention suitable for topical administration may e.g. be creams, ointments, lotions, liniments, gels, solutions, suspensions, pastes, sticks, sprays, or powders. The composition may be impregnated or distributed onto e.g. pads, plasters or strips and is conveniently applied 1–10 times a day.

The topical compositions will generally comprise 1–80% of the active compound by weight, based on the total weight of the preparations, such as 0.001–25% w/w of the active compound, e.g., 0.1–10%, 0.5–5%, or 2–5%. The composition may be formulated in accordance with conventional pharmaceutical practice with pharmaceutical excipients conventionally used for topical applications. Vehicles other than water that can be used in compositions can include solids or liquids such as emollients, solvents, humectants, thickeners and powders.

The pH of the composition may in principle be within a very broad range such as 3–9, although a pH of about 4 to 8 is preferred. Conventional buffering agents may be used to obtain the desired pH.

As an example, a composition for transcutaneous administration can contain 1 mg of substance (IT9302) dissolved in 1 g of cream basis such as Moistion's neutral cream with 0.05% salicylic acid (the pharmacy of Århus Kommunehospital) and be applied in amount of 0.4–0.5 mg under plastic on the skin. This composition is used in Examples 16 and 17.

Pharmaceutical compositions may alternatively be administered intravenously. Thus, the invention provides compositions which comprise an IL-10 agonist substance dissolved or suspended in an acceptable carrier, preferably an aqueous carrier. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The IL-10 agonist may also be administered with a second biologically active agent, such as a standard chemotherapeutic agent. Such agents include but are not limited to vincristine, daunorubicin, L-asparaginase, mitoxantrone and amsacrine.

In therapeutic applications, the pharmaceutical compositions are administered to a patient in an amount sufficient to produce the desired effect, defined as a "therapeutically effective dose". The therapeutically effective dose of an IL-10 agonist will vary according to, for example, the particular use for which the treatment is made, the manner of administration, the health and condition of the patient, and the judgment of the prescribing physician. For example, the dose for continuous infusion will typically be between 500 ng/kg/day and 50 $\mu$g/kg/day. This dose is calculated on the basis of a randomized controlled trial of IL-10 in humans (90).

The concentration of IL-10 agonist in the pharmaceutical formulations can vary widely, i.e. from about 10 $\mu$g to about 5 mg/ml, preferably between about 100 $\mu$g and about 2 mg/ml. The concentration will usually be selected primarily by fluid volumes, viscosities, etc., in accordance with the particular mode of administration selected. Thus, a typical pharmaceutical composition for intravenous infusion could be made up to contain 250 ml of dextrose/saline solution and 2.5 $\mu$g of IL-10 agonist.

For solid compositions, conventional non-toxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable non-toxic composition is formed by incorporating normally employed excipients, such as those carriers previously listed, and generally 10–95% of active ingredient, that is, an IL-10 agonist substance, preferably 25–75%. For aerosol administration, the IL-10 agonist is preferably supplied in finely divided form along with a surfactant and propellant. Typical percentages of IL-10 agonist are 0.01–20% by weight, preferably 1–10%. The surfactant must, of course, be non-toxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride such as, for example, ethylene glycol, glycerol, erythritol, arbitol, mannitol, sorbitol, the hexitol anhydrides derived from sorbitol, and the polyoxyethylene and polyoxypropylene derivatives of these esters. Mixed esters, such as mixed or natural glycerides may be employed.

The surfactant may constitute 0.1–20% by weight of the composition, preferably 0.25–5%. The balance of the composition is ordinarily propellant. Liquified propellants are typically gases at ambient conditions, and are condensed under pressure. Among suitable liquified propellants are the lower alkanes containing up to 5 carbons, such as butane and propane; and preferably fluorinated or fluorochlorinated alkanes. Mixtures of the above may also be employed. In producing the aerosol, a container equipped with a suitable valve is filled with the appropriate propellant, containing the finely divided polypeptide(s) and surfactant. The ingredients are thus maintained at an elevated pressure until released by action of the valve.

To enhance the serum half-life, the IL-10 agonist may be encapsulated, introduced into the lumen of liposomes, prepared as a colloid, or other conventional techniques may be employed which provide an extended lifetime of the polypeptides. Thus, in certain embodiments, the IL-10 agonist may be encapsulated in a liposome. A variety of methods are available for preparing liposomes, as described in, e.g., (83), (84), (85) and (86). As described above it has been found that IT9302 and analogues and variants thereof are useful for preventing effects of cytokines known to be pathogenetically involved in the previously described pathological conditions.

Therefore, the potentials of therapy by using the polypeptide of the invention or analogues or derivatives thereof is contemplated and should be investigated in all diseases where a therapeutic effect of hIL-10 and/or IRAP is expected (see above, Tables 1 and 2).

FIG. 1 is a diagram showing that IT9302 inhibits spontaneous IL-8 production by purified cultured human monocytes.

FIG. 2 is a diagram showing that IT9302 inhibits IL-1 induced (1 mg/ml) Il-8 production by human peripheral blood mononuclear cells.

Figure 10:
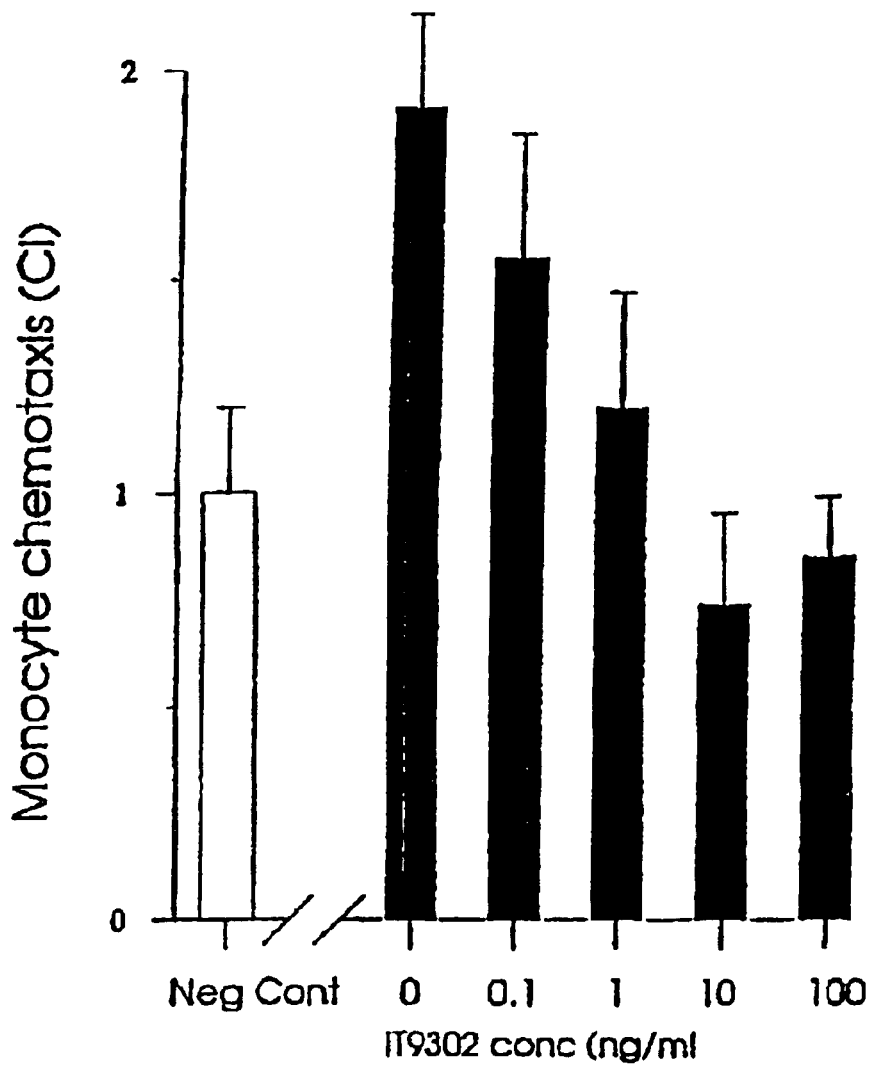

FIG. 10 shows TNF-α production in human mixed lymphocyte culture cytosolic fractions by ECL—Western Blotting. TNF-Western Blotting was carried out as the IL-4 described in Materials and Methods, but using a rabbit anti-human TNF-α antibody (Pepro Tech. Inc., London; England) and a horseradish peroxidase-labelled secondary antibody (Cat. no. p217, Dako, Denmark).

Figure 11:
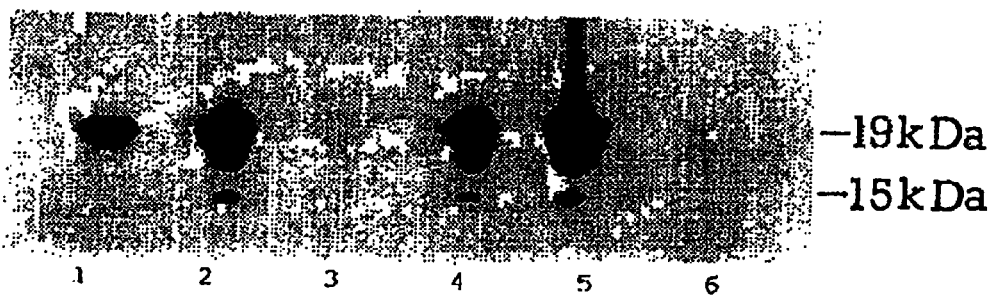

FIG. 11 shows regulation of T cell proliferation by IL-10 and IT9302.

Figure 12:
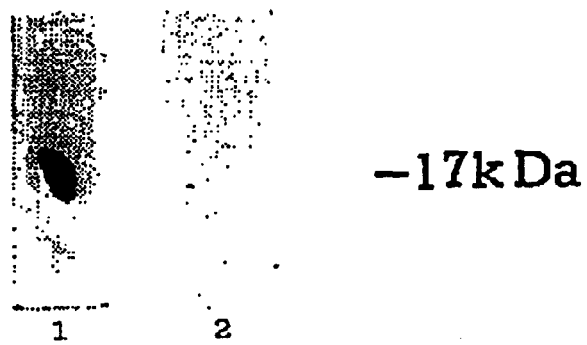

FIG. 12 shows HLA-DR expression on human monocytes (flow cytometry).

Figure 13:
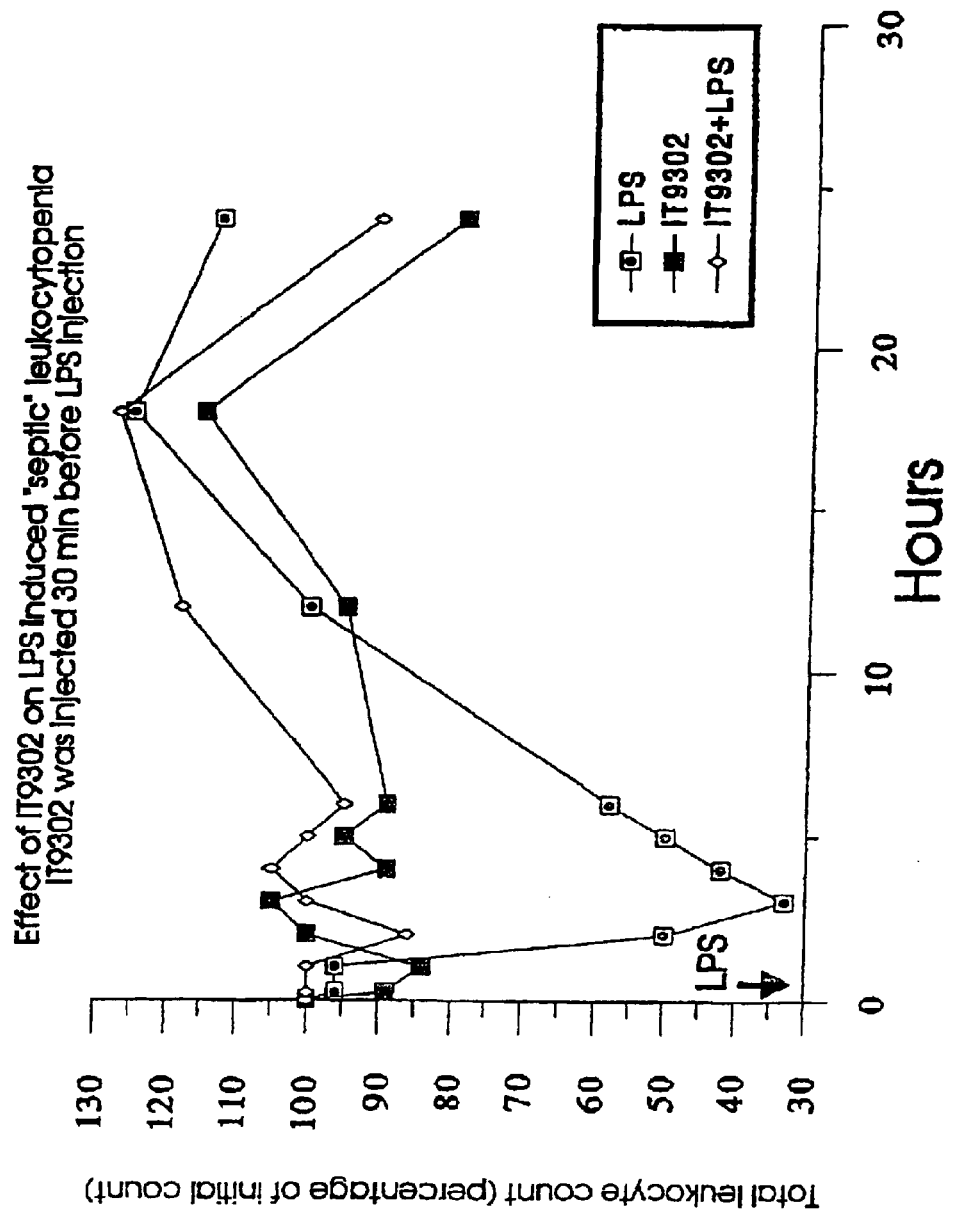

FIG. 13 shows that LPS induced shock and leukopenia are modulated by IT9302, shown by total leukocyte counting.

Figure 14:
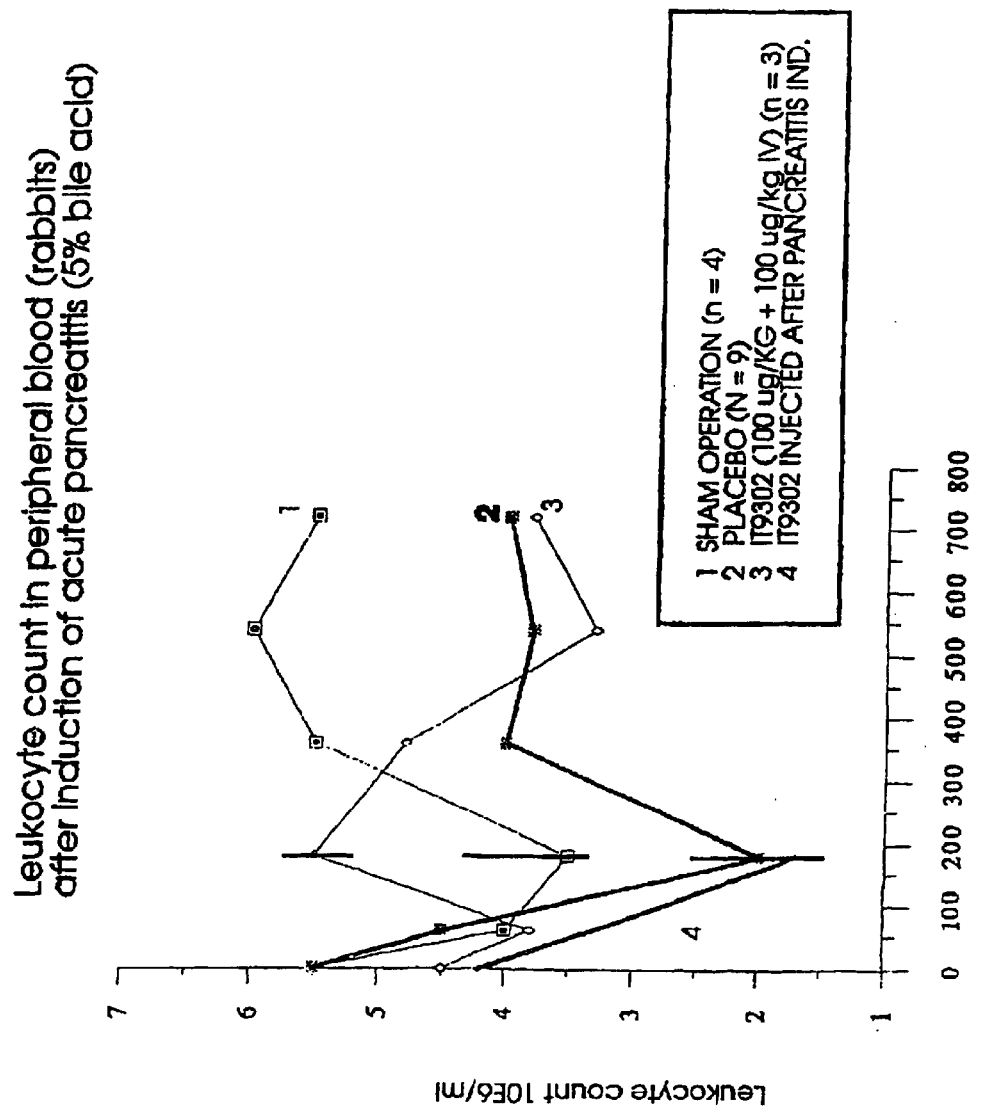

FIG. 14 shows that injection of murine IT9302 into rabbits before induced pancreatitis prevented leukopenia.

EXAMPLES

Materials and Methods

Cytokines and Chemoattractants

Recombinant hIL-10 was obtained from Pepro Tech Inc., NJ. (Cat. No. 200 10). Recombinant hIL-1β and recombinant hIL-8 were a kind gift from Dainippon Pharmaceutical Company, Osaka, Japan. The culture medium was RPMI 1640 GIBCO, LPS-free according to the *Limulus* Amoebocyte Lysate assay (Sigma E-TOXATE Kit Cat. No. 210-A1). rhMCAF/MCP-1 was a kind gift from professor Kouji Matsushima, Kanazawa, Japan.

Leukocyte Chemotaxis Assay

T Cell Chemotaxis

CD4+ and CD8+ T lymphocyte subsets characterized by expressing either CD4 or CD8 antigens were purified from hepari-=nized blood of normal donors. Thus, peripheral blood mononuclear cells (PBMC) were purified from the heparinized blood by diluting 100 ml of the blood with Hanks balanced salt solution (HBSS) 1:1 and then separated by layering the cells on Lymphopac™ (Nycomed Pharma, Oslo, Norway) followed by gradient centrifugation at 2000 rpm for 20 minutes. The mononuclear cells were washed 3 times in HBSS and the cell pellet was diluted in 4 ml of HBSS containing 1% fetal calf serum and sorted at 4° C. by using Dynabeads coated with monoclonal antibody towards CD4 or CD8 antigen (Dynabeads M-450 CD4 Cat. No. 111.16, Dynabeads M-450 CD8 Cat. No. 111.08, DETACHaBEAD Cat. No. 125.04). The bead:cell ratio was 10:1 and the incubation time 1 hour. The beads were detached by adding polyclonal anti-mouse antibody according to the manufacturer's instructions.

The chemotaxis assay was a 48-well microchamber technique (Neuroprobe, Rockville, Md.) as previously described (74; see ref. 3 and ref. 14). Chemoattractants were diluted in RPMI 1640 (GIBCO Cat. No. 61870-010) with 1% sterile filtered fetal calf serum and placed in the lower 25 μl chamber. In the case of determining T cell chemotaxis, T cells (5×10$^6$/ml) were suspended in medium and 50 μl was placed in the upper chamber separated from the lower chamber by a 5 μm pore-size polycarbonate, polyvinylpyrrolidone-free filter (Nucleopore Corp., Pleasanton, Calif.) coated with type IV collagen (Sigma Cat. No. C 0543). Cells were allowed to migrate for 2 hours at 37° C. at 5% $CO_2$. The filters were then carefully removed, fixed in 70% methanol, and stained for 5 minutes in Coomassie's Brilliant Blue. Cells attached to the lower surface of the filter were counted by measuring their area using a video camera on the microscope connected to a computer system for digital analysis and supported by software for objective determination of chemotactic migration. Approximately 5% of the T cells will migrate spontaneously corresponding to between 12,000 and 13,000 cells; this may vary from day to day, but very little in the same day's experiments. As has been described earlier (ref. 3 and ref. 14), it was therefore chosen to report the results as a ratio between number of cells migrating in the sample and in the negative control, which reflects spontaneous migration. This ratio is referred to as the chemotactic index (CI). All samples were analyzed in triplicates and cell migration in each well was measured in three fields before the median value of area was estimated. In some experiments the chemotaxis membrane was not coated with collagen, and in the present assay system migrating cells will therefore drop to the bottom of the lower well of the chemotaxis chamber.

In one experiment, the chemotactic activity of IT9302 on CD8+ T cells was performed by testing serial dilutions of IT9302 added to the lower chamber and evaluating chemotaxis as described above.

In a second experiment, the ability of IT9302 to desensitize the migration of CD8+ T cells as a response to rHIL-10 (10 ng/ml) was studied by adding IT9302 to the target cells 30 minutes before chemotaxis. IT9302 was added in serial concentrations and the chemotactic response of rhIL-10 was evaluated as described above.

In a third experiment, the ability of IT9302 to suppress the chemotactic response of CD4+ T cells towards rhIL-8 (10 ng/ml) was studied by adding IT9302 to the target cells 30 minutes before performing chemotaxis. IT9302 was added in serial concentrations and the chemotactic response of rhIL-8 was evaluated as described above.

Monocyte Chemotaxis

Monocyte chemotaxis was measured using the same Boyden chamber equipment as described for T cells above. The chemoattractant MCAF/MCP-1 was diluted in RPMI 1640 medium with 0.5% BSA and added to the lower chamber at a concentration of 10 ng/ml. Monocytes, purified by the standard plastic adherence technique, from normal human PBMC, obtained as described above were suspended in RPMI 1640 medium with 0.5% BSA and then incubated for 30 minutes in the presence of IT9302 at different concentrations. Subsequently, the cells were added to the upper chemotaxis chambers at a concentration of $10^6$ cells/ml. The upper and lower chambers were separated by an 8 $\mu$m pore size polyvinyl pyrrolidone-free polycarbonate filter (Nucleopore, Pleasanton, Calif.). The chamber was incubated at 37° C. for 90 minutes. The membranes containing migrating cells were treated as described above and a chemotactic index calculated according to the technique described above.

Production of IL-8 by Normal Human Peripheral Mononuclear Cells (PBMC)

PBMC was purified from heparinized blood of normal human donors. Following gradient centrifugation with Lymphoprep™ (Nycomed Pharma, Oslo, Norway), the mononuclear cells were diluted to $2\times10^6$ cells/ml in LPS-free RPMI 1640 medium (Gibco Cat. No. 6187-010) containing lt sterile filtered heat-inactivated fetal calf serum and penicillin (10,000 IE/ml), streptomycin (10 mg/ml) and gentamycin (2.5 mg/ml). Cells were cultured in 24 wells Nunc Micro Plates (Nunc, Denmark) and in the presence of different concentration of IT9302 (0, 1 $\mu$g, 100 ng, 10 ng, 1 ng, 0.1 ng, 0.01 ng/ml) for 24 hours. Following 24 hours of incubation, another dose of IT9302 was added once more, and 1 hour later r-hIL-1$\beta$ (1 ng/ml) was added to the cell cultures. Supernatants were collected after a total of 48 hours of incubation, and the concentration of the secreted IL-8 was measured by IL-8 ELISA by using an IL-8 ELISA Kit (Dainippon Pharmaceutical Co. Ltd, Osaka, Japan). Briefly, standards and cell supernatants were incubated for one hour and in duplicates at 20° C. on a micro-plate shaker. Then after washing, a second antibody was added for one hour, followed by one hour of incubation with peroxidase-labelled goat anti-rabbit IgG. After washing, the reaction was developed with O-phenylenediamine. Thirty minutes later the reaction was stopped with 1.6 N sulphuric acid. Optical density (OD) was measured in an ELISA reader at 490 nm. IL-8 concentration was calculated by a calibration curve of absorbance of unknown vs concentrations of IL-8 standards.

Determination of IL-RAP Concentration

PBMC was purified as described above. PBMC was cultured in RMPI 1640, 10% sterile heat-inactivated fetal calf serum (including penicillin 10,000 IE/ml, streptomycin 10 mg/ml, gentamycin 2.5 mg/ml) and the cell concentration was $5\times10^6$ cells/ml. The monocytes were then purified by standard plastic adherence technique. Monocytes were then cultured in RPMI 1640 with 2% FCS ($2.5\times10^6$ cells/ml) and with different dilutions of rhIL-10 or IT9302. The cells were stimulated for 24 hours and the supernatants were collected for IRAP determination. IRAP ELISA was carried out by using Human IL-1ra Quantikin Immunoassay Kit from R&D Systems Europe Ltd. (Cat. No. DRA 00, Abingdon, Oxon, UK).

Determination of T Cell Proliferation

Proliferation assay. PBMCs ($2\times10^5$) were cultivated in 200 $\mu$l of RPMI medium with 10% FCS for 72 hours with PHA 0.5 $\mu$l/ml and rhIL-10 (1, 10, 100 ng/ml) or IT9302 (0.1, 1, 10 ng/ml) in triplets. The last 18 hours $^3$H-thymidine was added with 0.5 $\mu$Ci/well (Amersham, Denmark). The cells were harvested on a filter (Glass Microfibre Filters, Whatman, Cat. No. 1822 849) and scintillation fluid (Ultima, Gold MV, Packard) was added. The scintillation counting was made on Tri-Carb model 1600 TR, Packard.

Determination of Class II MHC Antigen Expression on Monocytes

HLA-DR expression on human monocytes. The monocytes were isolated from fresh, heparinized blood by adherence to plastic at 37° C. in RPMI 1640 containing 10% FCS. After incubation, the supernatant was removed, Hank's solution (4° C. with 1% FCS) was added, and the cells were detached by cooling at -20° C. for 15 minutes and gentle banging to the table. Monocytes were stimulated ($2\times10^6$ cells/ml) in RPMI 1640 added 2% FCS, with IFN-$\gamma$ (10 ng/ml), or rhIL-10 (100, 10, 1 ng/ml) added before IFN-$\gamma$, or IT9302 (10, 1, 0.1 ng/ml) added before IFN-$\gamma$ for 40 hours. The cells were detached from the wells by cooling as before. Fresh, non-fixed cells were used for surface typing by antihuman antibody for HLA-DR. The cells were resuspended in Hank's solution with 1% FCS, $1\times10^6$ cells/ml and FITC conjugated mouse-anti-human HLA DR, DP, DK antibodies were added (F 0817, DAKO Denmark) for 45 minutes. The cells were washed three times in Hank's solution and a FACS analysis was performed on a Coulter-Epics XL-MCL flow cytometer at a wavelength of 488 nm. Non-specific binding was determined with a non-relevant Fitch conjugated antibody (mouse anti goat DAKO F 479).

Alternatively cells were fixed in 10% DMSO, 40% RPMI 1640 and 50% sterile FCS, and stored at -80° C. and used for DNA typing.

Determination of Apoptosis in Monocytes

DNA typing of the stimulated monocytes. The fixed cells were incubated in 70 ethanol for 60 minutes and washed twice in Hank's solution. $1\times10^6$ cells were resuspended in 250 $\mu$l of RNase 1 $\mu$g/ml in 1.12% sodium citrate, pH 8.4 (Ribonuclease A, Pharmacia No. 17-0442-01) and incubated at 37° C. for 3 minutes. Thereafter, 250 $\mu$l of propidiumiodide (50 $\mu$g/ml in Hank's solution) was added, and cells were incubated in the dark for 30 minutes. After this the cells were washed twice in Hank's solution (Jensen et al., (110)). The DNA content was measured by flow cytometry on a Coulter-Epics XL-MCL at a wavelength of 550 nm.

Results
Regulation of T Cell Proliferation by IL-10 and IT9302

PBMC's were stimulated with PHA as described above and rhIL-10 and IT9302 were added for 72 hours, and the $^3$H-thymidine incorporation was measured for the last 18 hours. Both rhIL-10 and IT9302 downregulated cell proliferation in an optimum concentration of 100 ng/ml rhIL-10 and 10 ng/ml IT9302, as seen in FIG. 11.

HLA-DR Expression on Human Monocytes

The monocytes were purified as described above and stimulated for 40 hours by IFN-γ (10 ng/ml) and/or rhIL-10 and/or IT9302 added 30 minutes before IFN-γ. MHC II antigen expression was studied by incubation with FITC conjugated mouse-anti-human HLA DR, DP, DK antibody. The expression of MHC II antigen was upregulated by IFN-γ as seen in FIG. 12, and 10 ng/ml rhIL-10 and 1 ng/ml IT9302 downregulated the MHC II antigen expression in a similar way.

DNA Typing of the Stimulated Monocytes

The IFN-γ stimulated monocytes from above were incubated with propidium iodide and the DNA content was measured by flow cytometry. The fraction of cells expressing DNA in $G_1$ or $G_2$ phase of cell proliferation was measured and also the fraction expressing apoptosis. As seen in FIG. 12, non-stimulated monocytes were expressing 6.6% apoptosis, IFN-γ stimulation downregulated apoptosis to 4.1%, while both IL-10, IFN-γ and IT9302+IFN-γ stimulation of the cells induce the apoptosic fraction to 10.3% and 9.3%, respectively.

Determination of IL-4 Production by CD4+ T Lymphocytes Cell Cultures

CD4+ T lymphocytes were purified from heparinized normal human blood. Following Lymphoprep™ (Nycomed Pharma, Oslo, Norway) gradient centrifugation, the mononuclear cells were further sorted at 4° C. using Dynabeads (Dynal AS, Norway) coated with monoclonal anti-CD4 antibodies. The beads were detached by adding polyclonal anti-mouse antibody (Dynal AS, Norway). The purity of the positively selected cells were higher than 99% as judged by FACS analysis. When examining the de novo production of IL-4 by IL-8-stimulated T cells, T cells were cultures, 5×10$^6$ cells/ml in LPS-free RPMI 1640 (Gibco Cat. no. 61870-010) containing 1% sterile-filtered, heat-inactivated fetal calf serum (FCS), penicillin (10,000 IU/ml), streptomycin (10 mg/ml) and gentamycin (2.5 mg/ml). T cells were stimulated for 3 days using rIL-8 (100 ng/ml), rIL-10 (100 ng/ml), IT9302 (10 ng/ml) and IFN-7 (10 ng/ml). Recombinant human IL-8 (rh IL-8) was a kind gift from Dainippon Pharmaceuticals Co. Ltd., Osaka, Japan), and IFN-γ was purchased from Boehringer Ingelheim Am Rhein, Germany. To obtain specific inhibition of IL-8 stimulation, a neutralizing monoclonal anti-IL-8 antibody (WS.4) was used (a kind gift from Dr. K. Matsushima, Japan). Recombinant IL-10 was purchased from Pepro Tech. Inc. (London, England).

Preparation of Cell Material and Culture Supernatant for Gel Electrophoresis

Cultured T cells and culture media were separated by centrifugation at 2000 rpm for 5 minutes. The supernatants were freeze-dried and then dissolved in 100 μl of lysis buffer. The cells were resuspended directly in 100 μl of gel lysis buffer (9). The material was kept at −80° C. until further examination.

ECL-Western Blotting of CD4+ T Cell Derived Proteins

Cells or freeze-dried cell culture supernatants were used for IL-4 protein content determination. Proteins from one-dimensional 15% SDS-PAGE gels were transferred by blotting onto Hybond-ECL nitrocellulose membranes (Amersham RPN 2020D, UK) and blocked with 5% bovine serum albumin (Sigma) in Tris buffer saline pH 7.8 containing 0.1 Tween-20. The blots were then incubated with a polyclonal goat anti-human IL-4 antibody (R&D Systems, UK) followed by a horseradish peroxidase-labelled secondary antibody (Cat. no. RPN 2106 ECL, Amersham, UK), and the immunostaining was detected by exposing a film (Kodak X-OMAT-S, USA) for 90 seconds.

EXAMPLE 1

Inhibition of Spontaneous IL-8 Production by Human Monocytes

The test was performed as described in "Production of IL-8 by normal human peripheral mononuclear cells (PBMC)". Monocytes were purified by plastic adherence technique and 3.0×10$^6$ cells/ml were stimulated for 40 hours. As shown in FIG. 1, IT9302 inhibited the production of IL-8 by monocytes, and at 0.1 ng/ml of IT9302 the IL-8 production was suppressed to 35% of the spontaneous production in vitro. The viability of cells always exceeded 80% after 1 day in culture and the addition of IT9302 did not in this or in the following examples affect viability at any concentration of IT9302 between 0.1 and 1000 ng/ml (IT9302 MW: 1,127 dalton, rhIL-10 predicted MW: 18,400 dalton).

EXAMPLE 2

Inhibition of IL-1β Induced IL-8 Production by Human Peripheral Blood Mononuclear Cells (PBMC)

The test was performed as described in "Production of IL-8 by normal human peripheral blood mononuclear cells (PBMC)". As shown in FIG. 2, IT9302, in a dose dependent manner, inhibited the IL-1β induced production of IL-8 by human peripheral blood mononuclear cells in vitro. The suppression of IL-8 production plateaued at IT9302 concentrations between 0.01 and 100 ng/ml.

EXAMPLE 3

Figure 3:
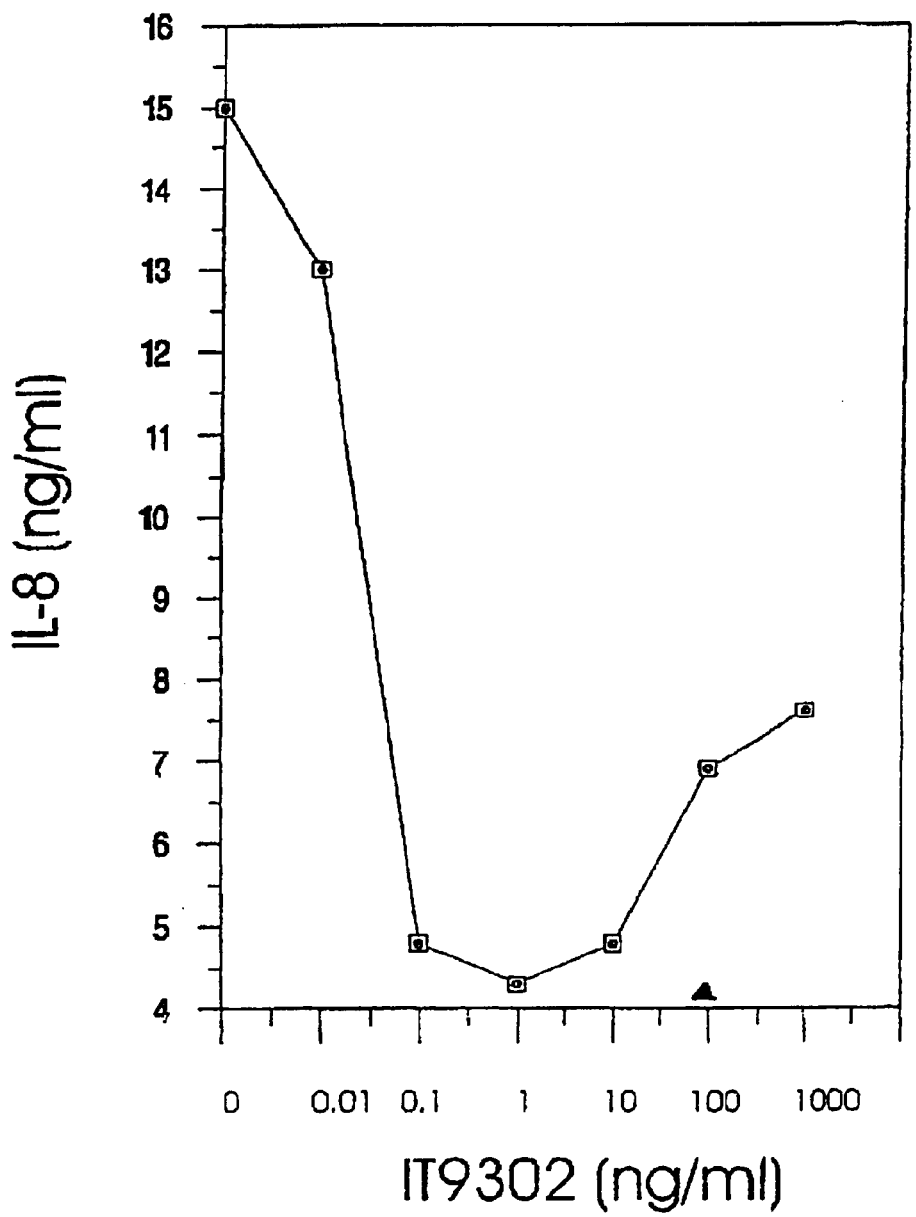
FIG. 3 illustrates IRAP production by IT9302-stimulated human monocytes.
Figure 4:
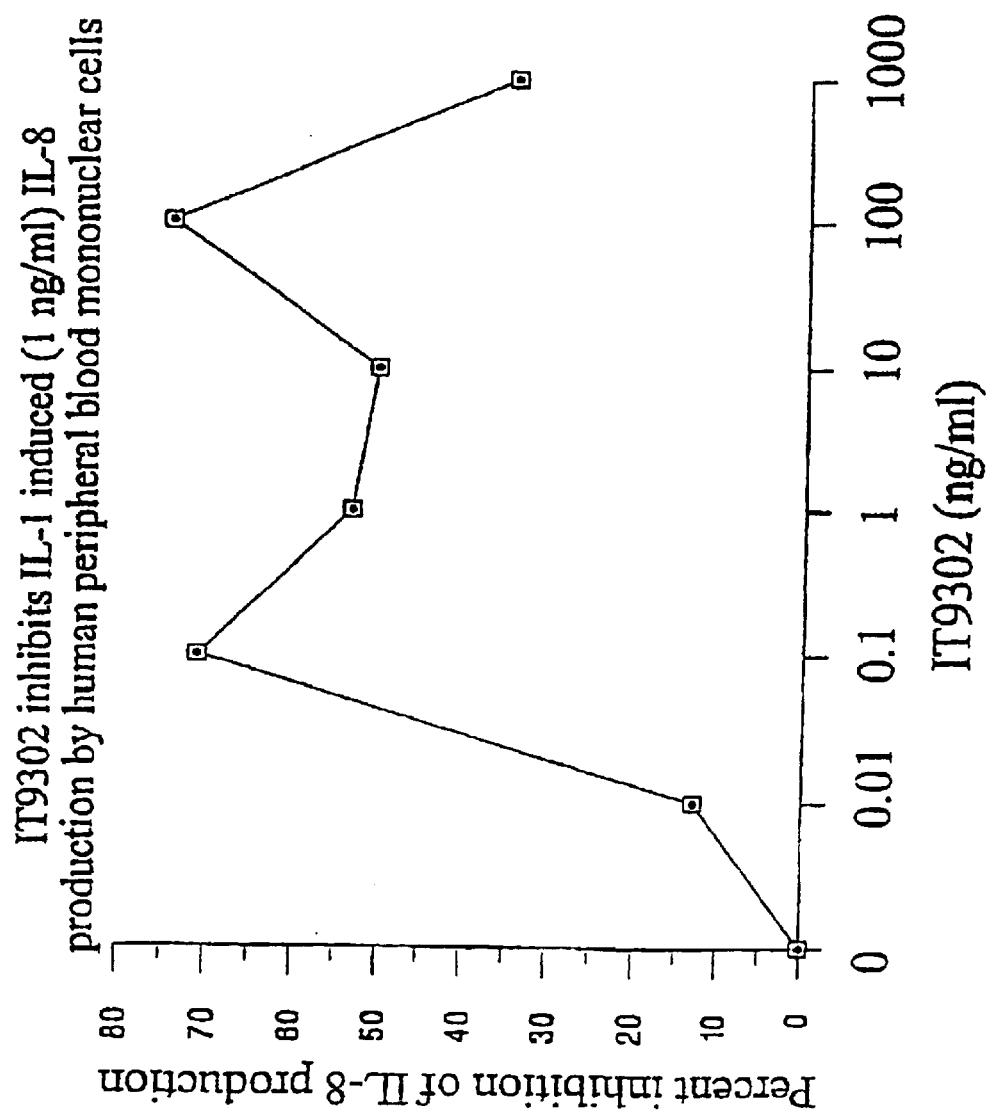
FIG. 4 illustrates IRAP production by IL-10-stimulated human monocytes.

Production of Interleukin-1 Receptor Antagonist Protein (IRAP) by Human Monocytes The test was performed as described in "Determination of IRAP concentration". As shown in FIG. 3, IT9302 dose-dependently induced the production of IRAP by human monocytes. The production drastically increased when using concentrations of IT9302 above 10 ng/ml. FIG. 4 shows the induction of IRAP by rhIL-10 and since hIL-10 is approximately 20 times larger than IT9302, 5 ng/ml of IT9302 equals 100 ng/ml of IL-10 in molarity. Therefore the potencies of IT9302 and rhIL-10 are comparable and approximately equal with respect to the induction of IRAP at lower concentrations. At IT9302 concentrations exceeding 10 ng/ml, the induction of IRAP increased and reached a maximum level of 60 ng/ml. Further, the specificty of this induction by the antibody which is specifically directed against IT9302 was tested. In a separate experiment where the monocytes spontanously produced 3.5 ng/ml IRAP and they were induced by 1–10 ng/ml IT9302 to a maximum IRAP production of 10.6+0.6 ng/ml, this production could be blocked by a polyclonal antibody for IT9302, 2 μg/ml added 30 minutes before 10 ng/mg IT9302, so the level of IRAP was: downregulated to 2.9+0.3 ng/ml. This results is in contrast to the result obtained with the antibody directed against IL-10, 19F1, which added in the same way (2 μg/ml 30 minutes before 10 ng/ml IT9302) did not block IRAP production but on the contrary upregulated this to 22 ng/ml. This result can be explained by that this antibody is able to neutralize endogenous IL-10 but not IT9302. The spontaneously produced IL-10 in the cell culture has a negative autoregulatory effect on IRAP production by IT9302.

EXAMPLE 4
The Chemotactic Effect on Human CD8+ T Lymphocytes

Figure 5:
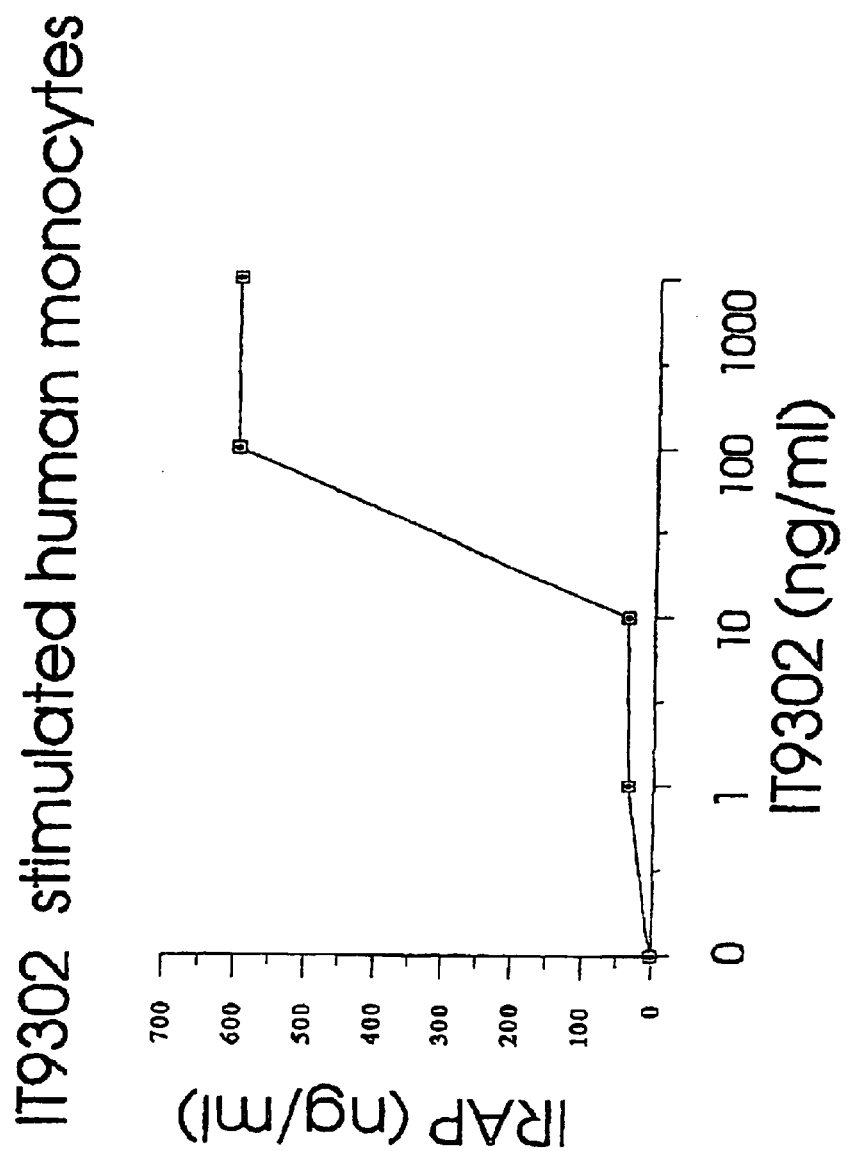
FIG. 5 illustrates the chemotactic activity of IT9302 on CD8+ T cells.

The experiment was carried out as described in "Leukocyte chemotaxis assay". As shown in FIG. 5, IT9302 induced the chemotactic migration of CD8+ human T lymphocytes in vitro, while there was no effect on CD4+ T cells (data not shown). Again, the potency of IT9302 shown in this experiment is comparable with that of rhIL-10 shown previously (14).

EXAMPLE 5
Desensitization of Human CD8+T Cells Resulting in an Unresponsiveness Towards rhIL-10

Figure 6:
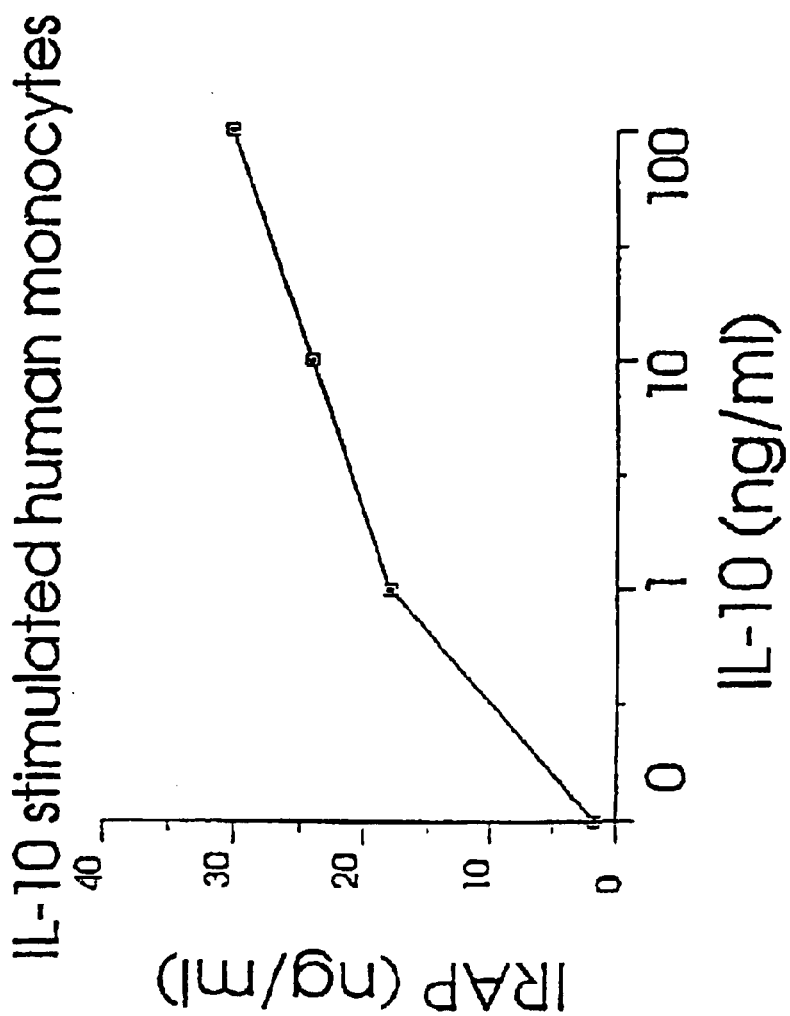
FIG. 6 illustrates the desensitization of CD8+ T cells by IT9302, resulting in unresponsiveness of CD8+ T cells towards IL-10 (10 ng/ml) induced chemotaxis.

The experiment was carried out as described in "Leukocyte chemotaxis assay". IT9302 was added to a suspension of CD8+ T cells 30 minutes before these cells were tested towards their chemotactic response to rhIL-10. As shown in FIG. 6, the preincubation of cells with IT9302 results in a suppressed responsiveness of the CD8+ T cells towards hrIL-10. This indicates that IT9302 may affect the binding of rhIL-10 to the IL-10 receptor.

EXAMPLE 6

Suppression of the Chemotactic Response of CD4+ T Lymphocytes Towards IL-8

Figure 7:
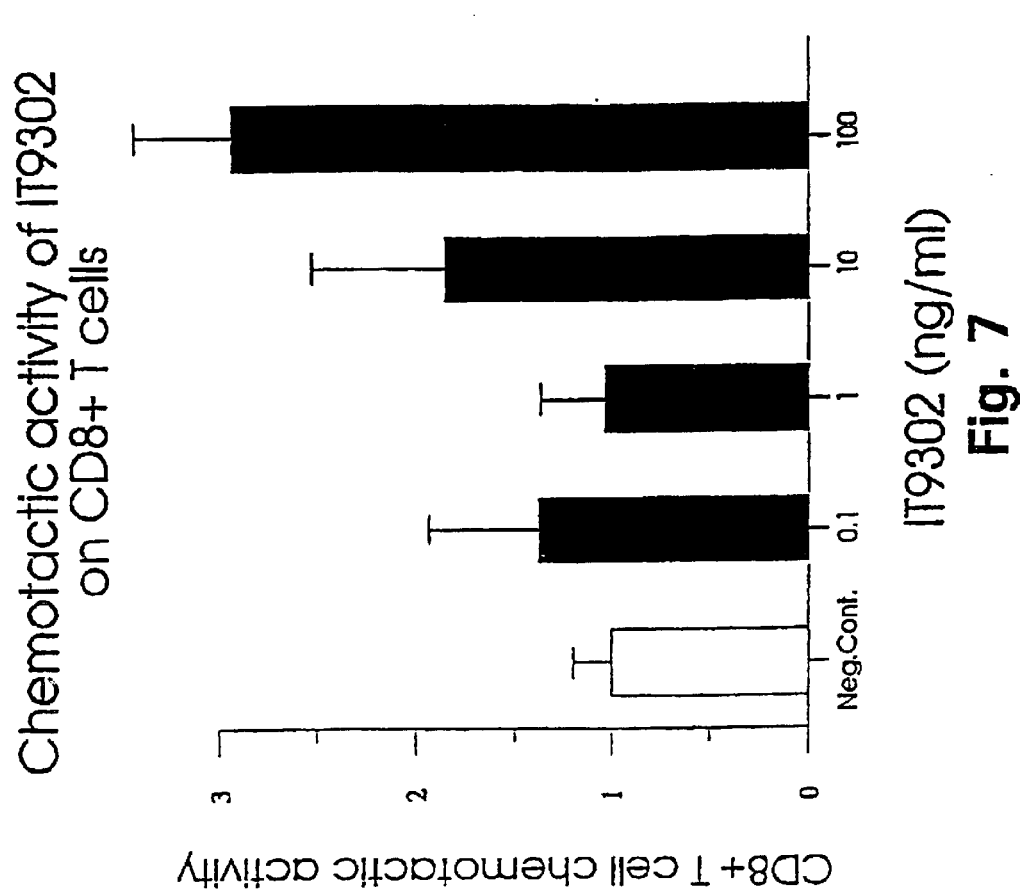
FIG. 7 illustrates the suppression of IL-8 activity on CD4+ T cells by IT9302.

The experiment was carried out as described in "Leukocyte chemotaxis assay". As shown in FIG. 7, IT9302, in a dose-dependent manner and added to a suspension of human CD4+ T lymphocytes, inhibits the response of the CD4+ T cells towards IL-8.

EXAMPLE 7

Suppression of the Chemotactic Response of Human Monocytes Towards MCAF/MCP-1

Figure 8:
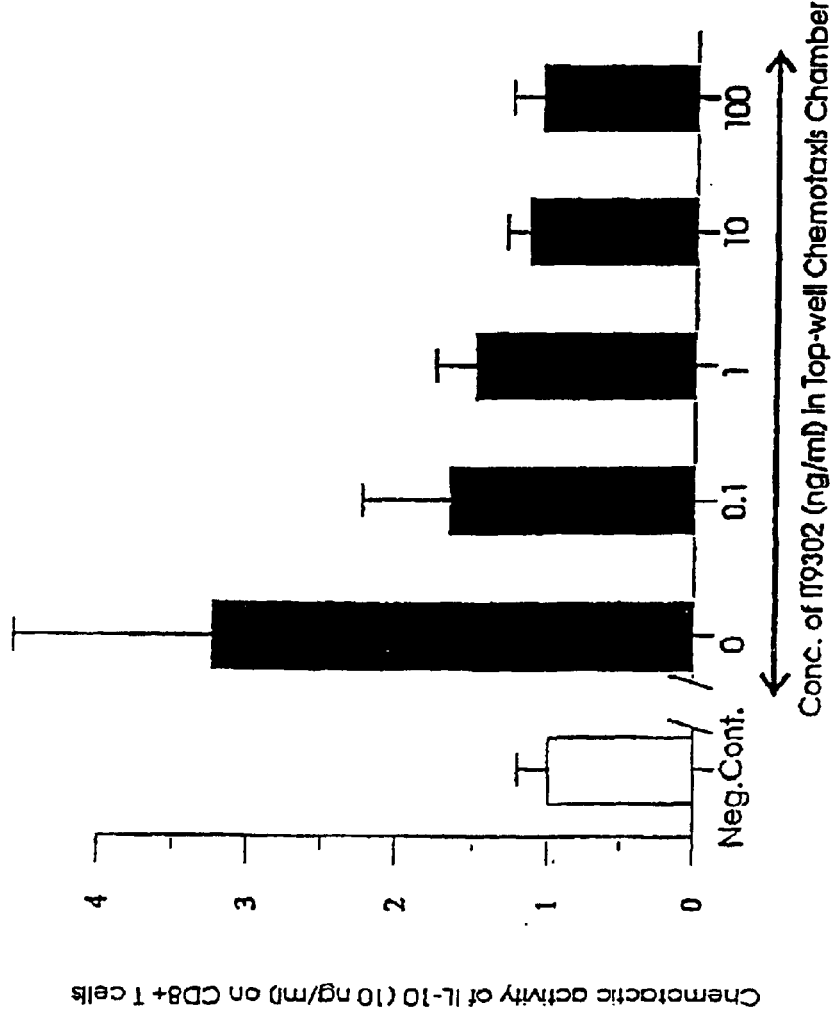
FIG. 8 is a diagram showing that IT9302 inhibits MCAF/MCP-1 induced monocyte chemotaxis.

The experiment was carried out as described in "Monocyte chemotaxis". As shown in FIG. 8, IT9302, in a dose-dependent manner and added to a suspension of human monocytes, inhibits the chemotactic response of the monocytes towards MCAF/MCP-1.

EXAMPLE 8

Inhibition of Class II MHC Molecule Expression on Human Monocytes when Stimulated with IFNγ

In a new experimental model (flow cytometry), it has been shown that monocytes stimulated with IFN-γ upregulate their expression of MHC II antigen, and this induction can be blocked by IL-10 and IT9302 in a similar way. At the same time, both peptides upregulate the number of cells showing apoptosis in the monocytes (see FIG. 12). These experiments indicate that IL-10 and IT9302 can inhibit monocyte/macrophage dependent T cell proliferation by diminishing the antigen presenting capacity of monocytes via the down-regulation of Class II MHC expression (see 12).

PMBC's stimulated by PHA start to proliferate as shown by $^3$H-thymidine incorporation, which can also be downregultaed by IL-10 and IT9302' PHA stimulates T cell proliferation through activation of $Ca^{2+}$ dependent channels. $Ca^{2+}$ fluxes in human T cell clones were diminished when cells were preincubated with IL-10 (Taga, K. et al., 1992). The present experiment shows that T cell proliferation is downregulated by IT9302 also by the control of the $Ca^{2+}$ dependent channels.

Discussion related to the experiments

The present data demonstrate a dose-dependent inhibitory effect of the synthetic nonapeptide, IT9302, on processes which reflect pro-inflammatory activity, including IL-8 production and monocyte and/or T cell migration. Thus, IT9302 was able to suppress the spontaneous production of IL-8 by human monocytes cultured overnight. This could be explained by a direct inhibitory effect on IL-8 mRNA production and/or subsequent protein production and or release. Another mechanism could be explained by the fact that monocytes cultured in vitro will express and produce IL-1, which then in turn induces the production of IL-8. This is supported by the fact that it has been demonstrated that IT9302 potently induces the production of IRAP from monocytes. IT9302 may therefore also inhibit spontaneous IL-8 production by interfering with the activity of IL-1. The observed IRAP induction by IT9302 appears to induce a biologically active IRAP, since IT9302 added to the cultures counteracts IL-1-induced IL-8 production, but only when added at least 16 hours before adding IL-1 to the cultures. This could mean that IT9302 inhibits IL-1-induced IL-8 production by inducing the production of IRAP, which then in turn blocks the activity of IL-1 through its receptor. If IT9302 directly inhibited IL-8 production, it would have been expected that addition of IT9302 to the cultures 1 hour before adding IL-1 should inhibit IL-8 production, which was not the case (data not shown). Therefore, the observed inhibition of IL-8 production of IT9302 is likely to be due to an induction of IRAP production rather than a direct inhibition of IL-8 production. IT9302 specifically blocks the IL-1 receptor by the induction of IRAP, and thereby the induction of other cytokines which are induced by IL-1, like TNFα, IL-8 and probably many other cytokines and factors. The specificity of the induction was confirmed by that our antibody for IT9302 could block the induction of IRAP. Another IL-10 antibody 19F1 did not block IT9302-induced IRAP production.

IT9302 also mimics IL-10 activity by suppressing the ability of CD4+ T cells to migrate as a response to IL-8. Since IL-8 is related to many different states of inflammation and since CD4+ T cells appear early in the infiltrate of T cell-mediated immune inflammation such as allergy of the skin, this feature may prove to have significant therapeutic value for the control of T cell-mediated immune inflammation.

The demonstrated CD8+ T cell chemotactic activity of IT9302 is also parallel to that of IL-10, and IT9302 may thus activate T cell populations with suppressor activity contributing to the ending of T cell-mediated immune inflammation. Therefore IT9302 according to the examples which are demonstrated above, possesses therapeutic value in diseases where IL-10 and/or IRAP may also have therapeutic value. Additionally, IT9302 may have therapeutic value in diseases where IL-8 and/or MCAF and/or IL-1 are believed to have pathogenetic roles. The present invention describes analogues of IT9302, i.e. substances or peptides having at least some of the above-described properties.

EXAMPLE 9
Induction of the Production of IL-4 in CD4+ T Lymphocytes

BACKGROUND

Like IL-10, IL-4 is a product of CD4+ T cells of $T_H2$ type. It was observed that recombinant human IL-10 induces the production of IL-4 by cultured human CD4+ T cells. This means that IL-10, in addition to its own immunosuppressive functions, also induces the production of another immunosuppressive cytokine, IL-4. It was therefore tested whether IT9302 also induces the production of IL-4 by CD4+ T cells.

Thus, CD4+ T cells, purified as described in "Methods for T cell chemotaxis", and cultured as described in the section "Determination of IL-4 production by CD4+ T lymphocytes", were stimulated for 3 days with IT9302 (10 ng/ml) or IL-10 (100 ng/ml). Cytosolic fractions were collected and analyzed for their IL-4 content using Western blotting (FIG. 9) and a goat anti-human IL-4 polyclonal antibody.

Figure 9:
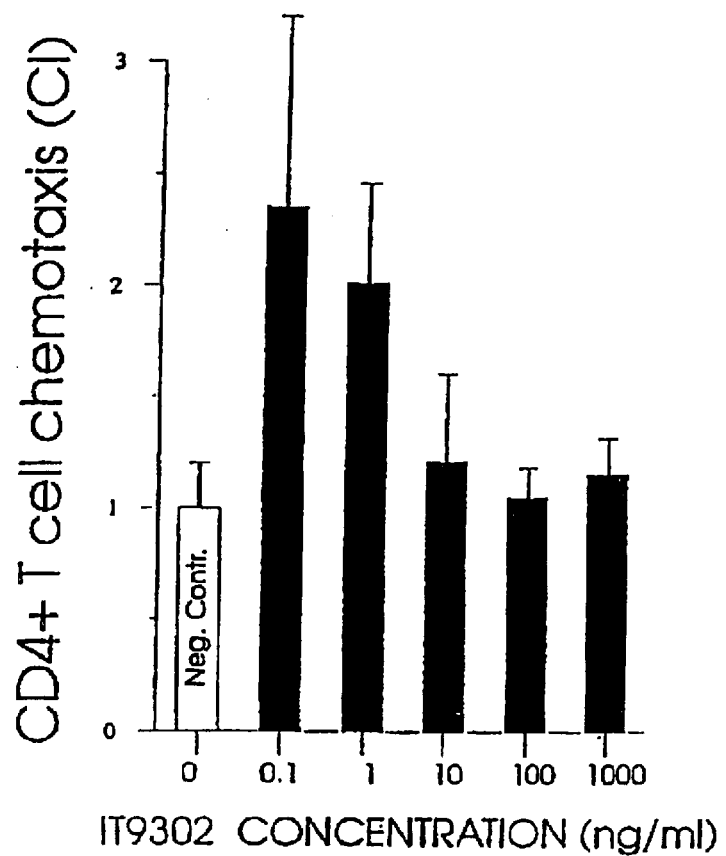
FIG. 9 shows IL-4 production in CD4+ T cell cytosolic fractions by ECL—Western Blotting.

As demonstrated in FIG. 9, it was observed that IL-10 as well as IT9302 induce the production of IL-4 by cultured normal human CD4+ T cells.

EXAMPLE 10
Inhibition of the Production of TNF-α During a Mixed Leukocyte Reaction (MLR)

It has been demonstrated that the mixed leukocyte reaction is partly dependent on the production of TNF-α during the reaction. It has been shown that IT9302 does not significantly reduce the MLR, but it was found that there is a significant reduction in the production of TNF-α during the MLR. Thus, MLR was performed by purifying human leukocytes and then culturing 1 million cells/ml from allogeneic donors for 4 days. Before establishing the cultures, one group of cells was irradiated for 2 minutes using beta irradiation. Cytosolic protein fractions were purified as described in the section "Determination of IL-4 production by CD4+ T lymphocytes", and Western blotting was performed using a rabbit antihuman TNF-α antibody.

As demonstrated in FIG. 10, a significant reduction in the production of TNF-α was observed during a human mixed leukocyte reaction.

EXAMPLE 11
The modulation of the LPS Induced Shock and Leukopenia in Swine

Since it was found that IT9302 modulates cytokine production, including TNF-α and IL-8, and supported by the published sequence of porcine IL-10 (88), it was tested whether IT9302 was able to modulate the course of LPS induced leukopenia in swine (FIG. 13).

In a preliminary experiment, it was tested how the intravenous injection of IT9302 0.1 mg/kg modulated the effect of intravenous injection of 2 Ag/kg LPS in swine (N=3). IT9302 was injected 30 minutes before injection of LPS, and blood samples were drawn as described in FIG. 13. Total leukocyte count as well as differential cell count were determined, and the total number of neutrophilic leukocytes was calculated on the basis of these results.

As demonstrated, it was observed that injection of LPS caused a transient leukopenia. Injection of IT9302, however, prevented leukopenia as demonstrated in the figure.

EXAMPLE 12
The effect of Murine IT9302 Homologous to Human IT9302 on TNF-α Release in Plasma After LPS Administration in Mice It has been demonstrated in animals that recombinant murine IL-10 can protect mice from lethal endotoxemia (89) and in addition, it has been demonstrated that IL-10 administrated in humans has inhibitory effects on T-cells and suppresses production of proinflammatory cytokines (90). The aim of the study was to test whether IT9302 can suppress production of TNF-α in mice exposed to endotoxin-induced shock after administration of LPS (FIG. 14).

Eight week old BALB/C mice were used (obtained from Centre for Research Animals, Bomholtgaard, Bomholtvej 10, DK-8680 Ry, Denmark). LPS from *E. coli* was from Sigma (batch 3444114) and murine IT9302 was from Schafer-N, Lersø Parkallé 42, DK-2100 Copenhagen Ø, Denmark.

Mice were injected intraperitoneally with 100 µg of LPS in 1 ml of 0.9 M NaCl. 60 minutes prior to LPS injection mice were given murine IT9302 equivalent to 0.1 µg, 1 µg and 10 µg of human IL-10. Groups of 5 animals were anaesthetized (Imobilon, Pherrovet, Malmö, Sweden) after 1, 2, 3 and 4 hours, respectively, after which a maximum of whole blood was drawn through cardiac puncture. The blood was centrifuged in the cold and sera were collected and stored at −70° C. for subsequent analysis of TNF-α content by ELISA (TNF-α Mouse Immuno Assay Diagnostic kits, Genzyme, Cambridge, Mass., USA).

As demonstrated, it was observed that 10 µg of murine IT9302 clearly suppressed TNF-α in mouse sera compared to the control group not treated with mIT9302 (see Table 3).

TABLE 3

| m-TNF-α ng/ml + SEM in serum of mice Murine IT9302 equivalent to hIL-10 added 60 minutes before LPS | | | | |
|---|---|---|---|---|
| | 0 | 0.1 µg | 1 µg | 10 µg |
| 1 h | 2.48 ± 0.16 | 1.92 ± 0.48 | 2.64 ± 0.38 | 1.84 ± 0.16 |
| 2 hs | 1.43 ± 0.17 | 1.68 ± 0.27 | 1.16 ± 0.21 | 0.62 ± 0.14 |
| 3 hs | 0.48 ± 0.04 | 0.05 ± 0.02 | 0.18 ± 0.05 | 0.0 |
| 4 hs | 0.09 ± 0.06 | 0.06 ± 0.02 | 0.20 ± 0.04 | 0.05 ± 0.01 |

EXAMPLE 13
The Modulation of Acute Pancreatitis Induced by Bile Acid Using Murine IT9302

Rodents, mice and rabbits are often used in animal models, and recently Genzyme Diagnostics has advertized with Cross-reactivity Kits for Cytokine Research Products. Especially, it was possible to measure rabbit TNF-α and IFN-γ by mouse Immunoassay Kits. As we were working on a rabbit model, studying the pathophysiological role of IL-8 in experimental acute pancreatitis, we investigated the effect of the murine IT9302 on induced leukopenia (FIG. 14). Our hypothesis was that even IL-10 could be identical in mice and rabbits and might have effects on IL-8-induced leukocyte invasion in the pancreas during acute pancreatitis.

Experimental Model

New Zealand white rabbits (*Oryctolagus cuniculus*) weighing 1.7–4.0 kg were fasted for 18–24 hours. The operative procedures according to Banerjee et al., 1994 (91) and Hong et al., 1962 (92) were followed, and acute pancreatitis was induced in rabbits by 5% bile acid given into the pancreatic duct. Murine IT9302 (100 µg/kg) was given through a central vein 30 minutes before the bile and subcutaneously in a dose of 100 µg/kg rabbit immediately afterwards. Plasma samples were collected according to FIG. 14.

As demonstrated, it was observed that injection of murine IT9302 into rabbits before induced pancreatitis prevented leukopenia as demonstrated in the Figure.

EXAMPLE 14
The Modulation of Acute Pancreatitis in Rabbits Induced by Bile Acid Using Human IT9302

The same experimental model was used as in Example 13 with the exception that the murine IT9302 was exchanged by human IT9302. Acute pancreatitis was induced by intraductal injection of 2.0 ml of 5% chemodeoxycholin bile acid (10 animals). Another group of animals was treated with human IT9302 (8 animals), the first dose (100 µg/kg) being injected subcutaneously and the second dose (100 µg/ml) intravenously, half an hour before the induction of acute pancreatitis. Serum samples were collected for cytokine measurements with time intervals, 0, 1, 3, 6, and 12 hours after the induction of acute pancreatitis.

Methods for the TNF-β and IL-8 Measurements in Rabbit Serum

Genzyme mouse TNF-α ELISA kit code No. 80-3807-00 was used in a modified version for TNF-α measurements in the serum of rabbits. This kit is built up by a solid-phase monoclonal hamster anti-mouse TNF-α antibody which captures the TNF-α present in serum, and a peroxidase-conjugated polyclonal goat anti-mouse TNF-α antibody, substrate and chromagen TMB. The incubation time for serum and standard TNF-α was extended for 4 hours and the development time for substrate incubation was 30 minutes.

Rabbit IL-8 measurements in rabbit serum were carried out by a special IL-8 ELISA kit, a gift from Professor Kouji Matsushima, Tokyo, Japan. Briefly, monoclonal anti-IL-8, guinea pig anti-rabbit IL-8 and alkaline phosphatase-conjugated rabbit anti-guinea pig immunoglobulin G antibodies were employed as capture, second and detection antibodies, respectively. For methods, see Ikeda et al. (106).

Result affected by treatment with IT9302. Histologically similar pancreatic changes were observed in the two groups while there was a significant reduction in interstitial neutrophil infiltration in the lungs.

CONCLUSION

IT9302 downregulates TNF-α and IL-8 production in a model of bile acid induced acute pancreatitis, and blocks neutrophil infiltration in lungs of these treated rabbits, thereby preventing the development of ARDS-like syndrome in these animals, resulting in a reduction of mortality from 60% to 0% after 12 hours. Interleukin 1 is regarded as an important inducer of acute pancreatitis (see ref. 107) and thereby supporting our hypothesis that IT9302 can block all IL-1 inducible effects. The reason why human IT9302 can be used in a rabbit model could be explained by the observation made by Dan Gaur et al. and published this year in Nature (108) where he showed that rabbit (Lagomorpha) proteins are phylogenetically more close to primates (human) proteins than to other rodents (mouse, rat, . . . ) proteins.

EXAMPLE 15

IT9302 as a Treatment of Cancer and in the Prevention of Metastasis

It was recently demonstrated (111) that systemic administration of cellular IL-10 induces an effective, specific and long-lived immune response against established tumours in mice in vivo. It was suggested that this effect is partially

TABLE 4

| Acute pancreatitis in rabbit, by 5% bile acid, content of TNF-α in serum (pg/ml ± SEM) | | | | | |
| --- | --- | --- | --- | --- | --- |
| 0 | 1 | 3 | 6 | 9 | 12 |
| 1210 ± 396 | 1206 ± 239 | 1918 ± 374 | 1662 ± 357 | 1884 ± 698 | 915 ± 431 |
| Acute pancreatitis, treated with human IT9302, 30 minutes before 5% bile acid, content of TNF-α in serum (pg/ml ± SEM) | | | | | |
| 0 | 1 | 3 | 6 | 9 | 12 |
| 347 ± 77 | 739 ± 339 | 697 ± 146 | 658 ± 156 | 872 ± 594 | 463 ± 203 |

TABLE 5

| Acute pancreatitis, by 5% bile acid, content of IL-8 in serum (pg/ml ± SEM) | | | | | |
| --- | --- | --- | --- | --- | --- |
| 0 | 1 | 3 | 6 | 9 | 12 |
| 1154 ± 351 | 780 ± 153 | 2210 ± 459 | 2690 ± 468 | 2196 ± 1058 | 1833 ± 1114 |
| Acute pancreatitis, treated with human IT9302, 30 minutes before 5% bile acid, content of IL-8 in serum (pg/ml ± SEM) | | | | | |
| 0 | 1 | 3 | 6 | 9 | 12 |
| 875 ± 181 | 695 ± 205 | 900 ± 178 | 1037 ± 244 | 1207 ± 210 | 1087 ± 216 |

SUMMARY

Maximum TNF-α induction was achieved at 3 hours, and maximum IL-8 at 6 hours. Both TNF-α and IL-8 levels in the blood circulation were markedly downregulated for 0 to 12 hours. The levels of pancreatic enzymes in the blood were also measured (amylase, lipase and tryptase) and they all showed peaks after 3–6 hours after induction of acute pancreatitis, but none of these enzymes appeared to be explained by the renowned effects of IL-10 on diverse cell types, including co-stimulation of T cell proliferation, chemoattraction of CD8+T cells, and stimulation of lymphokine-activated killer cell activity. They also observed that human IL-10 can reverse the local immunosuppressive effect of viral IL-10. Another research group confirmed the potential therapeutic role of IL-10 administration in cancer (112) since they observed that IL-10 inhibits metastasis through a natural killer cell-dependent mechanism in an in vivo experiment with mice having different tumours, including metastasizing malignant melanoma. Kundu et al. (1996) (113) reported that IL-10 exerts anti-metastatic and anti-tumour effects in a murine model of human breast cancer.

These observations indicate a potential role for human IL-10 and for IT9302 administration in the biological therapy of cancer.

EXAMPLE 16

IT9302 as an Immune Adjuvant in the Treatment of Viral Infections

IL-10 is known to possess certain anti-viral capacities. Thus, Kollmann et al. (1996) (114) found that IL-10 inhibits acute in vivo HIV infection of SCID mice with human fetal thymus and liver. We observed that two of the applicants/-researchers, when applying IT9302 in a cream formulation (total dose 400 to 500 µg) under plastic wrapping occlusion on the skin of the back for 24 hours, developed an increase in their total number of CD8+ T cells (60% and 90%, respectively) and an increase in serum IRAP concentration from 1 ng/ml to 2 ng/mml. In seven non-treated volunteers, the IRAP concentration never exceed 1.1 ng/ml. As an accidental and unexpected observation, both researchers observed that common warts (due to cutaneous HPV infection) showed clear signs of inflammation with redness and itching around the warts 3 to 4 days after the application of the IT9302-containing cream. The inflammatory reaction occurred synchronously on several fingers for one of the test persons, while the other person only had one wart on a finger. In both cases the warts quickly and gradually decreased in size during the following 4 to 7 days so that there were no clinical signs of remaining wart infection after 10 to 11 days. At a follow-up control 2 months later, there were no signs of recurrence of the infection.

We therefore find that IT9302, possibly through a systemic activation of NK cells and/or cytotoxic CD8+T cell activity, is able to evoke a latent immune response against cutaneous HPV infection, eventually resulting in clinical remission of the virus infection. Thus, IT9302 is a possible therapeutic alternative for the treatment of virus infections such as HIV and HPV infections.

EXAMPLE 17

IT9302 as an Immune Adjuvant in the Treatment of Inflammatory Joint Diseases (Arthritis)

Anti-IL-1 therapy as well as anti-TNFα therapy appear to have significant clinical potential in the treatment of arthritis (Maini, 1996) (115). As described elsewhere in this document, we have found IT9302 to be an inhibitor of TNFα production as well as a stimulator of IRAP (IL-1 receptor antagonist protein) from human mononuclear cells. Thus, IT9302 is a potential treatment modality of arthritis. This was supported by an observation of one of the applicants of this invention who, after applying IT9302 (approximately 500 µg) in a cream basis on the skin for 24 hours, observed a strong reduction in chronic joint pains due to arthritis. This observation was made three times and in each case the symptoms gradually recurred during the following week after removal of the IT9302 application. We are thus finding in vivo support of the arguments for using IT9302 in the treatment of acute or chronic inflammatory reactions such as arthritis or other auto-immune diseases.

REFERENCES

1. Bendtzen K. Lymphokines in inflammation. Inflammation Basic Mechanisms Tissue Injuring Principles and Clinical Models (P Venge & A Lindbom eds) 1985; Almqvist & Wiksell International. Stockholm: 187–217.
2. Bendtzen K. Interleukin-1, Interleukin-6, and tumor necrosis factor in infection, inflammation and immunity. Immunol Lett 1988;19:183–192.
3. Larsen C. G. Leukocyte activating and chemotactic cytokines in cell-mediated immune reactions of the human skin. Acta Dermatovenerol. 1991; Suppl. 160:1–48
4. Fiorentino D. F., M. W. Bond, and T. R. Mosmann. 1989. Two types of mouse helper T cell. IV. Th2 clones secrete a factor that inhibits cytokine production by Th1 clones. J. Exp. Med., 170:2081.
5. Viera P., R. de Wall-Malefyt, M.-N. Dang, K. E. Johnson, R. Kastelein, D. F. Fiorentiono, J. E. de Vries, M.-G. Roncarolo, T. R. Mosmann, and K. W. Moore. 1991. Isolation and expression of human cytokine synthesis inhibitory factor (CSIF/IL-10) cDNA clones: homology to Epstein-Barr virus open reading frame BCRFI. Proc. Natl. Acad. Sci. (USA), 88:1172.
6. Moore, K. W., O'Garra A., de Waal Malefyt R., Vieira, Mosmann T. R. 1993. Interleukin-10, Annu Rev. Immunol, 11:165–90.
7. Kim, J. M., Brannan, C. I. Copeland N. G., Jenkins, N. A., Khan, T. A., Moore, K. W. 1992. Structure of the mouse interleukin-10 gene and chromosomal localization of the mouse and human genes. J. Immunol 148:3618–23.
8. Carter, D. B., Deibel, M. R-Jr, Dunn, C. J. et al. 1990. Purification, cloning, expression and biological characterization of an interleukin-1 receptor antagonist protein. NATURE 344:633–638.
9. Hannum, C. H., Wilcox, C. J., Arend, W. P. et al. 1990. Interleukin-1 receptor antagonist activity of a human interleukin-1 inhibitor. Nature 343:336–40.
10. Firestein, G. S., Boyle, D. L., Yu, C., et al. 1994. Synovial interleukin-1 receptor antagonist and interleukin-1 balance in rheumatoid arthritis. Arthritis Rheum 37:644–652.
11. Fisher, C. J.-Jr., Slotman, G. J., Opal, S. M., Pribble, J. P. et al. 1994. Initial evaluation of recombinant interleukin-1 receptor antagonist in the treatment of sepsis syndrome: a randomized, open-label, placebo-controlled multicenter trial. The IL-1RA Sepsis Syndrome Study Group. Crit-Care-Med. 22:12–21.
12. de Waal-Malefyt, R., Haanen J., Spits, H., et al. 1991. IL-10 and viral IL-10 strongly reduce antigen-specific human T cell proliferation by diminishing the antigen-presenting capacity of monocytes via down-regulation of class II MHC expression. J. Exp. Med. 174:915–24.
13. Gazzinelli, R. T., Oswald, I. P., James, S. L., Sher, A., 1992. IL-10 inhibits parasite killing and nitric oxide production by IFN-\-activated macrophages. J. Immunol. 148:1792–96.
14. Jinquan, T., Larsen, C. G., Gesser, B., Matsushima, K., Thestrup-Pedersen, K. 1993. Human IL-10 is a chemoattractant for CD8+ T lymphocytes and an inhibitor of IL-8-induced CD4+ T lymphocyte Migration. Journal of Immunology, 151:4545–4551.
15. Rousset F., E. Garcia, T. Defrance, C. Peronne, D.-H. Hsu, R. Kastelein, K. W. Moore, and J. Banchereau. 1992. IL-10 is a potent growth and differentiation factor for activated human B lymphocytes. Proc. Natl. Acad. Sci. USA, 175:671.
16. Howard, M., O'Garra, A., Ishida, H., de Waal Malefyt, R., de Vries, J. 1992. Biological properties of Interleukin-10. J. Clin. Immunol 12:239–47.
17. Kuhn, R., Lohler, J., Rennick, D., Rajewsky, K., Muller, W. 1993. Interleukin-10-deficient mice develop chronic enterocolitis. Cell 75: 263–74.

18. Sher, A., Fiorentino, D. F., Caspar, P., Pearce, E., Mosmann, T. 1991. Production of IL-10 by CD4+ lymphocytes correlates with down-regulation of Th1 cytokine synthesis in helminth infection. J. Immunol. 147:2713–16.
19. Clerici, M., Shearer, G. M. 1993 Immunology Today. 14:107–111.
20. Bry, K., Lappalainen, U. 1994. Interleukin-4 and transforming growth factor-beta 1 modulate the production of interleukin-1 receptor antagonist and prostaglandin E2 by decidual cells. Am-J-obstet-Gynecol 170 (4): 1194–1198
21. Firestein, G., S., Boyle, D. L., Yu, C., Paine, M. M., Whisenand, T. D., Zvaifler, N. J., Arend, W. P. 1994. Synovial interleukin-1 receptor antagonist and interleukin-1 balance in rheumatoid arthritis. Arthritis-Rheum, 37/5: 644–652
22. Roberge, C. J., De-Medicis, R., Dayer, J. M., Rola-Pleszcyczynski, M., Naccahe, P. H., Poubelle, P. E. 1994. Crystal-induced neutrophil activation: V. Differential production of biologically active IL-1 receptor antagonist. J. Immunol 152/11: 5485–5494
23. McCall, R. D., Haskill, S., Zimmermann, E. M., Lund, P. K., Thompson, R. C., Sartor, R. B. 1994. Tissue interleukin 1 and interkeukin-1 receptor antagonist expression in entercolitis in resistant and susceptible rats. Gastroenterology (4): 960–72
25. Kimble, R. B., Vannice, J. L, Bloedow, D. C., Thompson, R. C., Hopfer, W., Kung, V. T., Brownfield, C., Pacifici, R. 1994. Interleukin-1 receptor antagonist decreases bone loss and bone resorption in ovariectomized rats. J. Clin Invest. 93/5: 1959–1967
26. Kline, J. N., Geist, L. J., Monick, M. M., Stinski, M. F., Hunninghake, G. W., 1994. J. Immunol. 152 (5): 2351–7
27. Tompkins, R. G. 1994. Human recombinant-interleukin-1 receptor antagonist in the treatment of sepsis syndrome (editorial; comment). Crit-Care-Med. 22 (1): 3, 22 (1): 12 –21
28. Everaerdt, B., Brouckaert, P., Fiers, W. 1994. Recombination IL-1 receptor antagonist protects against TNF-induced lethality in mice. J. Immunol. 152/10: 5041–5049
29. Fischer, C. J. Jr.; Slotman, G. J., Opal, S. M., Pribble, J. P., Bone, R. C., Emmanuel, G., Ng, D., Bloedow, D. C., Catalano, M. A. 1994. Initial evaluation of human recombination interleukin-1 receptor antagonist in the treatment of sepsis syndrome; a randomized, open-label, placebo-controlled multicenter trial. The IL-1RA Sepsis Syndrome Study Group (see comments). Crit-Care-Med. 22 (1): 12–21, 22 (1): 3
30. Gomez-Reino-Carnoto, J. J. 1994. New terapies in rheumatoid arthritis. Med-Clin 543–545.
32. Nishihara, T., Ohsaki, Y., Ueda, N., Saito, N., Mundy, G. R. 1994. Mouse interleukin-1 receptor antagonist induced by *actinobacillus* actinomycetemcomitans lipopolysaccharide blocks the effects of interleukin-1 om bone resorption and osteoclast-like cell formation. Infect-Immun. 62(2): 390–7
33. Simon, C., Frances, A., Piquette, G. N., el-Danasouri, I., Zurawski, G., Dang, W., Polan, M. L. 1994. Embryonic implantation in mice is blocked by interleukin-1 receptor antagonist (see comments). Endocrinology. 134(2): 521–8, 134(2): 519–20
34. Baergen, R., Benirschke, K., Ulich, T. R., 1994. Cytokine expression in the placenta. The role of interleukin 1 and interleukin 1 receptor antagonist expression in chorioamnionitis and parturition. Arch-Pathol-Lab-Med. 118(1): 52–5
35. Tang, W. W., Feng, L., Vannice, J. L., Wilson, C. B. 1994. Interleukin-1 receptor antagonist ameliorates experimental antiglomerular basement membrane antibody-associated flomeulonephritis. J. Clin-Invest. 93(1): 279–9.
36. Cassatella, M. A., Meda, L., Gasperini, S., Calzetti, F., Bonara, S. 1994.
37. Interleukin 10 (IL-10) upregulates IL-1 receptor antagonist production from lipopolysaccharide-stimulated human polymorphonuclear leukocytes by delaying mRNA degradation. J. Exp-Med. 179/5: 1695–1699
38. Mancini, R., Bendetti, A., Jezequel, A. M. 1994. An interleukin-1 receptor antagonist decreases fibrosis induced by dimethylnitrorsamine in rat liver. Virchows-Arch. 424/1: 25–31
39. Lukacs, N. W., Kunkel, S. L., Burdick, M. D., Lincoln, P. M., Strieter, R. M. 1993.
40. Interleukin-1 receptor antagonist blocks chemokine production in the mixed lymphocyte reaction. Blood. 82(12): 3668–74
41. Bandara, G., Mueller, G. M., Galea-Lauri, J., Tindal, M. H., Georgescu, H. I., Suchanek, M. K., Hung, G. L., Gloriso, J. C., Robbins, P. D., Evans, C. H. 1993.
42. Intraarticular expression of biologically active interleukin 1-receptor-antagonist protein by ex vivo transfer. Proc-Natl-Acad-Sci-U-S-A. 90(22): 10764–8
43. Dinarello, C. A. 1994. Anti-interleukin-1 strategies in the treatment of the septic shock syndrome. Can-J-infect-Dis. 5(suppl. A): 9A–16A
44. Oelmann, E., Topp, M. S., Reufi, B., Papadimitriiou, C., Koeningsmann, M., Oberberg, D., Thiel, E., Berdel, W. E. 1994. Int.-J-Oncol. 4/3: 555–558
45. Estrov, Z. 1993. Interruption of autocrine and paracrine growth-stimolatory mechanisms: a new therapeutic stratefy for chronic myelogenous leukemia. Semin-Hematol. 30(3 suppl 3): 35–6
46. Wooley, P. H., Whalen, J. D., Chapman, D. L., Berger, A. E., Richard, K. A., Aspar, D. G., Staite, N. D. 1993. The effect of an interleukin-1 receptor antagonist protein on type II collagen-induced arthritis and antigen-induced arthritis in mice. Arthritis Rheum. 36 (9) 1305–1314
47. Peterson, C. M., Hales, H. A., Hatasaka, H. H., Mitchell, M. D., Rittenhouse, L., Jones, K. P. 1993. Interleukin-1 beta (IL-1 beta) modulates prostaglandin production and the natural IL-1 receptor antagonist inhibits ovulation in the optimally stimulated rat ovarian perfusion model. Endocrinology 133 (5): 2301–2306
48. Estrov, Z., Kurzrock, R., Talpaz, M. 1993. Role of interleukin-1 inhibitory molecules in therapy of acute and chronic myelogenous leukemia. Leuk. Lymphoma 10 (6): 407–418
49. Chensue, S. W., Bienkowski, M., Eessalu, T. E., Warmington, K. S., Hershey, S. D., Lukacs, N. W., Kunkel, S. L. 1993. nous IL-1 receptor antagonist protein (IRAP) regulates schistosome egg granuloma formation and the regional lymphoid response. J. Immunol. 151 (7): 3654–3662
50. Bowyer, J. F., Davies, D. L., Schmued, L., Broening, H. W., Newport, G. D., Slikker, W Jr., Holson, R. R. 1994. Further studies of the role f hyperthermia in methamphetamine neurotoxicity. J. Pharmacol. Exp. Ther. 268/3: 1571–1580
51. Cole, O. F., Sullivan, M. H. F., Elder, M. G. 1993. The 'interleukin-1 receptor antagonist' is a partial agonist of prostaglandin synthesis by human decidual cells. Prostaglandins 46/6: 493–498
52. Jenkins, J. K., Arend, W. P. 1993. Interleukin 1 receptor antagonist production in human monocytes is induced by IL-1alpha, IL-3, and IL-4 and GM-CSF. Cytokine 5/5: 407–415

53. Coceani, F., Lees, J., Redford, J., Bishai, I. 1992. Interleukin-1 receptor antagonist: effectiveness against interleukin-1 fever. Can. J. Pharmacol. 70 (12): 1590–1596
54. Schiro, R., Longoni, D., Rossi, V., Maglia, O., Doni, A., Arsura, M., Carrara, G., Masera, G., Vannier, E., Dinarello, C. A., Rambaldi, A., Biondi, A. 1994. Suppression of juvenile chronic myelogenous leukemia colony growth by interleukin-1 receptor antagonist. Blood 83/2: 460–465
55. Watson, M. L., Smith, D., Bourne, A. D., Thompson, R. C., Westwick, J. 1993. Cytokines contribute to airway dysfunction hyperreactivity, pulmonary eosinophil accumulation and tumor necrosis factor generation by pretreatment with an interleukin-1 receptor antagonist. Am. J. Respir. Cell Mol. Biol. 8 (4): 365–369
56. Abhyankar, S., Gilliland, D. G., Ferrara, J. L. M. 1993. Interleukin-1 is a critical effector molecule during cytokine dysregulation in graft-versus-host disease to minor histocompatibility antigens. Transplantation 56/6: 1518–1523
57. Lan, H. Y., Nikolic Paterson, D. J., Zarama, M., Vannice, J. L., Atkins, R. C. 1993. Suppression of experimental crescentic glomerulonephitis by the interleukin-1 receptor antagonist. Kidney Int. 43 (2): 479–485
58. Herve, P. 1993. Prevention and treatment of acute GvHD —New modalities. Nouv. Rev. Fr. Hematol. 35/3: 295–297
59. Conti, P., Panara, M. R., Barbacane, R. C., Placido, F. C., Bongrazio, M., Reale, M., Dempsey, R. A., Fiore, S. 1992. Blocking the interleukin-1 receptor inhibits leukotriene B4 and prostaglandin E2 generation in human monocyte cultures. Cell Immunol. 145 (1): 199–209
60. Kristensen, M., Deleuran, B., Eedy, D. J., Feldmann, M., Breathnach, S. M., Brennan, F. M. 1992. Distribution of interleukin-1 receptor antagonist protein (IRAP), interleukin-1 receptor, and interleukin-1 alpha in normal and psoriatic skin, Decreased expression of IRAP in psoriatic lesional epidermis. Br. J. Dermatol. 127 (4): 305–311
61. Romero, R., Sepulveda, W., Mazor, M., Brandt, F., Cotton, D. B., Dinarello, C. A:, Mitchell, M. D. 1992. The natural interleukin-1 receptor-antagonist in term and preterm parturition. Am. J. Obstet. Gynecol. 167 (4 Pt 1): 863–872
62. Dinarello, C. A. 1992. Reduction of inflammation by decreasing production of interleukin-1 or by specific receptor antagonism. Int. J. Tissue. React. 14 (2): 65–75
63. Conti, P., Panara, M. R., Barbacane, R. C., Bongrazio, M:, Dempsey, R. A., Reale, M. 1993. Human recombinant IL. 1 receptor antagonist (IL-1Ra) inhibits leukotriene B4 generation from human-monocyte suspensions stimulated by lipopolysaccharide (LPS). Clin. Exp. Immunol. 91/3: 526–531
64. DeForge, L. E., Tracey, D. E., Kenney, J. S., Remick, D. G. 1992. Interleukin-1 receptor antagonist protein inhibits interleukin-8 expression in lipopolysaccharide-stimuled human whole blood. Am. J. Pathol. 140 (5): 1045–1054
65. Porat, R., Poutsiaka, D. D., Miller, L. C., Granowitz, E. V., Dinarello, C. A. 1992. Interleukin-1 (IL-1) receptor blockade reduces endotoxin and Borrealia burgdor-feri-stimulated IL-8 synthesis in human monoclear cells. Faseb. J. 6 (7): 2482–2486
66. Boermeester, M. A., van Leeuwen, P. A. M., Schneider, A. J., Houdijk, A. P. J., Ferwerda, C. C., Wesdorp, R. I. C. 1993. Interleukin-1 receptor antagonist: A new therapeutic agent in the treatment of septic syndrome. Ned. Tijdschr. Geneeskn. 137/7: 337–342
67. Smith, R. J., Chin, J. E., Sam, L. M., Justen, J. M. 1991. Biologic effects of an interleukin-1 receptor antagonist protein on interleukin-1-stimulated cartilage erosion and chondrocyte responsiveness. Arthsitis Rheum. 34 (1): 78–83
68. Conti, P. Barbacane, R. C., Panara, M. R., Reale, M., Placido, F. C., Fridas, S., Bongrazio, M., Dempsey, R. A. 1992. Human recombinant interleukin-1 receptor antagonist (hrIL-1ra) enhances the stimulatory effect of interleukin-2 on natural killer cell activity against MOLT-4 target cells. Int. J. Immunopharm. 14/6: 987–993
69. Selig, W., Tocker, J. 1992. Effect of interleukin-1 receptor antagonist on antigen-induced pulmonary responses in guinea pigs. Eur. J. Pharmacol. 213/3: 331–336
70. McCarthy, P. L. Jr., Abhyankar, S., Neben, S., Newman, G., Sieff, C., Thompson, R. C., Burakoff, S. J., Ferrara, J. L. M. 1991. Inhibition of interleukin-1 by an interleukin-1 receptor antagonist prevents graft-versus-host diseases. Blood 78/8: 1915–1918
71. Estrov, Z, Kurzrock, R., Wetzler, M., Kantarjian, H., Blake, M., Harris, D., Gutterman, J. U., Talpaz, M. 1991. Suppression of chronic myelongenous leukemia colony growth by interleukin-1 (IL-1) receptor antagonist and soluble IL-1 receptors: A novel application for inhibitors of IL-1 activity. Blood 78/6: 1476–1484
72. Thomas, T. K., Will, P. C., Srivastava, A., Wilson, C. L., Harbison, M., Little, J., Chesonis, R. S., Pignatello, M., Schmolze, D., Symington, J., Kilin, P. L., Thompson, R. C. 1991. Evaluation of an interleukin-1 receptor antagonist in the rat acetic acid-induced colitis model. Agents Actions 34/1-2: 187–190
73. Carter, D. B., Deibel, M. R. Jr., Dunn, C. J., Tomich, C. S. C., Laborde, A. L., Slightom, J. L., Berger, A. E., Bienkowski, M. J., Sun, F. F., McEwan, R. N., Harris, P. K. W., Yen, A. W., Waszak, G. A., Chosay, J. G., Sieu, L. C., Hardee, M. M., Zurcher Neely, H. A., Reardon, I. M., Heinrikson, R. L. et al. 1990. Purification, cloning expression and biological characterization of an interleukin-1 receptor antagonist protein. Nature 344/6267: 633–638
74. Larsen C. G, Anderson A. O, Apella E., Oppenheim J. J., Matsushima K., 1989. Science 243:1464;
75. Larsen C. G., Jinquan T., Deleurant B., Thestrup-Pedersen K. 1993, IL-10 is a potent regulator of the chemotactic response of mononuclear cells, but not of granulocytes. J. Invest. Dermatol. Vol 100, No 6
76. Sankoff and Kruskal in chapter 1 of "Time Warps, String Edits, and Macromolecules: The Theory and Practice of Sequence Comparison" (Addison-Wesley, Reading, Mass. 1983).
77. Berzofsky, *Science* 229, (1985) 932–940
78. Bowie et al., *Science* 247, (1990) 1306–1310
79. Wasserman et al., *J. Immunol.* 87, 1961, 290–295
80. Levine et al., *Methods in Enzymology* 11, 1967, 928–936
81. Lewis et al., *Biochemistry* 22, 19B3, 948–954
82. Rene de Waal Maletyt, John Abrahams, Bruce Bennet, Carl G. Figdor and Jan E. de Vries (1991), Interleukin 10 (IL-10) Inhibits Cytokine Synthesis by Human Monocytes: An Autoregulatory Role of IL-10 Produced by Monocytes. *J. Exp. Med.* 174, 1209–1220
83. Szoka et al., Ann. Rev. Biophys. Bioeng. 9, 1980, 467
84. U.S. Pat. No. 4,235,871
85. U.S. Pat. No. 4,501,728
86. U.S. Pat. No. 4,837,028.
87. Walter H. Gotlieb, John S. Abrams, Joanna M. Watson, Thierry J. Velu, Jonathan S. Berek, Otoniel Martinez-Meza (1992), Presence of interleukin 10 (IL-10) in the ascites of patients with ovarian and other intra-abdominal cancers. *Cytokine* 4, No. 5, 385–390

88. Blancho G., P. Gianello, Sh. Germana, M. Baetscher, D. H. Sachs and Chr. LeGuern (1995), Molecular identification of porcine interleukin 10: Regulation of expression in kidney allograf model. *Proc. Natl. Acad. Sci. USA* 92, 2800–2804
89. Howard, M., T. Muchamuel, S. Andrade, S. Menon (1993), Interleukin 10 protects mice from lethal endotoxemia. J. Exp. Med. 177, 1205–1208
90. Chernoff, A. E., E. V. Granowitz, L. Shapiro, E. Vannier, G. Lonnemann, J. B. Angel, J. S. Kennedy, A. R. Rabson, S. Wolff, C. A. Dinarello (1995), A randomized, controlled trial of IL-10 in humans. Inhibition of inflammatory cytokine production and immune responses. J. Immunol. 154, 5492–5499
91. Banerjee, A. K., S. W. Galloway and A. N. Kingsnorth (1994), Experimental models of acute pancreatitis. *Br. J. Surg.* 81, 1096–1103
92. Hong, S. S., D. S. Chin, T. S. Cho, S. E. Kim (1962), Experimental pancreatitis induced by alcohol and bile in rabbits. *Annals of Surgery* 156(6), 929–939
93. Bodansky, M. (1984), *Principles of Peptide Synthesis*, Springer-Verlag, Berlin
94. Pelton, J. T., et al., *Proc. Natl. Acad. Sci. USA* 82, 233–239
95. Dyson, H., et al. (1988), *Annual Review of Biophysics and Biophysical Chemistry* 17, 305–324).
96. Nakanishi, H., et al. (1993), Peptidomimetics of the immunoglobulin supergene family—a review. *Gene* 137, 51–56
97. U.S. Pat. No. 5,446,128
98. Walter et al. (1995), *Biochemistry* 34, 12118–25
99. Marshall, G. R. (1993), *Tetrahedron* 49, 3547–3558
100. Merrifield, R. B. (1963), *J. Amer. Chem. Soc.* 85, 2149–2154)
101. Kent, S. B. H. (1988), *Annu. Rev. Biochem.* 57, 957–989
102. Carpino, L. A. and Han, G. Y. (1972), *J. Org. Chem.* 37, 3404–3409
103. Stewart, J. M. and Young, J. D. (1983), "Solid Phase Peptide Synthesis", Pierce Chemical Company, Rockford, Ill.
104. Atherton, E. and Sheppard, R. C. (1989), "Solid Phase Peptide Synthesis", IRL Press at Oxford University Press
105. Pennington, M. W. and Dunn, B. M. (eds.) (1994), "Peptide Synthesis Protocols", Humana Press, Totowa, N.J.
106. Ikeda, N. et al. (1995), *Infection and Immunity*, 4812–4817
107. Fink, G. W. and Norman, J. G. (1996), "Intrapancreatic Interleukin-1β Gene Expression by Specific Leukocyte Populations during Acute Pancreatitis", *J. Surgical Research* 63, 369–373
108. Gaur, D. et al. (1996), "Phylogenetic position of the order Lagomorpha (rabbits, hares and allies)", *Nature*, 379, 333–335
109. Poli, G. et al. (1994), *Proc. Natl. Acad. Sci. USA* 91, 108–112
110. Jensen, I. M. et al. (1993), *Analyt. Cell. Pathol.* 5, 213–223
111. Berman, R. M., Suzuki, T. et al. (1996), "Systemic administration of cellular IL-10 induces an effective, specific, longlived immune response against established tumors in mice", *J. Immunol.* 157, 231–238
112. Zheng, L. M., Ojcius, D. M. et al. (1996), "IL-10 inhibits tumor metastasis through an NK cell-dependent mechanism", *J. Exp. Med.* 184, 579–584
113. Kundu, N., Beaty, T. L. et al. (1996), "Antimetastatic and anti-tumor activities of IL-10 in a murine model of breast cancer", *J. Natl. Cancer Inst.* 88, 479–480
114. Kollmann, T. R., Pettoello-Mantovani, M. et al. (1996), "inhibition of acute in vivo HIV infection by human IL-10 treatment of SCID mice implanted with human fetal thymus and liver", *Proc. Natl. Acad. Sci. USA* 93, 3126–3131
115. Maini, R. N. (1996), "A perspective on anti-cytokine and anti T cell directed therapies in rheumatoid arthritis", *Clin. Exp. Rheumatol.* 13, suppl. 12, S35–40

What is claimed is:

1. A polypeptide in at least partially purified form, which is six to 20 amino acids in length, and which comprises the following sequence $X_A$-$X_4$-$X_B$-$X_5$-$X_C$-$X_6$ wherein $X_4$ and $X_5$ are independently selected from the group consisting of Met, Ile, Leu, Val, norvaline, norleucine, methionine-S-oxide, N-methylvaline, N-methyl isoleucine, allo-leucine, and their D-isomers;

$X_6$ is selected from the group consisting of Asn, Asp, Gln, Glu, and their D-isomers, $X_A$ is L-Thr or D-Thr, $X_B$ is L-Lys, L-Orn, L-Dab, or one of their D-isomers, and $X_C$ is L-Arg or D-Arg, wherein at least one of the following conditions (I)—(IV) is true:

I) at least one of $X_A$, $X_B$, $X_C$, $X_4$, $X_5$ or $X_6$ is an amino acid other than a genetically encoded amino acid, the genetically encoded amino acids being here defined as amino acids selected from the group consisting of glycine, L-alanine, L-serine, L-threonine, L-leucine, L-isoleucine, L-methionine, L-valine, L-cysteine, L-asparagine, L-aspartic acid, L-glutamine, L-glutamic acid, L-arginine, L-lysine, L-histidine, L-phenylalanine, L-tryptophan, L-tyrosine, and L-proline, II) the polypeptide is cyclized, III) the aminoterminal amino acid residue is acylated, or IV) the carboxyterminal amino acid residue is amidated, said polypeptide having at least one of the following properties:

a) induces inhibition of spontaneous IL-S production by human monocytes, b) induces inhibition of IL-1β induced IL-8 production by human peripheral blood mononuclear cells (PEMC), c) induces production of interleukin-1 receptor antagonistic protein (IRAP) by human monocytes, d) induces chemotactic migration of CD8+ human T lymphocytes in vitro,
e) desensitizes human CD8+ T cells resulting in an unresponsiveness towards rhIL-10,
f) suppresses the chemotactic response of CD4+ T human lymphocytes towards IL-8,
g) suppresses the chemotactic response of human monocytes towards MCAF/MCP-1,
h) inhibits class II MHC molecule expression on human monocytes stimulated by IFN-γ,
i) induces the production of IL-4 by cultured normal human CD4+ T cells,
j) reduces TNFα production in human mixed leukocyte reaction, or
k) downregulates TNFα and IL-8 production in a rabbit model of bile acid induced acute pancreatitis and reduces neutrophil infiltration in the lungs of the treated rabbits.

2. A polypeptide according to claim 1, which comprises the following sequence $X_3$-Thr-$X_4$-Lys-$X_5$-Arg-$X_6$ (SEQ ID NO:20), wherein $X_3$, $X_4$ and $X_5$ are independently selected from the group consisting of Met, Ile, Leu and Val; and $X_6$ selected from the group consisting of Asn, Asp, Gln and Glu, wherein at least one of the following conditions (I)–(IV) is true:
I) at least one of $X_3$, $X_4$, $X_5$, $X_6$, Thr, Lys, and Arg is independently substituted with an amino acid other than a genetically encoded amino acid,
II) the polypeptide is cyclized,
III) the aminoterminal amino acid residue is acylated, or
IV) the carboxyterminal amino acid residue is amidated.

3. A polypeptide according to claim 1, which comprises the following sequence $X_2$-$X_3$-Thr-$X_4$-Lys-$X_5$-Arg-$X_6$ (SEQ ID NO: 21)

wherein $X_2$ is Tyr or Phe, $X_3$, $X_4$, and $X_5$, are independently selected from the group consisting of Met, Ile, Leu and Val; and $X_6$ is selected from the group consisting of Asn, Asp, Gln and Glu, wherein at least one of the following conditions (I)–(IV) is true:
I) at least one of $X_2$, $X_3$, $X_4$, $X_5$, $X_6$, Thr, Lys, and Arg is independently substituted with an amino acid other than a genetically encoded amino acid,
II) the polypeptide is cyclized,
III) the aminoterminal amino acid residue is acylated, or
IV) the carboxyterminal amino acid residue is amidated.

4. A polypeptide according to claim 1, which comprises the following sequence $X_1$-$X_2$-$X_3$-Thr-$X_4$-Lys-$X_6$-Arg-$X_6$, (SEQ ID NO:22), wherein $X_1$ is Ala or Gly, $X_2$ is Tyr or Phe, $X_3$, $X_4$, and $X_5$ are independently selected from the group consisting of Met, Ile, Leu and Val; and $X_6$ is selected from the group consisting of Asn, Asp, Gln and Glu, wherein at least one of the following conditions (I)–(Iv) is true;
I) at least one of $X_1$, $X_2$, $X_3$, $X_4$, $X_5$, $X_6$, Thr, Lys, and Arg is independently substituted with an amino acid other than a genetically encoded amino acid,
II) the polypeptide is cyclized,
III) the aminoterminal amino acid residue is acylated, or
IV) the carboxyterminal amino acid residue is amidated.

5. A polypeptide amounting to six to twenty amino acids which comprises the following sequence Thr-$X_4$-Lys-$X_5$-Arg-$X_6$ (SEQ ID NO:19), wherein $X_4$ and $X_5$ are independently selected from the group consisting of Met, Ile, Leu and Val; and $X_6$ is selected from the group consisting of Asn, Asp, Gln and Glu, or which comprises a sequence which differs from SEQ ID NO:19 solely in that at least one of Thr, Lys, and Arg in SEQ ID NO:19 is independently substituted with an amino acid selected from the group consisting of

| | |
|---|---|
| Aad | 2-Aminoadipic acid |
| bAad | 3-Aminoadipic acid |
| bAla | beta-Alanine, beta-Aminopropionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| bAib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| aHyl | alo-Hydroxylysine |
| 3Hyp | 3-Hydroxyproline |
| 4Hyp | 4-Hydroxyproline |
| Ide | Isodesmosine |
| aIle | allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| and | |
| Orn | Ornithine, | said polypeptide having at least one of the properties defined in claim 1.

6. A polypeptide according to claim 1, consisting of up to 15 amino acids.

7. A polypeptide according to claim 1 consisting of 10, 11, 12, 13, or 14 amino acids.

8. A polypeptide according to claim consisting of 9 amino acids.

9. The polypeptide of claim 4, wherein at least condition (I) is true.

10. The polypeptide of claim 3 wherein at least condition (I) is true.

11. The polypeptide of claim 2 wherein at least condition (I) is true.

12. The polypeptide of claim 1 wherein at least condition (I) is true.

13. The polypeptide of claim 1 which has the amino acid sequence Ala-Tyr-Met-Thr-Met-Lys-Ile-Arg-Asn (SEQ ID NO:1).

14. A polypeptide according to claim 1 which is cyclized.

15. A polypeptide according to claim 1 wherein the aminoterminal amino acid residue is acylated.

16. A polypeptide according to claim 1 wherein the carboxyterminal amino acid residue is amidated.

17. A liposome comprising a polypeptide according to claim 1.

18. A polypeptide according to claim 1 in substantially pure form.

19. A pharmaceutical composition comprising a polypeptide according to claim 1, or a salt or solvate of said polypeptide.

20. The polypeptide of claim 1 where SEQ ID NO: 19 is the C-terminal of said polypeptide and the polypeptide is not cyclized.

21. The polypeptide of claim 20 whose length does not exceed 10 amino acids.

22. The polypeptide of claim 1, said polypeptide being selected from the group consisting of polypeptides identical to SEQ ID NO: 19, SEQ ID NO: 20, SEQ ID NO: 21, and SEQ ID NO: 22, except that at least one of conditions (I)–(IV) applies.

23. The polypeptide of claim 1 where said amino acids, other than $X_A$, $X_B$, $X_C$, $X_4$, $X_5$, or $X_6$, are alpha or beta amino acids.

24. The polypeptide of claim 1 which is not more than 15 a.a. in length.

25. A polypeptide in at least partially purified form, which is six to 20 amino acids in length, and which comprises the following sequence

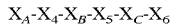

$X_A$ is L-Thr or an amino acid other than a genetically encoded amino acid, the genetically encoded amino acids being here defined as amino acids selected from the group consisting of glycine, L-alanine, L-serine, L-threonine, L-leucine, L-isoleucine, L-methionine, L-valine, L-cysteine, L-asparagine, L-aspartic acid, L-glutamine, L-glutamic acid, L-arginine L-lysine, L-histidine, L-phenylalanine, L-tryptophan, L-tyrosine, and L-proline, $X_B$ is L-Lys or an amino acid other than a genetically encoded amino acid, $X_C$ is L-Arg or an amino acid other than a genetically encoded amino acid, $X_4$ and $X_5$ are independently selected from the group consisting of L-Met, L-Ile, L-Leu, L-Val and an amino acid other than a genetically encoded amino acid, $X_6$ is L-Asn, L-Asp, L-Gln, L-Glu, or an amino acid other than a genetically encoded amino acid, no more than one of $X_A$, $X_B$, $X_C$, $X_4$, $X_5$ and $X_6$ is an amino acid which is other than a genetically encoded amino acid and other than the D-isomer of an L-amino acid recited as possible at that position, wherein at least one of the following conditions (I)–(IV) is true:

I) at least one $X_A$, $X_B$, $X_C$, $X_4$, $X_5$ or $X_6$ is an amino acid other than a genetically encoded amino acid, II) the polypeptide is cyclized, III) the aminoterminal amino acid residue is acylated, or IV) the carboxyterminal amino acid residue is amidated, said polypeptide having at least one of the following properties:

a) induces inhibition of spontaneous IL-8 production by human monocytes, b) induces inhibition of IL-1β induced IL-8 production by human peripheral blood mononuclear cells (PBMC), c) induces production of interleukin-1 receptor antagonistic protein (IRAP) by human monocytes, d) induces chemotactic migration of CD8+ human T lymphocytes in vitro, e) desensitizes human CD8+ T cells resulting in an unresponsiveness towards rhIL-10, f) suppresses the chemotactic response of CD4+ T human lymphocytes towards IL-8, g) suppresses the chemotactic response of human monocytes towards MCAF/MCP-1, h) inhibits class II MHC molecule expression on human monocytes stimulated by IFN-γ, i) induces the production of IL-4 by cultured normal human CD4+ T cells, j) reduces TNFα production in human mixed leukocyte reaction, or k) downregulates TNFα and IL-8 production in a rabbit model of bile acid induced acute pancreatitis and reduces neatrophil infiltration in the lungs of the treated rabbits, and wherein any non-natural or unusual amino acid referred to above is an amino acid selected from the group consisting of

| Aad | 2-Aminoadipic acid |
|---|---|
| bAad | 3-Aminoadipic acid |
| bAla | beta-Alanine, beta-Aminopropionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| bAib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| aHyl | alo-Hydroxylysine |
| 3Hyp | 3-Hydroxyproline |
| 4Hyp | 4-Hydroxyproline |
| Ide | Isodesmosine |
| aIle | allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| and | |
| Orn | Ornithine. |

26. The polypeptide of claim 25, where no more than one of the amino acids of said polypeptide which lie outside said sequence, if any, is an amino acid other than a genetically encoded amino acid and other than a D-isomer of one of the genetically encoded amino acids.

27. The polypeptide of claim 25, which is not more than 15 a.a. in length.

28. The polypeptide of claim 26, which is not more than 15 a.a. in length.

29. The polypeptide of claim 1, where $X_4$ and/or $X_5$ are independently selected from the group consisting of Met, Ile, Leu, Val, norvaline, norleucine, N-methylvaline, N-methyl isoleucine, allo-leucine, and their D-isomers, and $X_B$ is L-Lys, L-Orn, or one of their D-isomers.

30. The polypeptide of claim 1 where SEQ ID NO:19 is the C-terminal of said polypeptide.

31. A method of treating acute pancreatitis which comprises administration of a therapeutically effective amount of the composition of claim 19.

32. A method of treating ARDS-like syndrome which comprises administration of a therapeutically effective amount of the composition of claim 19.

33. The method of claim 31, further resulting in prevention of ARDS-like syndrome.

* * * * *

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
      (A) LENGTH: 9 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Ala Tyr Met Thr Met Lys Ile Arg Asn
1             5

(2) INFORMATION FOR SEQ ID NO:2:

(i) SEQUENCE CHARACTERISTICS:
      (A) LENGTH: 9 amino acids
      (B) TYPE: amino acid
      (C) STRANDEDNESS: single (D) TOPOLOGY: linear (ii) MOLECULE TYPE: peptide (xi) SEQUENCE DESCRIPTION: SEQ ID NO:2:

Ala Tyr Met Thr Ile Lys Met Arg Asn
1               5

(2) INFORMATION FOR SEQ ID NO:3:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:3:

Ala Phe Met Thr Leu Lys Leu Arg Asn
1               5

(2) INFORMATION FOR SEQ ID NO:4:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:4:

Ala Tyr Met Thr Met Lys Val Arg Glu
1               5

(2) INFORMATION FOR SEQ ID NO:5:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:5:

Gly Tyr Met Thr Met Lys Ile Arg Asp
1               5

(2) INFORMATION FOR SEQ ID NO:6:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:6:

Ala Phe Met Thr Met Lys Ile Arg Asp
1               5

(2) INFORMATION FOR SEQ ID NO:7:

(i) SEQUENCE CHARACTERISTICS:
         (A) LENGTH: 9 amino acids
         (B) TYPE: amino acid (C) STRANDEDNESS: single
            (D) TOPOLOGY: linear (ii) MOLECULE TYPE: peptide (xi) SEQUENCE DESCRIPTION: SEQ ID NO:7:

Ala Tyr Ile Thr Met Lys Ile Arg Asp
1               5

(2) INFORMATION FOR SEQ ID NO:8:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:8:

Ala Tyr Leu Thr Met Lys Ile Arg Asp
1               5

(2) INFORMATION FOR SEQ ID NO:9:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:9:

Ala Tyr Val Thr Met Lys Ile Arg Asp
1               5

(2) INFORMATION FOR SEQ ID NO:10:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:10:

Ala Tyr Met Thr Ile Lys Ile Arg Asp
1               5

(2) INFORMATION FOR SEQ ID NO:11:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:11:

Ala Tyr Met Thr Leu Lys Ile Arg Asp
1               5

(2) INFORMATION FOR SEQ ID NO:12:

(i) SEQUENCE CHARACTERISTICS:
            (A) LENGTH: 9 amino acids

```
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

Ala Tyr Met Thr Val Lys Ile Arg Asp
1               5

(2) INFORMATION FOR SEQ ID NO:13:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

Ala Tyr Met Thr Met Lys Ile Arg Asp
1               5

(2) INFORMATION FOR SEQ ID NO:14:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Ala Tyr Met Thr Met Lys Met Arg Asp
1               5

(2) INFORMATION FOR SEQ ID NO:15:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Ala Tyr Met Thr Met Lys Val Arg Asp
1               5

(2) INFORMATION FOR SEQ ID NO:16:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Ala Tyr Met Thr Met Lys Ile Arg Gln
1               5

(2) INFORMATION FOR SEQ ID NO:17:

(i) SEQUENCE CHARACTERISTICS:
```

(A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

Ala Tyr Met Thr Met Lys Ile Arg Glu
1               5

(2) INFORMATION FOR SEQ ID NO:18:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

Ser Pro Gly Gln Gly Thr Gln Ser Glu
1               5

(2) INFORMATION FOR SEQ ID NO:19:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: Xaa in position 2 is Met, Ile, Leu or
            Val; Xaa in position 4 is Met, Ile, Leu or Val;
            Xaa in position 6 is Asn, Asp, Gln or Glu.

(xi) SEQUENCE DESCRIPTION: SEQ ID NO:19:

Thr Xaa Lys Xaa Arg Xaa
1               5

(2) INFORMATION FOR SEQ ID NO:20:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: Xaa in position 1 is Met, Ile, Leu or
            Val; Xaa in position 3 is Met, Ile, Leu or Val;
            Xaa in position 5 is Met, Ile, Leu or Val;
            Xaa in position 7 is Asn, Asp, Gln or Glu.

(xi) SEQUENCE DESCRIPTION: SEQ ID NO:20:

Xaa Thr Xaa Lys Xaa Arg Xaa
1               5

(2) INFORMATION FOR SEQ ID NO:21:

(i) SEQUENCE CHARACTERISTICS:
        (A) LENGTH: 8 amino acids
        (B) TYPE: amino acid
        (C) STRANDEDNESS: single
        (D) TOPOLOGY: linear -continued

```
    (ii) MOLECULE TYPE: peptide (ix) FEATURE:
        (D) OTHER INFORMATION:  Xaa in position 1 is Tyr or Phe;
            Xaa in position 2 is Met, Ile, Leu or Val;
            Xaa in position 4 is Met, Ile, Leu or Val;
            Xaa in position 6 is Met, Ile, Leu or Val;
            Xaa in position 8 is Asn, Asp, Gln or Glu.

(xi) SEQUENCE DESCRIPTION: SEQ ID NO:21:

Xaa Xaa Thr Xaa Lys Xaa Arg Xaa
1               5

(2) INFORMATION FOR SEQ ID NO:22:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION:  Xaa in position 1 is Ala or Gly;
            Xaa in position 2 is Tyr or Phe;
            Xaa in position 3 is Met, Ile, Leu or Val;
            Xaa in position 5 is Met, Ile, Leu or Val;
            Xaa in position 7 is Met, Ile, Leu or Val;
            Xaa in position 9 is Asn, Asp, Gln or Glu.

(xi) SEQUENCE DESCRIPTION: SEQ ID NO:22:

Xaa Xaa Xaa Thr Xaa Lys Xaa Arg Xaa
1               5

(2) INFORMATION FOR SEQ ID NO:23:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

GCCTACATGA CAATGAAGAT ACGAAAC                                                27
```